(12) United States Patent
Coady et al.

(10) Patent No.: US 8,496,946 B2
(45) Date of Patent: Jul. 30, 2013

(54) ANTIMICROBIAL HYDROGELS, METHODS OF PREPARATION THEREOF, AND ARTICLES THEREFROM

(75) Inventors: Daniel Joseph Coady, San Jose, CA (US); Amanda Catherine Engler, San Jose, CA (US); James Lupton Hedrick, Pleasanton, CA (US); Shaoqiong Liu, Singapore (SG); Yi Yan Yang, Singapore (SG); Chuan Yang, Singapore (SG)

(73) Assignees: International Business Machines Corporation, Armonk, NY (US); Agency for Science, Technology and Research, Singapore (SG)

( * ) Notice: Subject to any disclaimer, the term of this patent is extended or adjusted under 35 U.S.C. 154(b) by 12 days.

(21) Appl. No.: 13/213,555

(22) Filed: Aug. 19, 2011

(65) Prior Publication Data

US 2012/0231060 A1 Sep. 13, 2012

Related U.S. Application Data

(60) Provisional application No. 61/451,491, filed on Mar. 10, 2011.

(51) Int. Cl.
*A61K 9/00* (2006.01)
(52) U.S. Cl.
USPC .......................................... 424/400; 424/484
(58) Field of Classification Search
None
See application file for complete search history.

(56) References Cited

U.S. PATENT DOCUMENTS

| | | | | |
|---|---|---|---|---|
| 5,840,823 A * | 11/1998 | Licht et al. | ...................... | 528/73 |
| 6,194,124 B1 | 2/2001 | Choi et al. | | |
| 6,818,018 B1 | 11/2004 | Sawhney | | |
| 2007/0225460 A1 | 9/2007 | Kulshrestha et al. | | |
| 2010/0008938 A1 | 1/2010 | Diwan et al. | | |
| 2010/0260743 A1 | 10/2010 | Diwan et al. | | |
| 2011/0150977 A1 | 6/2011 | Hedrick et al. | | |
| 2011/0151566 A1 | 6/2011 | Hedrick et al. | | |
| 2011/0152167 A1 | 6/2011 | Hedrick et al. | | |

OTHER PUBLICATIONS

Bartels et al., Antibiofouling Hybrid Dendritic Boltorn/Star PEG thiol-ene cross linked networks, ACS Appl. Mater. Interfaces 2011, 3, 2118-2129.*
Kuroda, et al., "Amphiphilic Polymethacrylate Derivatives as Antimicrobial Agents," J. Am. Chem. Soc. 2005, 127, 4128-4129, Published on Web Mar. 3, 2005.
Li, et al., "Controlled assembly of dendrimer-like DNA," Nature Materials, 3, 38-42, (2004); Published online: Dec. 21, 2003.
Li, et al., "Multiplexed detection of pathogen DNA with DNA-based fluorescence nanobarcodes," Nature Biotechnology, 23, 885-889, (2005); Published online: Jun. 12, 2005.
Lienkamp, et al., "Antimicrobial Polymers Prepared by ROMP with Unprecedented Selectivity: A Molecular Construction Kit Approach," J. Am. Chem. Soc. 2008, 130, 9836-9843, Published on Web Jul. 1, 2008.
Mowery, et al., "Mimicry of Antimicrobial Host-Defense Peptides by Random Copolymers," J. Am. Chem. Soc. 2007, 129, 15474-15476, Published on Web Nov. 23, 2007.
Nederberg, et al., "Biodegradable nanostructures with selective lysis of microbial membranes," Nature Chemistry, 2011, vol. 3 (5), p. 409-414 published online Apr. 3, 2011.
Noimark, et al., "The role of surfaces in catheter-associated infections", Chem. Soc. Rev., 2009, 38, 3435-3448; First published on the web Aug. 28, 2009.
Tew, et al., "De novo design of biomimetic antimicrobial polymers," PNAS Apr. 16, 2002 vol. 99 No. 8, 5110-5114.

* cited by examiner

*Primary Examiner* — Anand Desai
*Assistant Examiner* — Melissa Mercier
(74) *Attorney, Agent, or Firm* — Michael R. Roberts

(57) ABSTRACT

A covalently crosslinked hydrogel comprises a) three or more divalent poly(alkylene oxide) chains P' covalently linked at respective first end units to a branched first core group C', b) three or more divalent poly(alkylene oxide) chains P'' covalently linked at respective first end units to a branched second core group C'', the chains P'' comprising respective second end units which are covalently linked to between 0% and 100% of respective second end units of chains P' by divalent linking groups L'', and c) at least one pendant cationic block copolymer chain A'-B'. A'-B' comprises i) a divalent block A' comprising a poly(alkylene oxide) backbone chain having an end unit covalently linked to a second end unit of one of the chains P' by a divalent linking group L', and ii) a monovalent block B' comprising a first repeat unit, the first repeat unit comprising a backbone carbonate group and a cationic side chain group.

35 Claims, 21 Drawing Sheets

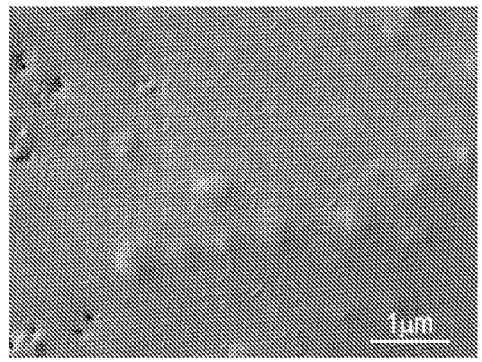
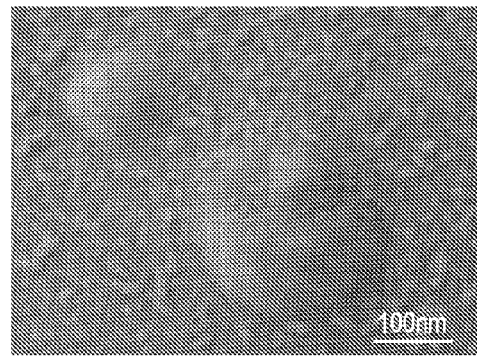
PEG-APC(14-7)-2
FIG. 6A    FIG. 6B
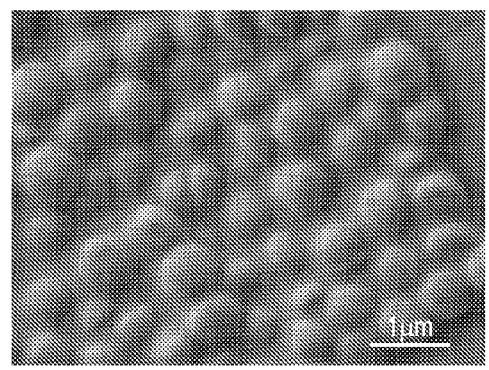
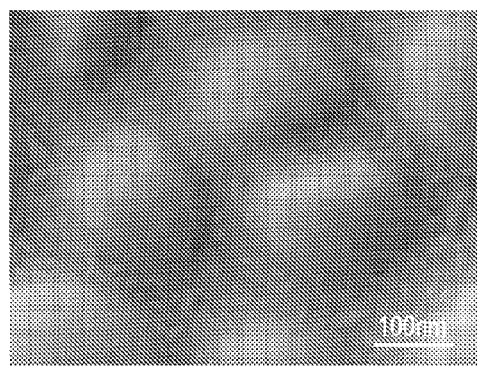
PEG-APC-0
FIG. 6C    FIG. 6D

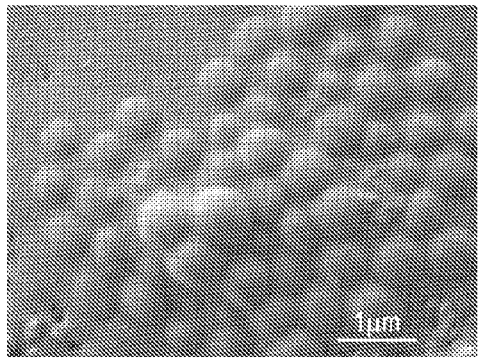
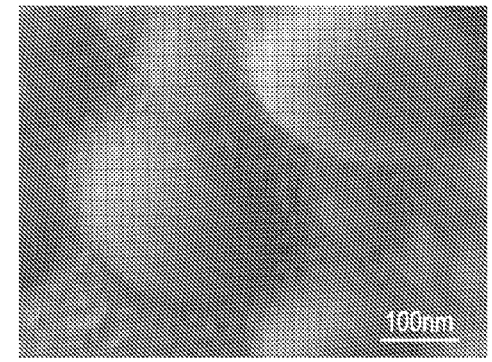
TEOA
FIG. 6E  FIG. 6F
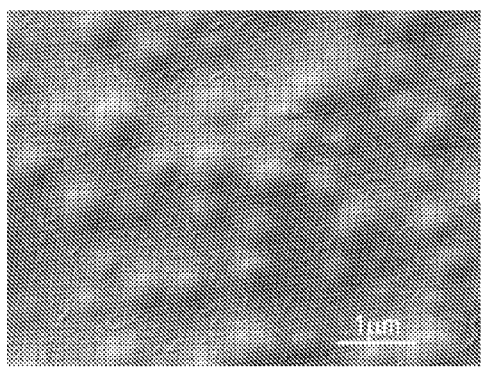
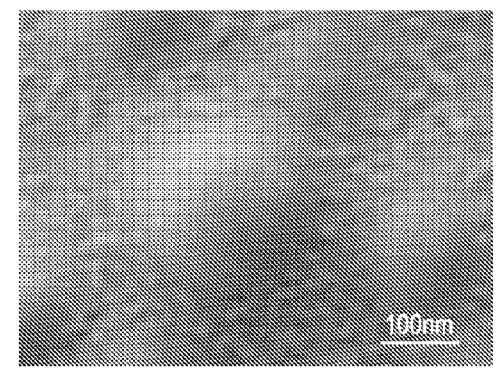
TSB
FIG. 6G  FIG. 6H

PBS

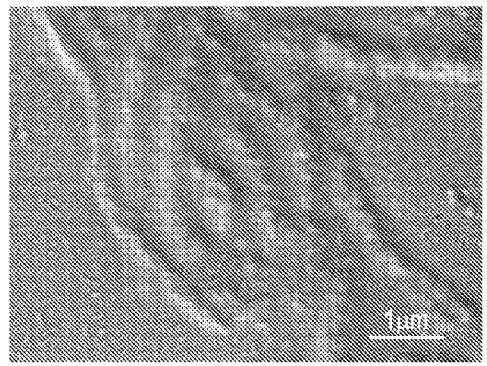 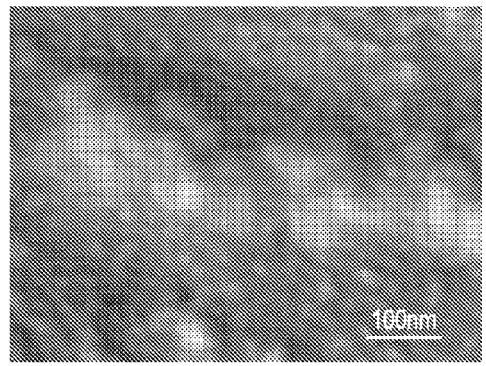
PEG-APC(18-25)-2
FIG. 7A                FIG. 7B
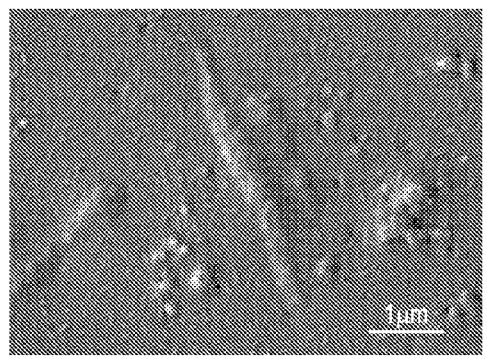 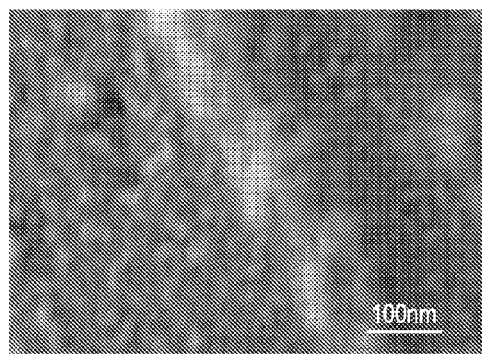
PEG-APC(18-25)-4
FIG. 7C                FIG. 7D

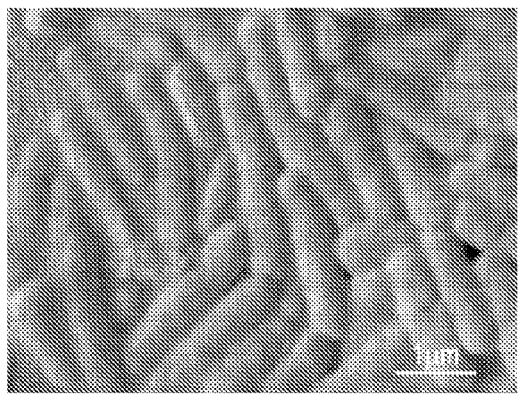
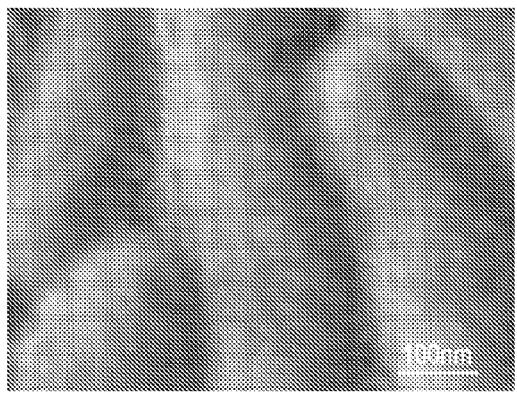
PEG-APC-0
FIG. 7E    FIG. 7F
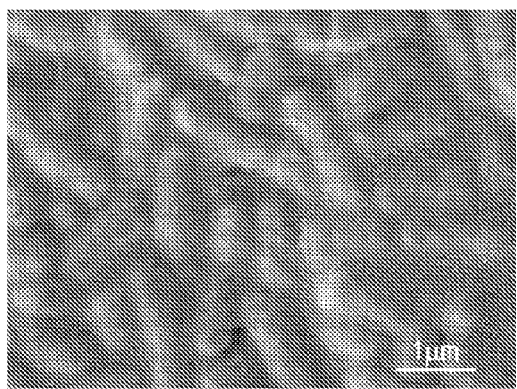
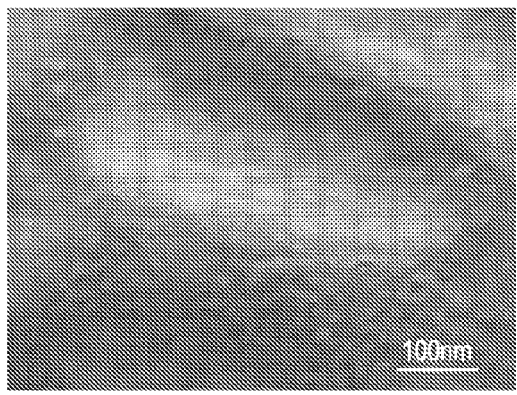
TCTP
FIG. 7G    FIG. 7H

SEQUENCE LISTING

```
<160> NUMBER OF SEQ ID NOS: 3

<210> SEQ ID NO 1
<211> LENGTH: 28
<212> TYPE: DNA
<213> ORGANISM: artificial sequence
<220> FEATURE:
<223> OTHER INFORMATION: synthetic
<300> PUBLICATION INFORMATION:
<301> AUTHORS: Y. Li, Y.T.H. Cu, D. Luo
<302> TITLE: Multiplexed detection of pathogen DNA with DNA-based
       fluorescence nanobarcodes
<303> JOURNAL: Nature Biotechnology
<304> VOLUME: 23
<306> PAGES: 885-889
<307> DATE: 2005
```

```
<300> PUBLICATION INFORMATION:
<301> AUTHORS: Y. Li, Y. D. Tseng, S. Y. Kwon, L. d'Espaux, J. S. Bunch,
      P. L. McEuen, D. Luo
<302> TITLE: Controlled assembly of dendrimer-like DNA
<303> JOURNAL: Nature Materials
<304> VOLUME: 3
<306> PAGES: 38-42
<307> DATE: 2004

<400> SEQUENCE: 1
ttgctggatc cgcatgattc gccgtaag                                          28

<210> SEQ ID NO 2
<211> LENGTH: 25
<212> TYPE: DNA
<213> ORGANISM: artificial sequence
<220> FEATURE:
<223> OTHER INFORMATION: synthetic

<400> SEQUENCE: 2
cttacgcgaa tgaccgaatc agcct                                             25

<210> SEQ ID NO 3
<211> LENGTH: 28
<212> TYPE: DNA
<213> ORGANISM: artificial sequence
<220> FEATURE:
<223> OTHER INFORMATION: synthetic
<300> PUBLICATION INFORMATION:
<301> AUTHORS: Y. Li, Y.T.H. Cu, D. Luo
<302> TITLE: Multiplexed detection of pathogen DNA with DNA-based
      fluorescence nanobarcodes
<303> JOURNAL: Nature Biotechnology
<304> VOLUME: 23
<306> PAGES: 885-889
<307> DATE: 2005
<300> PUBLICATION INFORMATION:
<301> AUTHORS: Y. Li, Y. D. Tseng, S. Y. Kwon, L. d'Espaux, J. S. Bunch,
      P. L. McEuen, D. Luo
<302> TITLE: Controlled assembly of dendrimer-like DNA
<303> JOURNAL: Nature Materials
<304> VOLUME: 3
<306> PAGES: 38-42
<307> DATE: 2004

<400> SEQUENCE: 3
cyaggctgat tcggttcatg cggatcca                                          28
```

ANTIMICROBIAL HYDROGELS, METHODS OF PREPARATION THEREOF, AND ARTICLES THEREFROM

CROSS REFERENCE TO RELATED APPLICATIONS

This application claims the benefit of U.S. Provisional application No. 61/451,491 entitled "BIODEGRADABLE ANTIMICROBIAL HYDROGELS FORMED IN SITU FROM POLYCARBONATE AND POLY(ETHYLENE GLYCOL) VIA MICHAEL ADDITION" filed on Mar. 10, 2011, herein incorporated by reference in its entirety.

PARTIES TO A JOINT RESEARCH AGREEMENT

This invention was made under a joint research agreement between International Business Machines Corporation and the Agency For Science, Technology and Research.

Incorporated herein by reference is the Sequence Listing contained in the text file named 13213555_Sequence_Listing_19Apr.2013_ST25.txt created Apr. 19, 2013 having a size of 2 kilobytes.

BACKGROUND

This invention relates to antimicrobial hydrogels and methods of preparation thereof, and more specifically, to crosslinked hydrogel networks having pendant cationic block copolymers.

Microbial adhesion onto biomaterial implants and subsequent formation of biofilm can lead to failure of the implanted devices in terms of function and structure. Among all infections found in hospitals, catheter-associated bacterial infections are the most common due to the extensive use of catheters in medical care. A 10% to 30% infection rate is reported for more than 30 million implanted urinary catheters each year in the US. Catheter infections lead to increased morbidity and mortality (up to 5% of infections) and create a multi-billion dollar burden on the US health care system because of prolonged hospital stays and increased medical costs.

In response, physically immobilizing or covalently linking antibiotics on the surfaces of catheters has been attempted to address this problem. For example, the antibiotics-coated urethral catheters have been shown to be effective in preventing catheter-associated infections in the case of short-term catheterization. However, drug resistance is easily developed with conventional antibiotics, and drug-resistant bacteria are not susceptible to the treatment of the antibiotics. An alternative approach involves coating the inner surfaces of the catheters with hydrogels or films impregnated with antimicrobial agents such as antibiotics, silver ions or iodine. Nevertheless, these antimicrobial agents and silver are highly toxic and the protection is short-lived due to the difficulty in controlling the diffusion rate.

Recently, attention has been directed to cationic polymer coatings. This is because cationic polymer coatings interact with microbial walls/membranes based on electrostatic interactions instead of targeting their metabolic activity, which is associated with the resistance. Moreover, antimicrobial polymer coatings kill or at least inhibit bacteria through active contact rather than gradually releasing toxic antimicrobial agents into the surrounding area. For example, alkylated polyvinylpyridines and alkylated polyethylenimines have been immobilized and reported to be lethal to *Staphylococcus aureus* (*S. aureus*), *Staphylococcus epidermidis* (*S. epidermidis*), *Pseudomonas aeruginosa* (*P. aeruginosa*) and *Escherichia coli* (*E. coli*). However, most antimicrobial polymers reported in the literature are non-biodegradable and non-biocompatible. Chitosan and chitosan-derivatized hydrogels/films, which are non-toxic and biodegradable, have been reported to be resistant to biofilm formation by bacteria and yeast. Nevertheless, the antimicrobial activity is not of a broad spectrum and is largely affected by the pH of the surrounding solutions. In addition, the antimicrobial agents can easily adsorb proteins, and the dead microorganisms remain on the coatings, which can trigger an immune response and inflammation, blocking the antimicrobial functional groups. More recently, UV cross-linked hydrogel made from a hydrophobic alkyl-modified quaternized ammonium chitosan grafted with poly(ethylene glycol) (PEG) was reported to have antimicrobial efficacy against Gram-positive and Gram-negative bacteria as well as fungi. However, the quality and molecular weight of chitosan vary from batch to batch, and chitosan can cause immunogenicity. Moreover, photopolymerization often produces materials with poorly controlled structure due to radical chemistry.

Therefore, an urgent need exists to develop a biodegradable and biocompatible synthetic film forming material that has strong antimicrobial activity against both Gram-positive and Gram-negative bacteria, non-fouling properties, and can be easily applied in situ.

SUMMARY

Accordingly, a covalently crosslinked hydrogel is disclosed comprising:
  three or more divalent poly(alkylene oxide) chains P' covalently linked at respective first end units to a branched first core group C';
  three or more divalent poly(alkylene oxide) chains P''' covalently linked at respective first end units to a branched second core group C''', the chains P''' comprising respective second end units which are covalently linked to between 0% and 100% of respective second end units of chains P' by divalent linking groups L''; and
  at least one pendant cationic block copolymer chain A'-B' which comprises i) a divalent block A' comprising a poly(alkylene oxide) backbone chain having an end unit covalently linked to a second end unit of one of the chains P' by a divalent linking group L', and ii) a monovalent block B' comprising a first repeat unit, the first repeat unit comprising a backbone carbonate group and a cationic side chain group.

A method of forming the above hydrogel is disclosed, comprising:
  combining i) a first crosslinking agent $C'[—P'—F']_{t'}$, ii) a cationic nucleophilic block copolymer $N^a$-A'-B', iii) a base; and iv) a second crosslinking agent $C'''[—P'''—N^b]_{u'}$, thereby forming a hydrogel precursor mixture; and
  allowing and/or inducing the hydrogel precursor mixture to crosslink, thereby forming the hydrogel;
  wherein
  i) $C'[—P'—F']_{t'}$ comprises $t' \geq 3$ independent divalent poly(alkylene oxide) chains P' comprising respective first end units covalently linked to a branched first core group C' and respective electrophilic second end units F',
  ii) $N^a$-A'-B' is formed by organocatalyzed ring opening polymerization, and $N^a$-A'-B' comprises a) a divalent block A' comprising a poly(alkylene oxide) backbone linked to a nucleophilic end unit $N^a$ capable of reacting with F' to form a divalent linking group L', and b)

a monovalent cationic block B' comprising a first repeat unit, the first repeat unit comprising a backbone carbonate group and a cationic side chain group, and iii) $C'[—P'''—N^b]_{u'}$ comprises $u' \geqq 3$ independent divalent poly(alkylene oxide) chains P''' comprising respective first end units covalently linked to a second branched core group C'' and respective nucleophilic second end units $N^b$, wherein each of the second end units is capable of reacting with F' to form a divalent linking group L''.

Also disclosed is a covalently crosslinked hydrogel of formula (1):

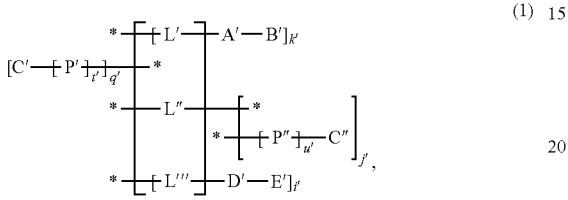

(1)

wherein starred bonds indicate attachment points,

A'-B' is a pendant cationic block copolymer comprising i) a divalent block A' comprising a poly(alkylene oxide) backbone and ii) a monovalent block B' comprising a first repeat unit, the first repeat unit comprising a backbone carbonate group and a cationic side chain group, D'-E' is an optional pendant non-charged amphiphilic block copolymer comprising i) a block D' comprising a poly(alkylene oxide) backbone and a hydrophobic block E', each C' is an independent branched first core group comprising at least one carbon and having a valency of t', t' is an integer greater than or equal to 3, each C'' is an independent branched second core group comprising at least one carbon and having a valency of u', u' is an integer greater than or equal to 3, each P' is an independent divalent poly(alkylene oxide) chain, each P''' is an independent divalent poly(alkylene oxide) chain, each C' is linked to t' number of chains P', each C'' is linked to u' number of chains P''', each L' is an independent divalent linking group that covalently links a chain P' to a block A', each L'' is an independent divalent linking group that covalently links a chain P' to a chain P''', each L''' is an optional independent divalent linking group that covalently links a chain P' to a block D', q' is a number greater than 0 representing moles of C' in the hydrogel, j' is a number greater than 0 representing moles of C'' in the hydrogel, k' is a number greater than 0 representing moles of block copolymer A'-B' in the hydrogel, i' is a number greater than or equal to 0 representing moles of optional block copolymer D'-E' in the hydrogel, and between 0% and 100% of the chains P' are independently covalently linked to chains P'''.

Another method is disclosed, comprising:

forming a mixture comprising i) a first crosslinking agent $C'[—P'—F']_{t'}$ comprising $t' \geqq 3$ independent divalent poly(alkylene oxide) chains P' comprising respective first end units covalently linked to a branched first core group C' and respective electrophilic second end units F', ii) a cationic nucleophilic block copolymer $N^a$-A'-B' formed by organocatalyzed ring opening polymerization, $N^a$-A'-B' comprising a) a divalent block A' comprising a poly(alkylene oxide) backbone linked to a nucleophilic end unit $N^a$ capable of reacting with F' to form a divalent linking group L', and b) a monovalent cationic block B' comprising a first repeat unit, the first repeat unit comprising a backbone carbonate group and a cationic side chain group, iii) a base, and optionally iv) a nucleophilic non-charged amphiphilic block copolymer $N^c$-D'-E' formed by organocatalyzed ring opening polymerization, $N^c$-D'-E' comprising a) a divalent block D' comprising a poly(alkylene oxide) backbone chain having a nucleophilic end unit $N^c$ capable of reacting with F' to form a divalent linking group L''', and b) a monovalent hydrophobic block E';

agitating the mixture, thereby forming an adduct, wherein the adduct comprises unreacted electrophilic groups F';

forming a hydrogel precursor mixture comprising i) the adduct and a second crosslinking agent $C''[—P'''—N^b]_{u'}$ comprising $u' \geqq 3$ independent divalent poly(alkylene oxide) chains P''' comprising respective first end units covalently linked to a second branched core group C'' and respective nucleophilic second end units $N^b$ capable of reacting with F' to form a divalent linking group L'';

disposing the hydrogel precursor mixture on a surface of a substrate, thereby forming a hydrogel precursor layer disposed on the surface; and allowing and/or inducing the hydrogel precursor layer to crosslink, thereby forming an antimicrobial layer comprising a covalently crosslinked cationic hydrogel disposed on the surface of the substrate.

Another covalently crosslinked hydrogel is disclosed of formula (1a):

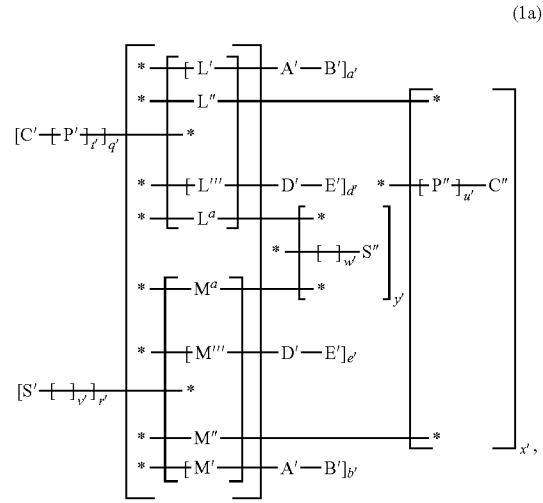

(1a)

wherein starred bonds indicate attachment points,

A'-B' is a pendant cationic block copolymer comprising i) a divalent block A' comprising a poly(alkylene oxide) backbone and ii) a monovalent cationic block B' comprising a first repeat unit, the first repeat unit comprising a backbone carbonate group and a cationic side chain group, D'-E' is a pendant non-charged amphiphilic block copolymer comprising i) a block D' comprising a poly(alkylene oxide) backbone and a hydrophobic block E', each C' is an independent branched first core group comprising at least one carbon and having a valency of t', t' is an integer greater than or equal to 3, each C'' is an independent branched second core group comprising at least one carbon and having a valency of u', u' is an integer greater than or equal to 3, each P' is an independent divalent poly(alkylene oxide) chain, each P''' is an independent divalent poly(alkylene oxide) chain, each L' is an independent divalent linking group that covalently links a chain P' to a block A', each L'' is an independent divalent linking group that covalently links a chain P' to a chain P''', each L''' is an independent divalent linking group that covalently links a chain P' to a block D', each S' is an independent non-polymeric core group comprising at least one carbon and having a valency of v', wherein v' is a positive integer greater than or equal to 2, each S'' is an independent non-polymeric core group comprising at least one carbon and having a valency of w', wherein w' is a positive integer greater than or equal to 2, each $L^a$ is an independent divalent linking group that covalently links a S'' group to a chain P', each $M^a$ is an independent divalent linking group that covalently links a S'' group to a S' group, each M' is an independent divalent linking group that covalently links a S' group to a block A' of block copolymer A'-B', M'' is an independent divalent linking group that covalently links a S' group to a chain P''', M''' is an independent divalent linking group that covalently links a S' group to a block D' of block copolymer D'-E', a' is a number greater than 0 representing moles of A'-B' linked to chains P' in the hydrogel, b' is a number greater than or equal to 0 representing moles of A'-B' linked to S' in the hydrogel, d' is a number greater than or equal to 0 representing moles of D'-E' linked to chains P' in the hydrogel, e' is a number greater than or equal to 0 representing moles of D'-E' linked to S' in the hydrogel, q' is a number greater than 0 representing moles of C' in the hydrogel, x' is a number greater than 0 representing moles of C'' in the hydrogel, y' is a number greater than or equal to 0 representing moles of S'' in the hydrogel, r' is a number greater than or equal to 0 representing moles of S' in the hydrogel, each C' is linked to t' number of chains P', each C'' is linked to u' number of chains P''', each S' group is linked to v' number of linking groups independently selected from the group consisting of M', M'', M''', and $M^a$, each S'' group is linked to w' number of linking groups independently selected from the group consisting of $L^a$ and $M^a$, and between 0% and 100% of the chains P' are independently covalently linked to chains P''' in the hydrogel.

Another method is disclosed, comprising:

combining i) a first crosslinking agent $C'[—P'—F']_{t'}$, optionally ii) an electrophilic non-polymeric crosslinking agent, $S'[—F'']_{v'}$, iii) a cationic nucleophilic block copolymer $N^a$-A'-B', iv) a base; optionally v) a nucleophilic non-charged amphiphilic block copolymer $N^c$-D'-E', vi) a second crosslinking agent $C''[—P'''—N^b]_{u'}$, and optionally vii) a nucleophilic non-polymeric crosslinking agent $S''[—N^d]_{w'}$, thereby forming a hydrogel precursor mixture; and allowing and/or inducing the hydrogel precursor mixture to crosslink, thereby forming a covalently crosslinked hydrogel;

wherein i) $C'[—P'—F']_{t'}$ comprises $t' \geq 3$ independent divalent poly(alkylene oxide) chains P' comprising respective first end units covalently linked to a branched first core group C' and respective electrophilic second end units F', ii) $S'[—F'']_{v'}$ comprises $v' \geq 2$ independent electrophilic groups F'' and a non-polymeric core group S' comprising at least one carbon, iii) $N^a$-A'-B' is formed by organocatalyzed ring opening polymerization, and $N^a$-A'-B' comprises a) a divalent block A' comprising a poly(alkylene oxide) backbone linked to a nucleophilic end unit $N^a$ capable of reacting with F' to form a divalent linking group L' and/or reacting with F'' to form a divalent linking group M', and b) a monovalent cationic block B' comprising a first repeat unit, the first repeat unit comprising a backbone carbonate group and a cationic side chain group, iv) $N^c$-D'-E' is formed by organocatalyzed ring opening polymerization, and $N^c$-D'-E' comprises a) a divalent block D' comprising a poly(alkylene oxide) backbone chain having an end unit $N^c$ capable of reacting with F' to form a divalent linking group L''' and/or reacting with F'' to form divalent linking group M''', and b) a monovalent block E';

v) $C''[—P'''—N^b]_{u'}$ comprises $u' \geq 3$ independent divalent poly(alkylene oxide) chains P''' comprising respective first end units covalently linked to a second branched core group C'' and respective nucleophilic second end units $N^b$, wherein each of the second end units is capable of reacting with F' to form a divalent linking group L'' and/or reacting with F'' to form a divalent linking group M'', and vi) $S''[—N^d]_{w'}$ comprises $w' \geq 2$ nucleophilic groups $N^d$ and a non-polymeric core group S'' comprising at least one carbon, wherein $N^d$ is capable of reacting with F' to form a divalent linking group $L^a$ and/or reacting with F'' to form a divalent linking group $M^a$.

Another method is disclosed, comprising contacting a microbe with the above-described covalently crosslinked hydrogel, thereby killing the microbe.

Compositions are disclosed comprising any of the above-described hydrogels and a gene and/or a drug.

Articles are disclosed comprising any of the above-described covalently crosslinked hydrogels disposed on a surface of a medical device.

The above-described and other features and advantages of the present invention will be appreciated and understood by those skilled in the art from the following detailed description, drawings, and appended claims.

against *Staphylococcus aureus* (*S. aureus*) over a 48 hour incubation period. Phosphate buffered saline (PBS), triethanolamine (TEOA), tryptic soy broth (TSB), and non-charged PEG-APC-0 (comparative Example 11, Table 19) were used as controls. A lower optical density (OD) at 600 nm indicates more effective growth inhibition.

Figure 1A:
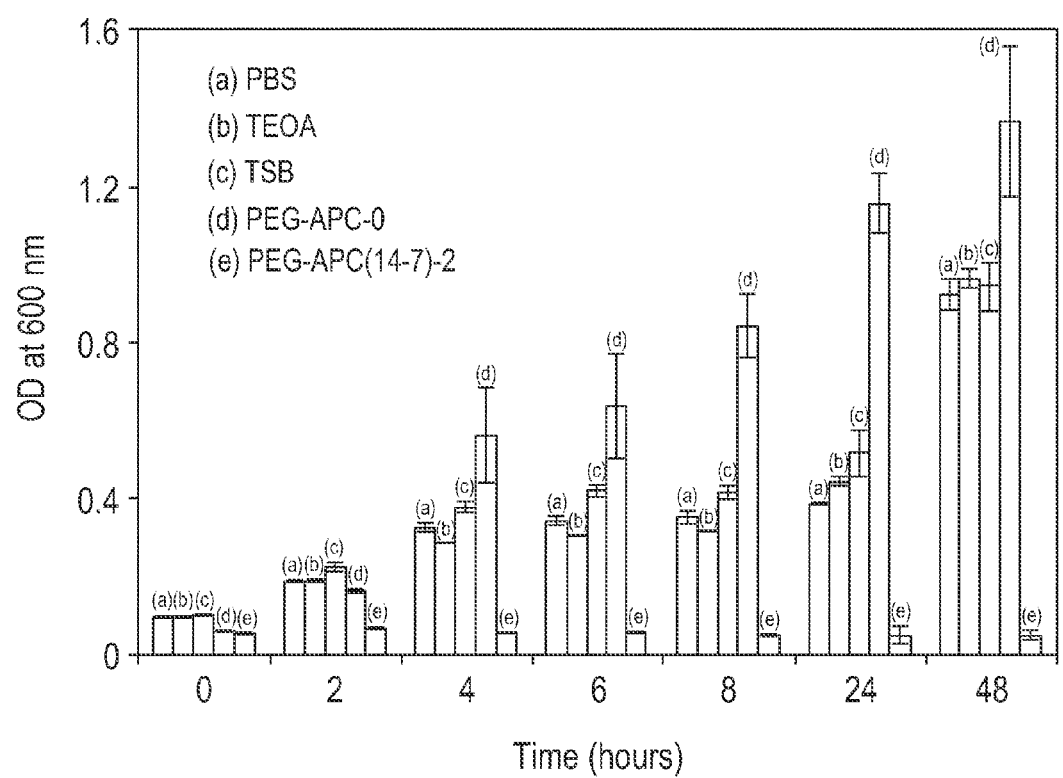
FIG. 1A is a bar chart showing growth inhibition of cationic hydrogel PEG-APC(14-7)-2 (Example 13, Table 19)
Figure 1B:
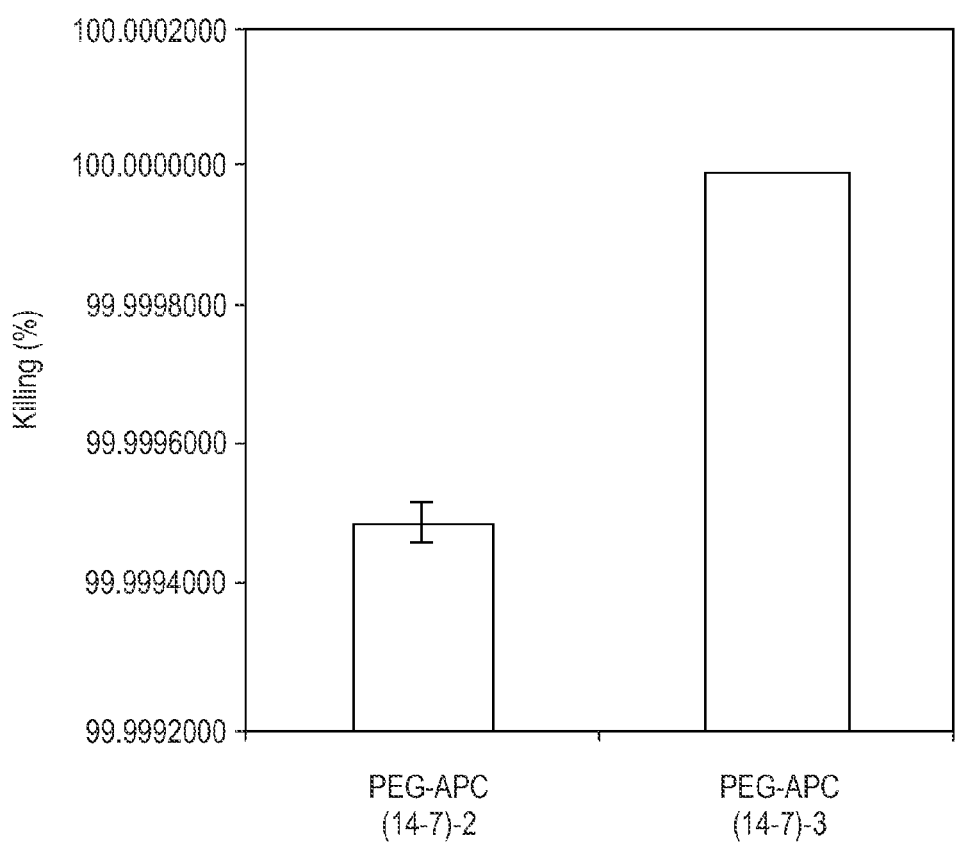

FIG. 1B is a bar chart showing killing efficiency (in percent) of cationic hydrogels PEG-APC(14-7)-2 and PEG-APC (14-7)-3 against *S. aureus* over 8 hours. Non-charged hydrogel PEG-APC-0 was the control, and its killing efficiency was defined as 0%. The killing efficiency of other gels was calculated relative to that of PEG-APC-0 gel. The formula for calculating killing efficiency is: 100%×[CFU on the PEG-APC-0 gel-CFU on the sample gel]/CFU on the PEG-APC-0 gel, where CFU stands for colony forming units.

Figure 1C:
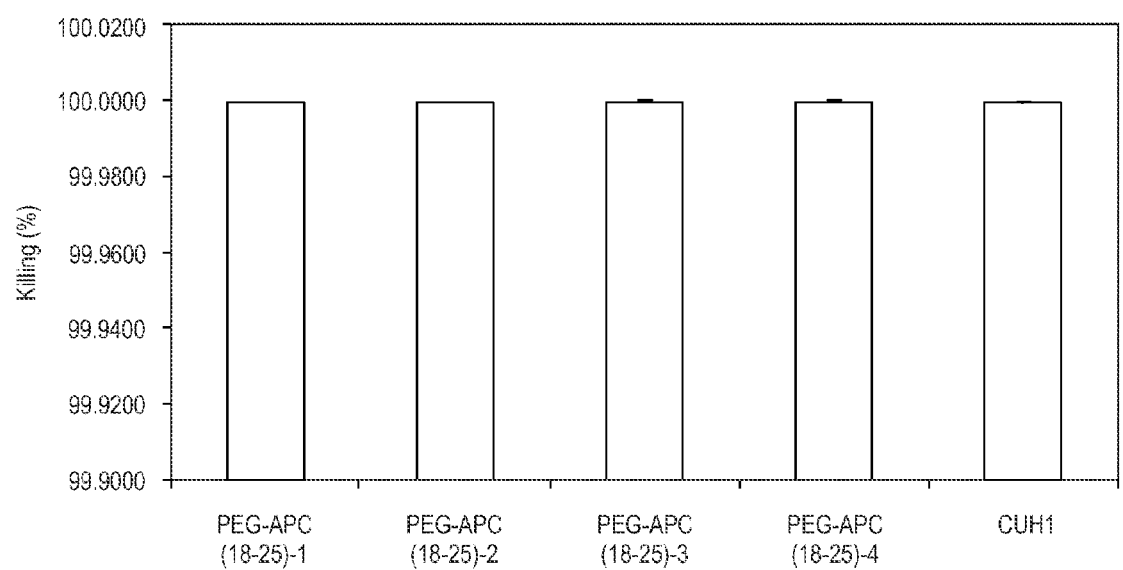

FIG. 1C is a bar chart showing killing efficiency (in percent) against *S. aureus* over 8 hours of cationic hydrogels PEG-APC(18-25)-1, PEG-APC(18-25)-2, PEG-APC(18-25)-3 and PEG-APC(18-25)-4, and cationic urea-containing hydrogel CUH1. Non-charged hydrogel PEG-APC-0 was the control, and its killing efficiency was defined as 0%. The killing efficiency of other gels was calculated relative to that of PEG-APC-0 gel. The killing efficiency was calculated using the formula described above for FIG. 1B.

Figure 2A:
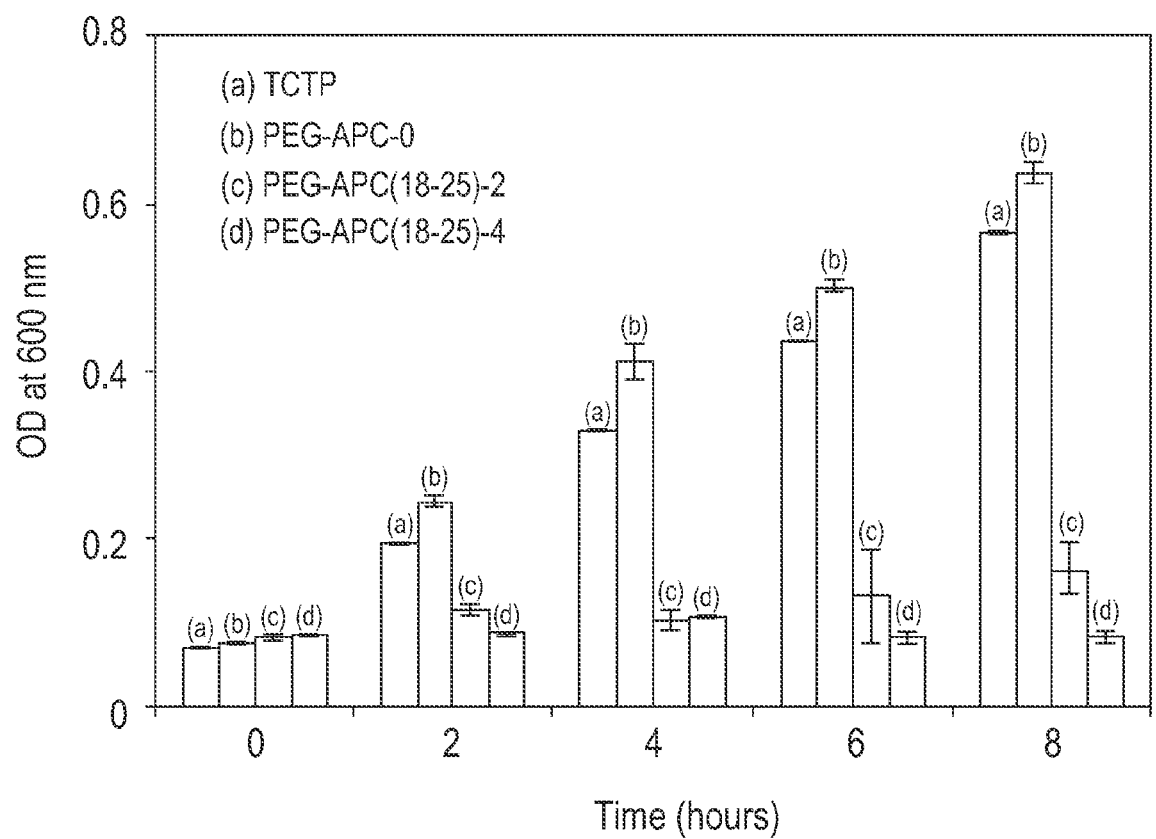

FIG. 2A is a bar chart comparing the growth inhibition of cationic hydrogels PEG-APC(18-25)-2 (Example 23, Table 19) and PEG-APC(18-25)-4 (Example 25, Table 19) against *Escherichia coli* (*E. coli*) over an 8 hour incubation period. TCTP plates (MicroWell™ treated polystyrene tissue culture plates sold by Nunc and used as a control surface for cell growth) and non-charged hydrogel PEG-APC-0 (comparative Example 11, Table 19) were used as controls. The initial *E. coli* concentration was $2 \times 10^9$ CFU/dm$^2$. A lower optical density at 600 nm indicates more effective growth inhibition.

Figure 2B:
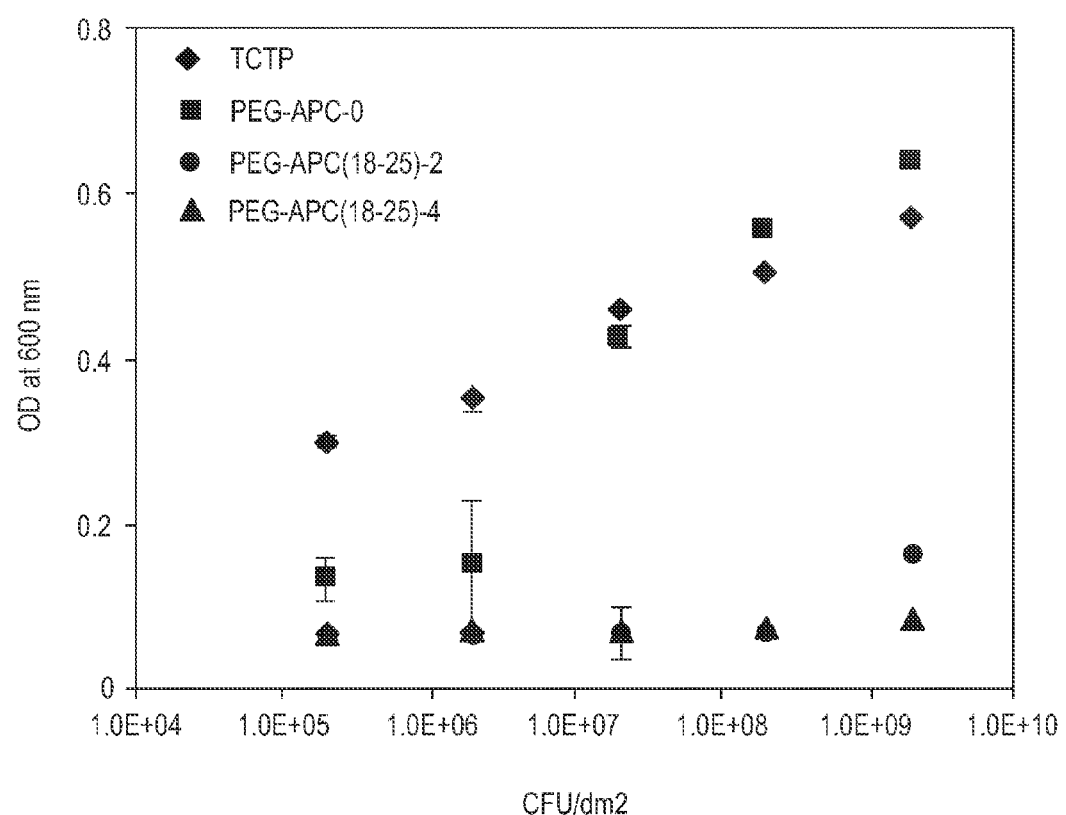

FIG. 2B is a scatter plot showing the growth inhibition of cationic hydrogels PEG-APC(18-25)-2 (Example 23, Table 19) and PEG-APC(18-25)-4 (Example 25, Table 19), TCTP plates, and non-charged hydrogel PEG-APC-0 (comparative Example 11, Table 19) against *E. coli* after 8 hours of incubation using different initial concentrations of *E. coli*. A lower optical density at 600 nm indicates more effective growth inhibition.

Figure 2C:
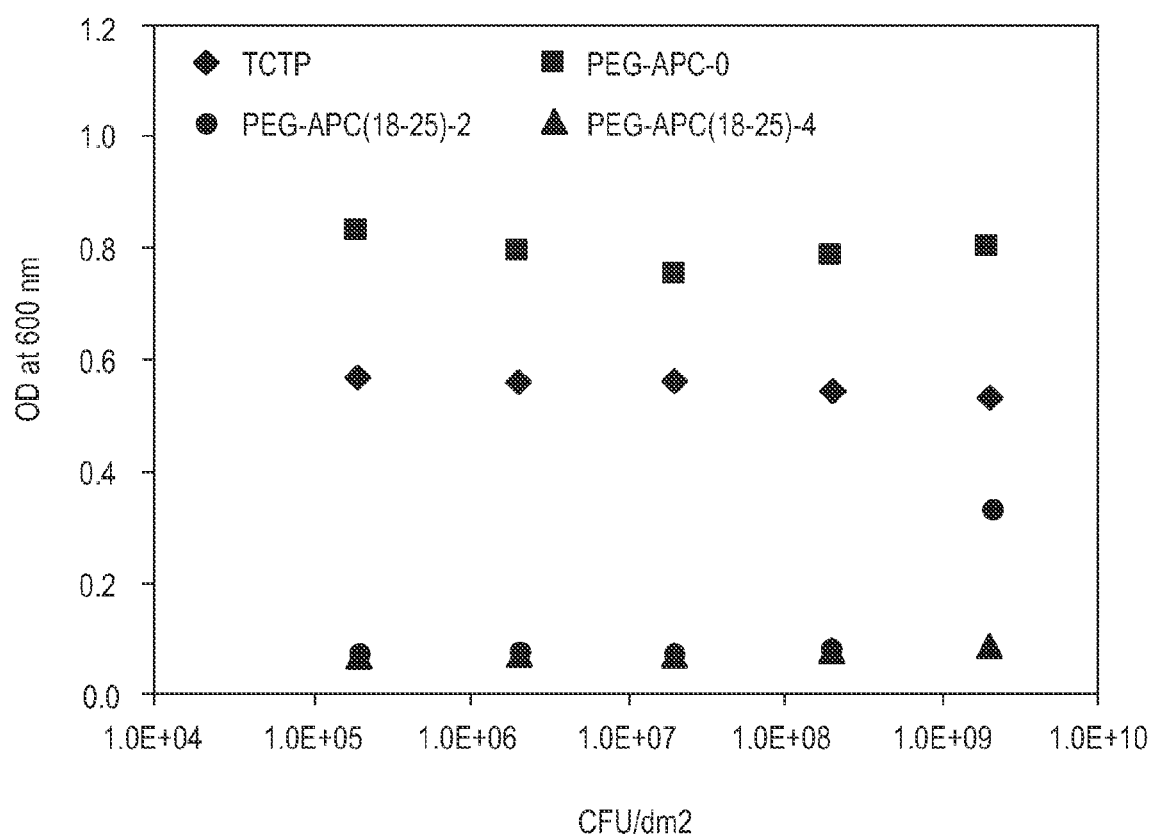

FIG. 2C is a scatter plot showing the growth inhibition of cationic hydrogels PEG-APC(18-25)-2 (Example 23, Table 19) and PEG-APC(18-25)-4 (Example 25, Table 19), TCTP plates, and non-charged hydrogel PEG-APC-0 (comparative Example 11, Table 19) against *E. coli* after 24 hours of incubation using different initial concentrations of *E. coli*. A lower optical density at 600 nm indicates more effective growth inhibition.

Figure 2D:
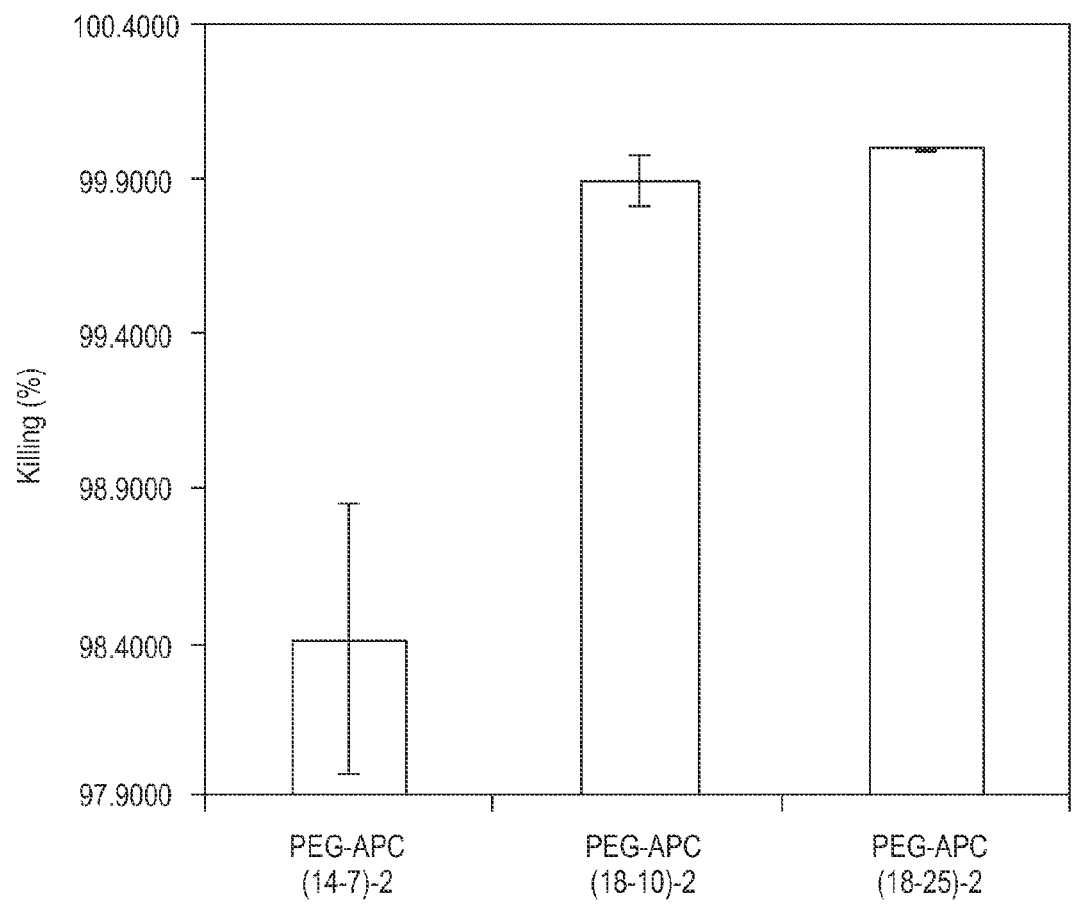

FIG. 2D is a bar chart showing killing efficiency (in percent) of cationic hydrogels PEG-APC(14-7)-2 (Example 13, Table 19), PEG-APC(18-10)-2 (Example 19, Table 19), and PEG-APC(18-25)-2 (Example 23, Table 19) against *E. coli* after 8 hours incubation. Non-charged hydrogel PEG-APC-0 (comparative Example 11, Table 19) was the control, and its killing efficiency was defined as 0%. The killing efficiency of other gels was calculated relative to that of PEG-APC-0 gel. The killing efficiency was calculated using the formula described above for FIG. 1B.

Figure 2E:
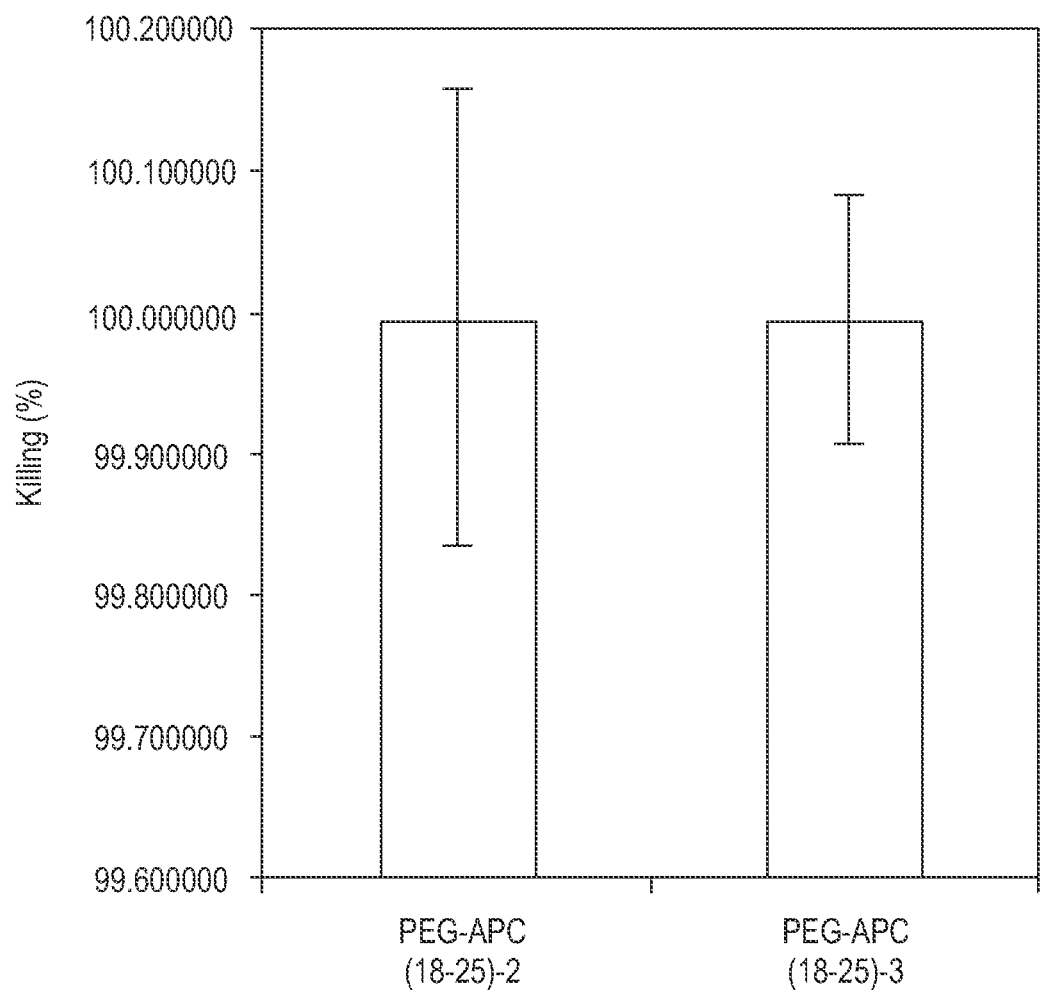

FIG. 2E is a bar chart showing killing efficiency (in percent) of cationic hydrogels PEG-APC(18-25)-2 (Example 23, Table 19) and PEG-APC(18-25)-3 (Example 24, Table 19) against *E. coli* over 8 hours. Non-charged hydrogel PEG-APC-0 (comparative Example 11, Table 19) was the control, and its killing efficiency was defined as 0%. The killing efficiency of other gels was calculated relative to that of PEG-APC-0 gel. The killing efficiency was calculated using the formula described above for FIG. 1B.

Figure 3A:
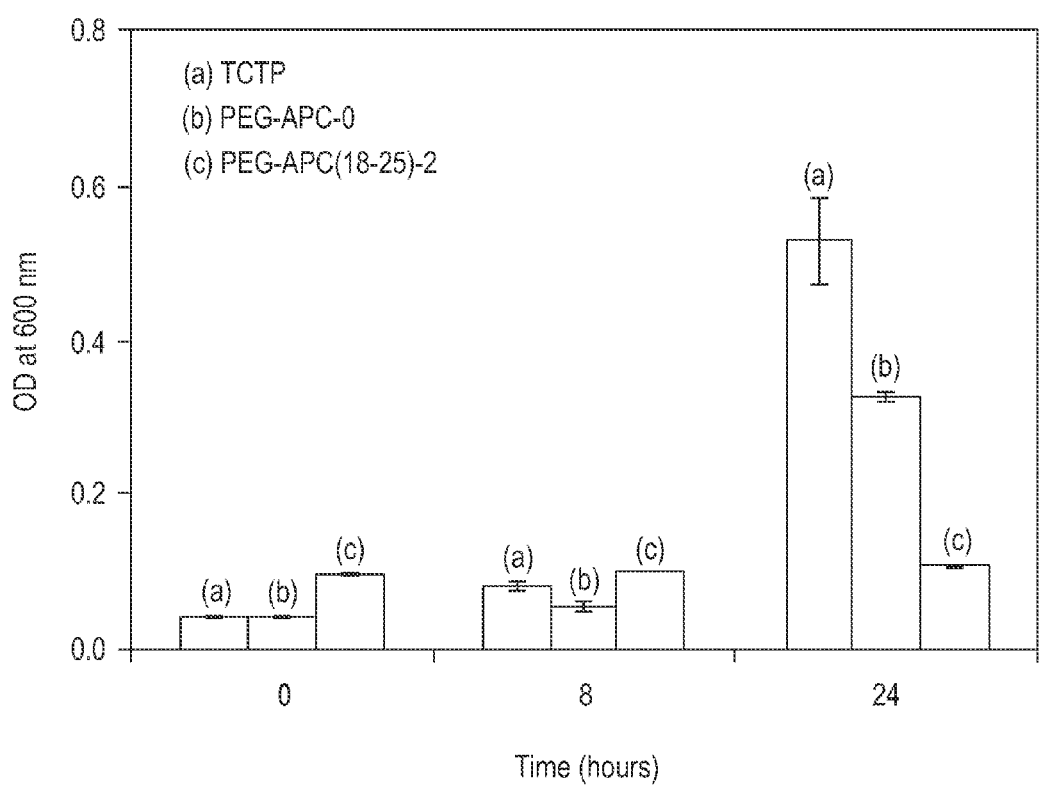

FIG. 3A is a bar chart showing growth inhibition effect of cationic hydrogel PEG-APC(18-25)-2 (Example 23, Table 19) after 24 hours against *Candida albicans* (*C. albicans*) using an initial cell concentration of 10$^8$ CFU/mL. Non-charged hydrogel PEG-APC-0 (comparative Example 11, Table 19) and TCTP plates were used as controls. A lower optical density at 600 nm indicates more effective growth inhibition.

Figure 3B:
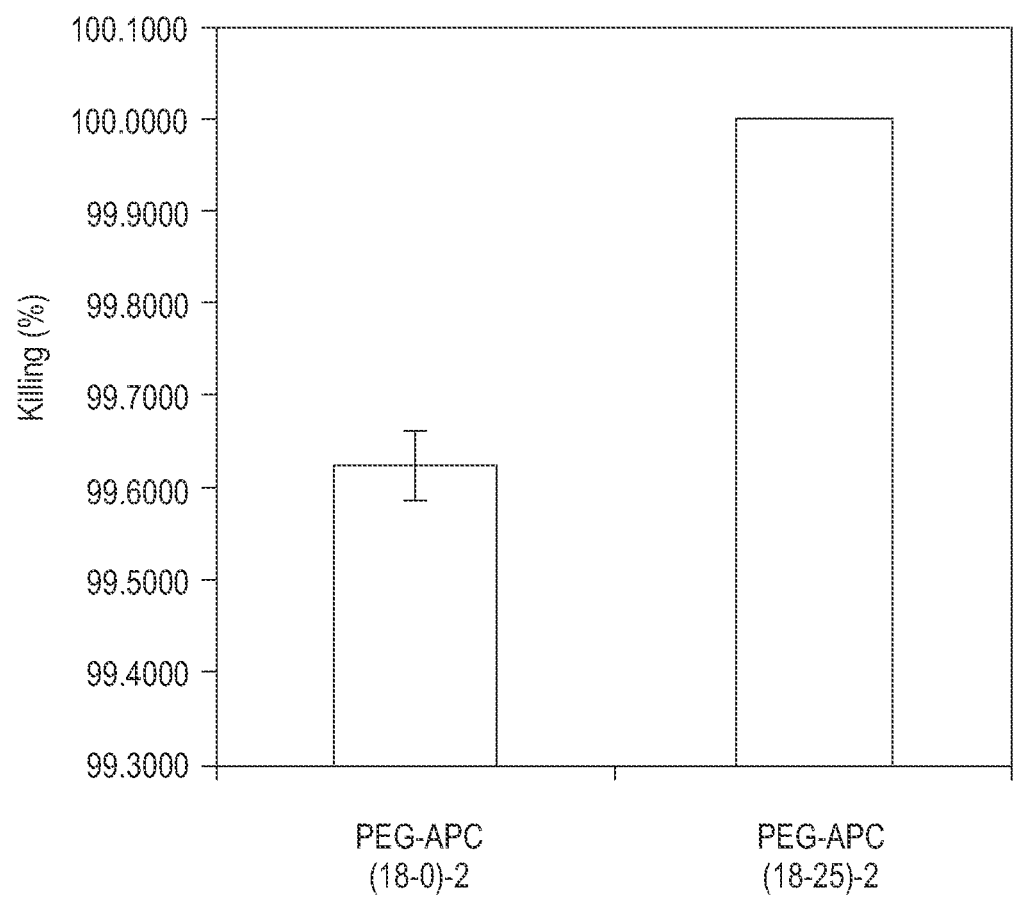

FIG. 3B is a bar chart showing killing efficiency of cationic hydrogels PEG-APC(18-0)-2 (Example 17, Table 19) and PEG-APC(18-25)-2 (Example 23, Table 19) against *C. albicans* after 24 hours of incubation. Non-charged hydrogel PEG-APC-0 (comparative Example 11, Table 19) was used as control, and its killing efficiency was defined as 0%. The killing efficiency of other gels was calculated relative to that of PEG-APC-0 gel. The killing efficiency was calculated using the formula described above for FIG. 1B.

Figure 4:
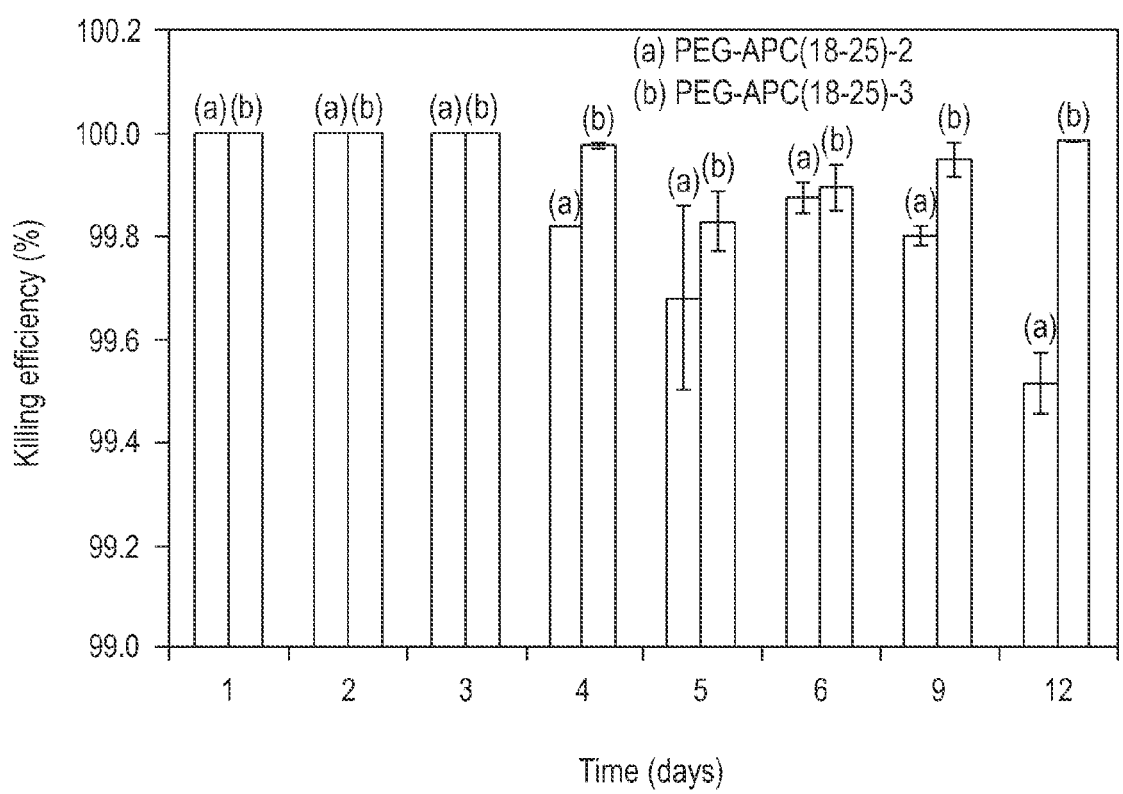

FIG. 4 is a bar chart showing long-term killing efficiency of cationic hydrogels PEG-APC(18-25)-2 (Example 23, Table 19) and PEG-APC(18-25)-3 (Example 24, Table 19) against *S. aureus* over a twelve day period. A bacterial concentration of $5.7 \times 10^6$ CFU/mL was applied daily. Non-charged hydrogel PEG-APC-0 (comparative Example 11, Table 19) was used as control, and its killing efficiency was defined as 0%. The killing efficiency of other gels was calculated relative to that of PEG-APC-0 gel. The killing efficiency was calculated using the formula described above for FIG. 1B.

Figure 5:
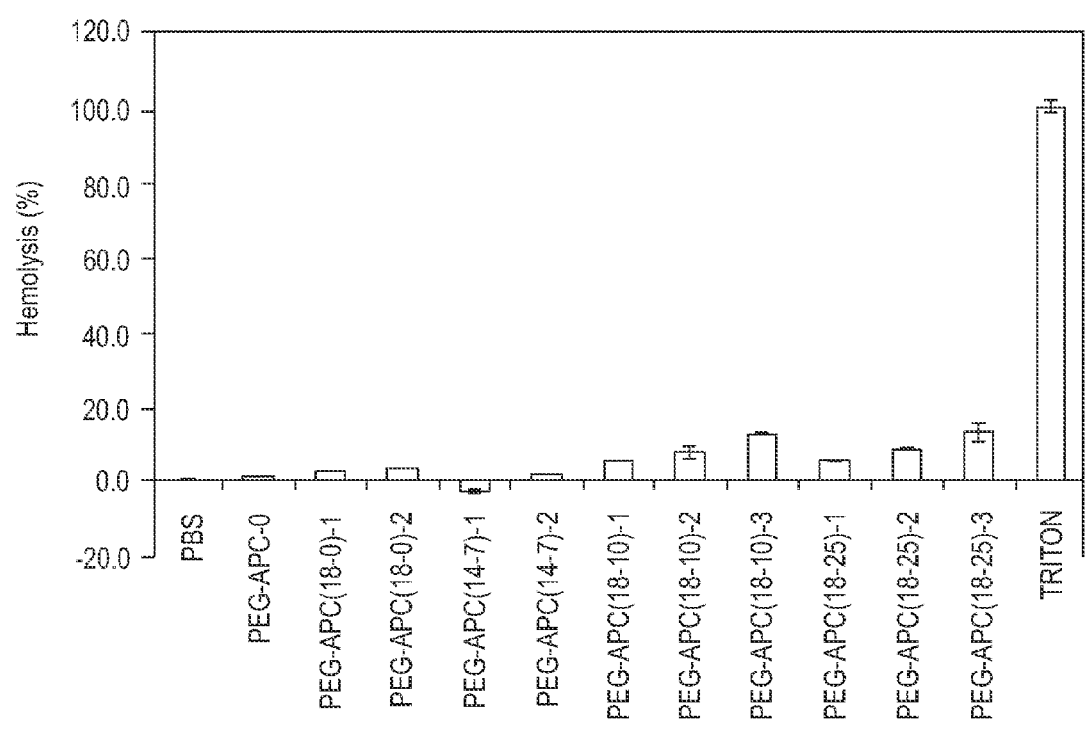

FIG. 5 is a bar chart showing hemolytic activity (as percent hemolysis) of various cationic hydrogels against rat blood cells. PBS, PEG-APC-0 (comparative Example 11, Table 19), and TRITON X-100 were used as controls. A lower percent indicates less hemolysis. The cationic hydrogels exhibited low hemolytic activity.

Figure 6I:
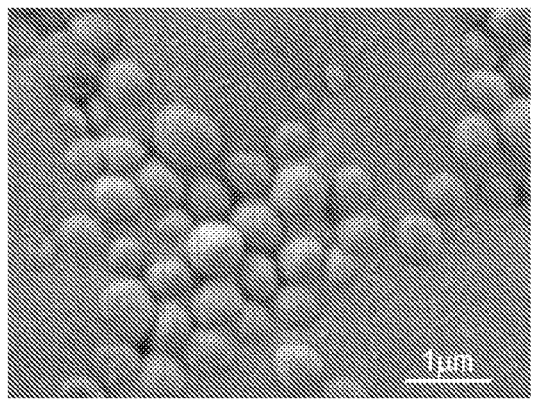
Figure 6J:
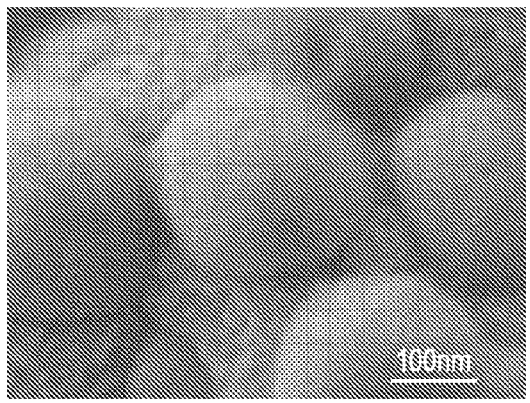

FIGS. 6A to 6J are SEM images of *S. aureus* after contact for 2 hours at 37° C. with cationic hydrogel PEG-APC(14-7)-2 (FIGS. 6A and 6B, Example 13, Table 19), non-charged hydrogel PEG-APC-0 (FIGS. 6C and 6D, comparative Example 11, Table 19), triethanolamine (TEOA) (FIGS. 6E and 6F), tryptic soy broth (TSB) (FIGS. 6G and 6H), and phosphate buffered saline (PBS) (FIGS. 6I and 6J). The left side images are at a magnification of 20,000. The right side images are at a magnification of 80,000.

FIGS. 7A to 7H are SEM images of *E. coli* after contact for 2 hours at 37° C. with cationic hydrogel PEG-APC(18-25)-2 (FIGS. 7A and 7B, Example 23, Table 19); cationic hydrogel PEG-APC(18-25)-4 (FIGS. 7C and 7D, Example 25, Table 19), non-charged hydrogel PEG-APC-0 (FIGS. 7E and 7F, comparative Example 11, Table 19), and TCTP plates (Nunc MicroWell™ Plates, Catalog No. 167008). (FIGS. 7G and 7H). The left side images are at a magnification of 20,000. The right side images are at a magnification of 80,000.

Figure 8:
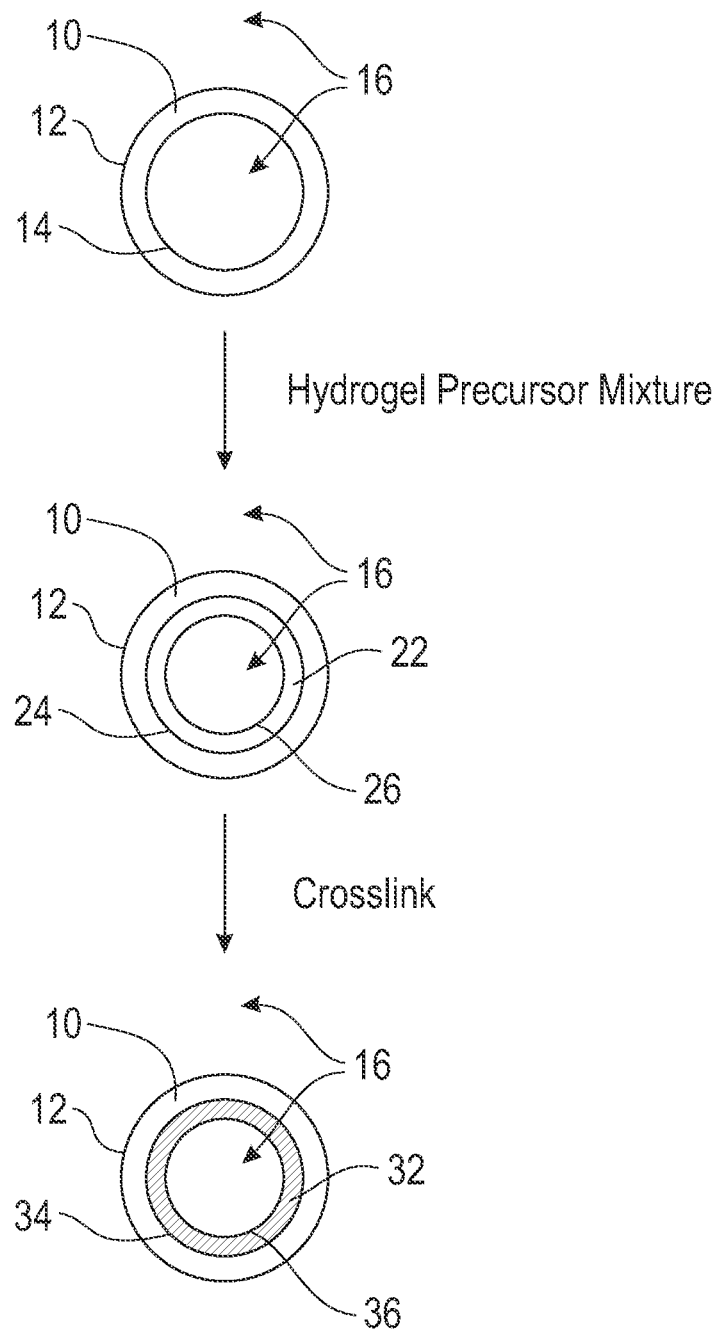

FIG. 8 is a series of layer diagrams demonstrating a method of forming a crosslinked hydrogel layer 32 disposed on the inside wall 14 of a tubular substrate 10.

Figure 9:
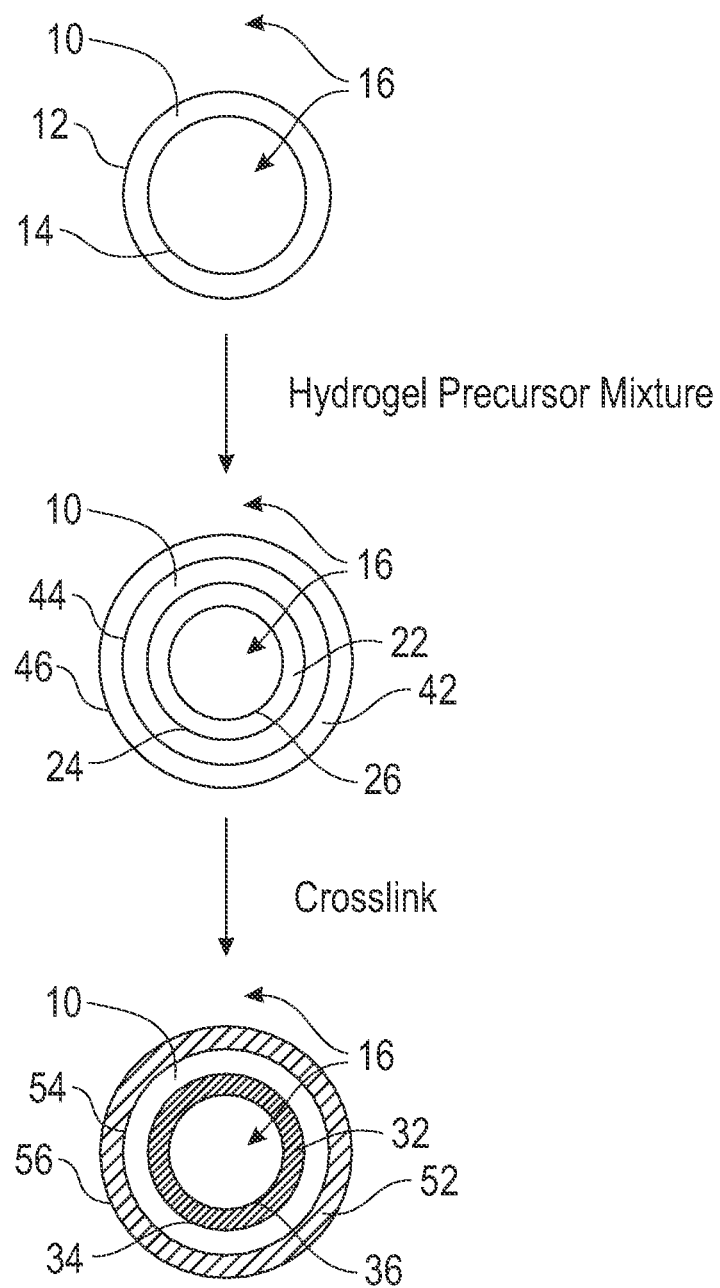

FIG. 9 is a series of layer diagrams demonstrating a method of forming crosslinked hydrogel layer 32 on the inside wall 14 of tubular substrate 10, and crosslinked hydrogel layer 52 on outside wall 12 of tubular substrate 10.

Figure 10A:
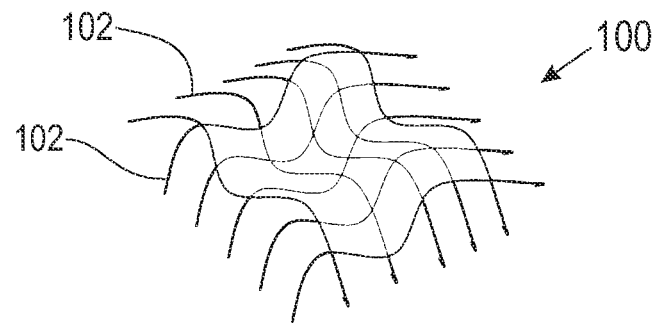

FIG. 10A is an illustration of a woven substrate 100 comprising threads 102.

Figure 10B:
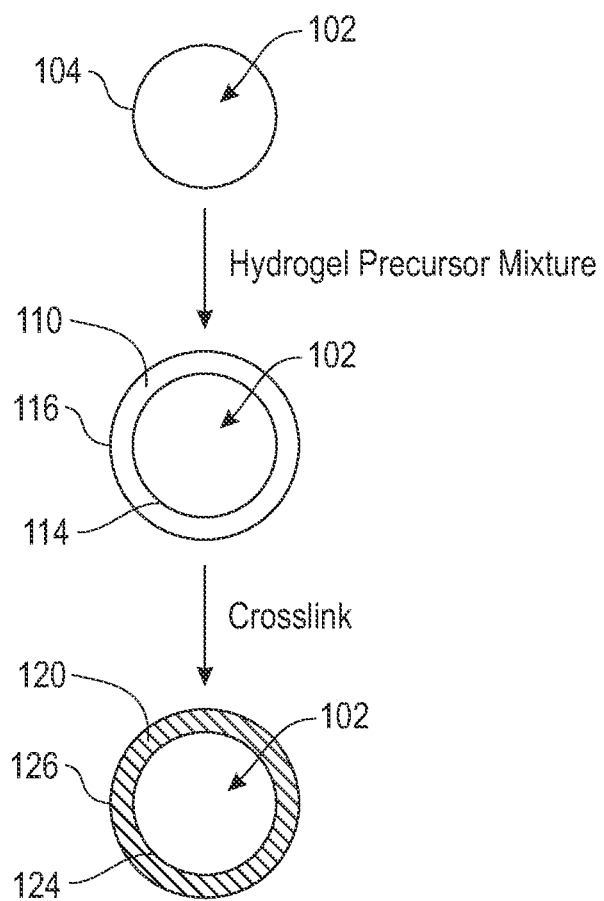

FIG. 10B is a series of layer diagrams illustrating a method of forming a crosslinked hydrogel layer 120 on a thread 102 of woven substrate 100 (FIG. 10A).

Figure 11:
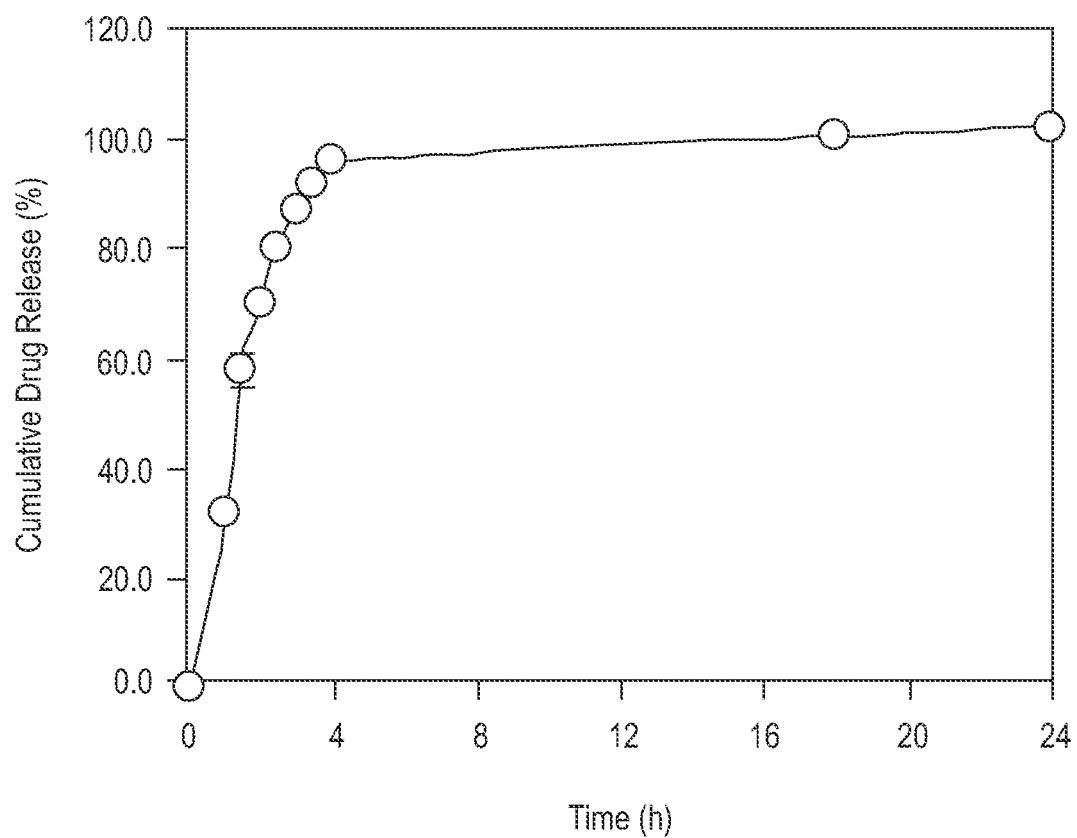

FIG. 11 is a graph showing the release profile of a drug diclofenac sodium salt (DCF) from DCF-loaded hydrogel (Example 27) at 37° C. in phosphate buffered saline (PBS). The crosslinked hydrogel was the same as PEG-APC(18-25)-2 of Example 23.

DETAILED DESCRIPTION

The invention is based on the discovery that covalently crosslinked hydrogels comprising a pendant cationic block copolymer can be effective antimicrobial agents against Gram positive microbes such as *Staphylococcus aureus* (*S. aureus*) and *Candida albicans* (*C. albicans*), and/or Gram negative microbes such as *Escherichia coli* (*E. coli*). By comparison, the corresponding free cationic block copolymer (i.e., cationic block copolymer that is not covalently bound to a hydrogel) and non-charged hydrogels, which comprise a non-charged pendant block copolymer or have no pendant block copolymer, have comparatively weak or ineffectual antimicrobial properties against particularly Gram negative microbes when tested under otherwise identical conditions. In an embodiment, the cationic crosslinked hydrogels are toxic to a Gram-negative microbe and a Gram-positive microbe selected from the group consisting of bacteria, fungi, yeasts, and combinations thereof. Preferably, the pendant cationic block copolymer comprises a repeat unit having a backbone carbonate and/or backbone ester group. Preferably, the cationic crosslinked hydrogels are also biodegradable and/or biocompatible.

The covalently crosslinked hydrogel network is preferably formed by the reaction of i) a nucleophilic cationic block copolymer $N^a$-A'-B' bearing a side chain quaternary amine group, ii) an electrophilic polymeric crosslinking agent $C'[-P'-F']_{t'}$, and iii) a nucleophilic polymeric crosslinking agent $C''[-P''-N^b]_{u'}$. The hydrogel preparation can also optionally include iv) a nucleophilic amphiphilic non-charged block copolymer $N^c$-D'-E', v) an electrophilic non-polymeric crosslinking agent $S'[-F'']_{v'}$, and/or vi) a nucleophilic non-polymeric crosslinking agent $S''[-N^d]_{w'}$. F' and F'' are electrophilic groups, and $N^a$, $N^b$, $N^c$ and $N^d$ are nucleophilic groups, which can react to form linking groups, thereby forming the covalently crosslinked network. Other structural details of the foregoing materials are described further below.

The nucleophilic cationic block copolymer $N^a$-A'-B' and the optional nucleophilic amphiphilic non-charged block copolymer $N^c$-D'-E' are preferably prepared by ring opening polymerization (ROP) of cyclic carbonyl monomers. The ROP is preferably initiated by a hydrophilic nucleophilic polymeric initiator.

The hydrogel-forming reaction mixture can optionally also include a gene and/or a drug. The gene and/or drug can be occluded reversibly or non-reversibly within the network. A reversibly occluded gene/and or drug can be suitable for use in a controlled release application.

The pendant cationic block copolymer of the hydrogel can have a net positive charge resulting from cationic groups that are covalently bound to the block copolymer, or a mixture of cationic groups and anionic groups that are covalently bound to the block copolymer. Preferably, the cationic block polymer contains no anionic groups that are covalently bound to the block polymer before contact with a cell. Exemplary cationic groups include protonated primary amine groups, protonated secondary amine groups, protonated tertiary amine groups, quaternary amine groups (i.e., nitrogen bonded to four carbons), sulfonium groups (i.e., sulfur bonded to three carbons), and phosphonium groups (i.e., phosphorous bonded to four carbons). The cationic polymer can comprise a mixture of the foregoing cationic functional groups. In an embodiment, the pendant cationic block copolymer comprises a side chain quaternary amine group.

Herein, the term "hydrogel" means a covalently crosslinked hydrogel. A hydrogel can have the form of a dry solid or a water swollen gel (e.g., a dry crosslinked film layer or a water swollen crosslinked film layer).

A "hydrogel precursor mixture" refers to a mixture whose components can react to form a hydrogel. A "hydrogel precursor layer" refers to a layer that is disposed on a surface of a substrate and contains components capable of reacting to form a hydrogel.

The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

A "biocompatible" material is defined herein as a material capable of performing with an appropriate host response in a specific application.

Herein, a composition suitable as an antimicrobial agent comprises at least a cationic hydrogel. The composition can further comprise water and/or a biologically active material. A method comprises contacting a microbe with the composition in the form of a dry powder or an aqueous gel, thereby killing the microbe. The composition can be in the form of a layer disposed on a surface of a substrate, wherein the layer is an effective antimicrobial agent against at least a Gram-positive microbe. The substrate can be an article (e.g., bandages, gauze, catheters, and medical instruments) used for a medical purpose that makes contact with animal tissue including wound tissue.

Hydrogels that comprise a biologically active material that is not covalently bound to the hydrogel network are referred to herein as loaded hydrogels. Biologically active substances include cells, biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing. The loaded hydrogels can have two or more independent biological functions (e.g., antimicrobial function, gene and/or drug delivery function, cell recognition function, artificial skin function, diagnostic enhancement function, etc.).

Herein "biologically active" means the referenced material can alter the chemical structure and/or activity of a cell in a desirable manner, can selectively alter the chemical structure and/or activity of a cell type relative to another cell type in a desirable manner, and/or provide a medical diagnostic function such as image enhancement. As an example, one desirable change in a chemical structure can be the incorporation of a gene into the DNA of the cell. A desirable change in activity can be the expression of the transfected gene. Another change in cell activity can be the induced production of a desired hormone or enzyme. Alternatively, a desirable change in activity can be the selective death of one cell type over another cell type. No limitation is placed on the relative change in cellular activity caused by the biologically active substance, providing the change is desirable and useful. Moreover, no limitation is placed on the biologically active substance, providing the biologically active substance induces a useful cellular response when released from the loaded hydrogel.

The hydrogels can comprise a non-stereospecific and/or stereospecific moiety. A stereospecific moiety i) has a non-superposable mirror image and ii) comprises one or more asymmetric tetravalent carbons (i.e., tetrahedral $sp^3$ carbons). Each asymmetric tetravalent carbon is assigned an R or S symmetry based on Cahn-Ingold-Prelog (CIP) symmetry rules. For example, if a block B' of a block copolymer A'-B' contains a stereospecific first repeat unit having one asymmetric tetravalent carbon, then the first repeat unit can be present in block B' substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific first repeat unit can be present in block B' substantially as the R,R stereoisomer, substantially as the R,S stereoisomer, substantially as the S,S stereoisomer, or substantially as the S,R stereoisomer.

A "stereospecific cyclic carbonyl monomer" i) has a non-superposable mirror image and ii) comprises one or more asymmetric tetravalent carbons. A stereospecific cyclic carbonyl monomer has a stereoisomeric purity of 90% or more, and more particularly 98% or more. The asymmetric tetravalent carbons of the stereospecific cyclic carbonyl monomer can be a ring carbon that becomes a polymer backbone carbon in a ring opening polymerization.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the antimicrobial composition of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the antimicrobial composition (i.e., the concentration is below detection limits). In an embodiment, the chemical formulas of the components used to prepare the hydrogels contain none of the above restricted metals.

No restriction is placed on the concentration of boron, silicon, or any individual alkali metal in the hydrogels as long as the antimicrobial properties of the hydrogels are not adversely affected.

The hydrogels can be represented by the general formula (1):

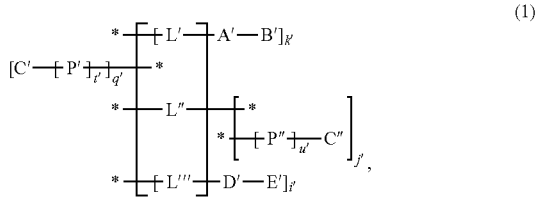

wherein
  starred bonds indicate attachment points,
  A'-B' is a pendant cationic block copolymer comprising i) a divalent block A' comprising a poly(alkylene oxide) backbone and ii) a monovalent block B' comprising a first repeat unit, the first repeat unit comprising a backbone carbonate group and a cationic side chain group,
  D'-E' is an optional pendant non-charged amphiphilic block copolymer comprising i) a block D' comprising a poly(alkylene oxide) backbone and a hydrophobic block E',
  each C' is an independent branched first core group comprising at least one carbon and having a valency of t',
  t' is an integer greater than or equal to 3,
  each C" is an independent branched second core group comprising at least one carbon and having a valency of u',
  u' is an integer greater than or equal to 3,
  each P' is an independent divalent poly(alkylene oxide) chain,
  each P" is an independent divalent poly(alkylene oxide) chain,
  each C' is linked to t' number of chains P',
  each C" is linked to u' number of chains P",
  each L' is an independent divalent linking group that covalently links a chain P' to a block A',
  each L" is an independent divalent linking group that covalently links a chain P' to a chain P",
  each L'" is an optional independent divalent linking group that covalently links a chain P' to a block D',
  q' is a number greater than 0 representing moles of C' in the hydrogel,
  j' is a number greater than 0 representing moles of C" in the hydrogel,
  k' is a number greater than 0 representing moles of block copolymer A'-B' in the hydrogel,
  i' is a number greater than or equal to 0 representing moles of optional block copolymer D'-E' in the hydrogel, and
  between 0% and 100% of the chains P' are independently covalently linked to chains P".

In the notation of formula (1) it should be understood that each chain P" is independently covalently linked to an independent linking group L", and each chain P' is independently covalently linked to an independent linking group selected from the group consisting of L', L", and L'". Also, the tallest bracket encloses the linking groups, in this instance L', L", and L'". The hydrogel contains k' moles of A'-B', k' moles of linking groups L', q' moles of C', q' t' moles of chains P', j' moles of C", u'j' moles of chains P", and u'j' moles of linking groups L". When D'-E' is present, the hydrogel also includes i' moles of D'-E' and i' moles of linking groups L'".

The hydrogel comprises an optional pendant block copolymer D'-E' in an amount effective in achieving suitable mechanical and/or physical properties of the hydrogel. In general, the hydrogel comprises pendant block copolymer D'-E' in an amount of 0 mol % to 20 mol %, more preferably 0 mol % to 10 mol % relative to moles of pendant cationic block copolymer A'-B' in the hydrogel.

In an embodiment, i' is 0, block A' comprises a backbone comprising a poly(ethylene oxide), block B' comprises a backbone selected from the group consisting of polycarbonates and polyestercarbonates, and block B' comprises a pendant quaternary amine group. In another embodiment, i' is a positive number having a value greater than 0 and less than or equal to 0.20 k', block E' comprises a backbone selected from the group consisting of polycarbonates, polyesters, and polyestercarbonates, block E' comprises a side chain urea group, block D' is equal to block A', and L' is equal to L'".

The quantity q't' can have a value of 0.50(k'+i'+u'j') to 1.5(k'+i'+u'j'), preferably 0.95(k'+i'+u'j') to 1.05(k'+i'+u'j'), and more preferably 0.99(k'+i'+u'j') to 1.01(k'+i'+u'j'). That is, q't' can have a value of +/−50%, +/−5%, or +/−1% of (k'+i'+u'j'), inclusive.

Chains P' and/or chains P''' can independently include hydrophilic, amphiphilic and/or hydrophobic repeat units. Preferably, chains P' and/or chains P''' comprise hydrophilic repeat units. Chains P' and/or chains P''' can independently comprise one or more blocks. At least one block of chains P' and/or chains P''' independently comprises a poly(alkylene oxide) backbone. In an embodiment, chains P' and/or chains P''' comprise one block comprising a poly(ethylene oxide) chain.

The molar relationship q't'=k'+i'+j'u' is preferably followed when calculating the relative amounts of hydrogel precursor materials used in the preparation of the cationic hydrogels. Preferably, but not necessarily, each individual chain P' in the hydrogel is linked to i) a block copolymer A'-B' by a linking group L', ii) a chain P''' by a linking group L'', or iii) a block copolymer D'-E' by a linking group L'''. Moreover, the reaction forming the hydrogel preferably results in each individual chain P''' linked to a chain P' by a linking group L''. Thus, k' number of L' linking groups preferably join k' number of chains P' to k' number of blocks A', i' number of L''' linking groups preferably join i' number of chains P' to i' number of blocks D', and u'j' number of L'' linking groups preferably join u'j' number of chains P''' to u'j' number of chains P' in the resultant hydrogel, thereby ideally resulting in q't'=k'+i'+j'u' for the hydrogel. Bridging groups P'-L''-P''' that connect core groups C' to core groups C''' provide for a covalently crosslinked hydrogel. In an embodiment, i' is 0, t' and u' are 4, each C' is bonded to four chains P', and each C''' is bonded to four chains P'''.

The cationic hydrogels can be a highly crosslinked networks. As stated above, the percentage of chains P' that are independently covalently linked to chains P''' in the hydrogel is between 0% and 100% (i.e., more than 0% and less than 100%). More specifically, 5% to 99%, 30% to 99%, and more preferably 55% to 95% of chains P' can be independently covalently linked to chains P''' based on molar ratios of the hydrogel precursor materials containing the chains P''' and the chains P'.

In general terms, the hydrogels comprise a branched and crosslinked network of two or more groups of polymer chains (represented herein by two groups of chains P' and P'''). The chains P' and the chains P''' independently comprise a divalent hydrophilic poly(alkylene oxide) backbone. The hydrogels comprise three or more chains P' whose respective first end units are covalently linked to a branched first core group C'. The hydrogels further comprise three or more chains P''' whose respective first end units are covalently linked to a branched second core group C'''. The chains P''' comprise respective second end units which are covalently linked to between 0% and 100% of the respective second end units of chains P' by divalent linking groups L''. The hydrogels further comprise at least one pendant cationic block copolymer chain represented herein as A'-B' comprising a block A', which is preferably hydrophilic, and a cationic block B'. Each A'-B' chain is covalently linked at one end to a chain P' of the network. More specifically, divalent block A' of the pendant cationic block copolymer comprises a poly(alkylene oxide) backbone, which is preferably hydrophilic, having an end unit that is covalently linked to a second end unit of a chain P' by a divalent linking group L'. The monovalent block B' of the pendant cationic block copolymer A'-B' comprises a first repeat unit comprising a carbonate backbone group and a cationic side chain. Block B' can further comprise a second repeat unit comprising a backbone functional group selected from the group consisting of carbonate groups and ester groups. Preferably, block B' is covalently linked to the crosslinked network through divalent block A', thereby making cationic block copolymer A'-B' a pendant chain to the network, with block B' being a terminal block of the pendant chain. The hydrogels comprise at least one chain P' covalently linked to a block A' by a divalent linking group L'. Preferably, the respective second end units of the chains P''' are covalently linked through divalent linking groups L'' to second end units of chains P'. In an embodiment, the first repeat unit of block B' comprises a side chain quaternary amine group. In another embodiment, block B' is a random copolymer chain comprising a cationic first repeat unit and one or more hydrophobic non-charged second repeat units. Thus, block B' can be hydrophilic or amphiphilic.

The cationic hydrogels can optionally further comprise a pendant biodegradable non-charged amphiphilic block copolymer D'-E', which comprises a block D' and a hydrophobic block E'. Each D'-E' chain when present is preferably covalently linked at one end to a chain P' of the network; thus D'-E' is also pendant to the network. Divalent block D' of the pendant cationic block copolymer comprises a poly(alkylene oxide) backbone, preferably hydrophilic, having an end unit which is covalently linked to a second end unit of a chain P' by a divalent linking group L'''. Block E' of the pendant block copolymer D'-E' comprises non-charged repeat units. In an embodiment, block E' comprises a repeat unit comprising a pendant urea group. The non-charged pendant block copolymer D'-E' can be used to control the mechanical properties of the hydrogel; for example, by increasing the dynamic storage modulus of the hydrogel without substantially degrading antimicrobial activity. Preferably, block copolymer A'-B' and block copolymer D'-E' are formed by organocatalyzed ring opening polymerization. In another embodiment, block A', block D', chains P' and chains P''' comprise a poly(ethylene oxide) backbone.

The pendant cationic block copolymer can comprise two or more blocks, wherein at least one block B' is cationic. In the simplest case, the pendant cationic block copolymer comprises two blocks represented as A'-B'. In this instance, block B' can comprise a living end unit, such as an end unit comprising a nucleophilic group capable of initiating a ring opening polymerization.

Alternatively, block A' of pendant block copolymer A'-B' can be connected to the crosslinked network through block B'. In this instance, linking group L' covalently joins block B' to a chain P', and block A' has an unbound end unit, which can be a living end unit. Without being bound by theory, this arrangement is believed to be less preferred due to increased steric shielding of the cationic repeat unit of block B' by block A', which can potentially interfere with the cationic groups making contact with and disrupting a microbial cell membrane.

The optional pendant non-charged block copolymer D'-E' can comprise two or more blocks. In the simplest case, the pendant non-charged block copolymer comprises two blocks represented as D'-E'. In this instance, the block E' can comprise a living end unit, such as an end unit comprising a nucleophilic group capable of initiating a ring opening polymerization. In an embodiment, block D' comprises a poly(alkylene oxide) and block E' comprises a pendant urea group.

Alternatively, the optional pendant block copolymer block D' can be connected to the crosslinked network through block E'. In this instance, linking group L' joins block E' to a chain P', and block D' has an unbound end unit, which can be a living end unit.

Each C' is an independent branched first core group comprising at least one carbon. C' is bonded to t' number of independent chains P'. As one example, the branched first core group can comprise a central tetrahedral carbon bonded to three or four bridging groups connected to independent chains P'. In this instance, C' can have the general formula (2):

$$C(H)_{n'}(R')_{4-n'} \qquad (2),$$

wherein n' is 0 or 1, and each R' is an independent divalent radical selected from the group consisting of *—O—*, alkoxy groups comprising 0 to 100 carbons, and aryloxy groups comprising 0 to 100 carbons, wherein the starred bond indicates an attachment site. R' can comprise a ring and/or a heteroatom selected from nitrogen and/or sulfur heteroatoms. In an embodiment, n' is 0, each R' is *—CH$_2$O—*, wherein the oxygen is linked to an independent chain P'. This core group is a pentaerythritolyl core group having the structure C(CH$_2$O—*)$_4$.

Each C" is an independent branched second core group comprising at least one carbon. C" is bonded to each of u' number of chains P". As one example, the branched second core group can comprise a central tetrahedral carbon bonded to at least three bridging groups linked to independent chains P". In this instance, C" can have the general formula (3):

$$C(H)_{n''}(R'')_{4-n''} \qquad (3),$$

wherein n" is 0 or 1, and each R" is a divalent radical selected from the group consisting of *—O—*, alkoxy groups comprising 0 to 100 carbons, and aryloxy groups comprising 0 to 100 carbons. R" can comprise a ring and/or a heteroatom selected from nitrogen and/or sulfur heteroatoms. In an embodiment, C" is a pentaerythritolyl group C(CH$_2$O—*)$_4$; wherein each oxygen is linked to an independent chain P".

C' and/or C" can be stereospecific or non-stereospecific groups. C' and/or C" can comprise one or more tetravalent asymmetric carbons.

Additional examples of C' and C" groups include the structures of Table 1 and stereoisomers thereof. Asymmetric carbon centers are labeled with R,S stereochemistry. In Table 1, starred bonds represent potential attachment points to a chain P' or a chain P". One or more of the oxygens having a starred bond can be individually attached to an alkyl group such as a methyl and/or ethyl group, as long as at least three sites of attachment to chains P' are present in a C' group, and at least three sites of attachment to chains P" are present in a C" group.

TABLE 1

Glycerolyl

Arabitolyl

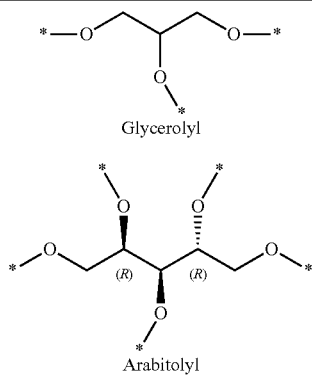

TABLE 1-continued

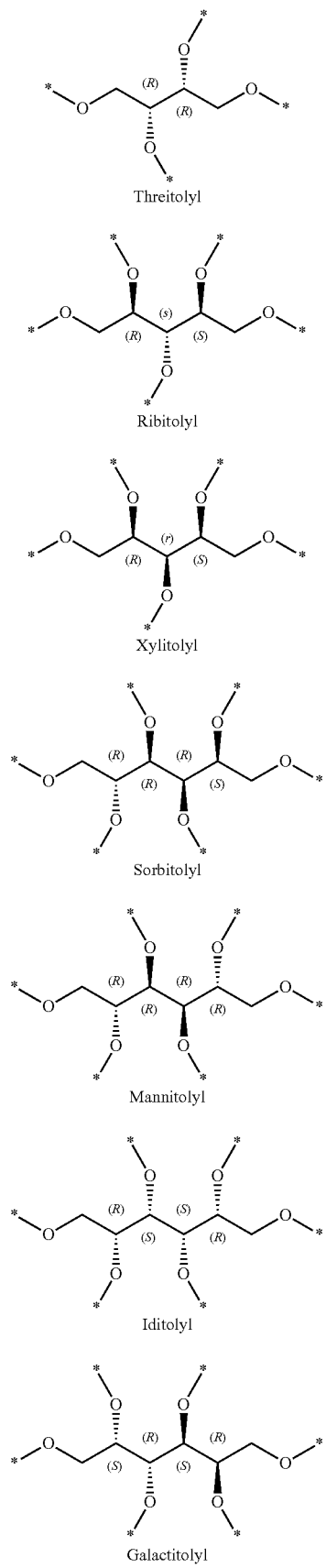

TABLE 1-continued

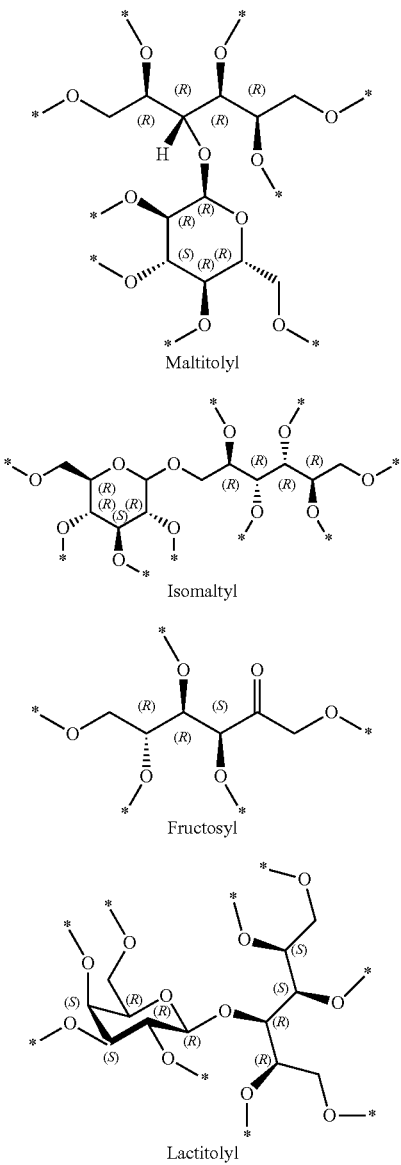

Maltitolyl

Isomaltyl

Fructosyl

Lactitolyl

As indicated by the structures in Table 1, the C' and C" core groups can comprise other functional groups, for example ketones, ketals, acetals, esters, amides, and combinations thereof.

In an embodiment, each chain P' independently comprises a repeat unit selected from the group consisting of ethylene oxide (*—CH$_2$CH$_2$O—*), propylene oxide (*—CH$_2$CH(CH$_3$)O—*), and mixtures thereof. In another embodiment, each chain P' comprises a poly(ethylene oxide) chain. The weight average molecular weight (Mw) of the poly(ethylene oxide) chain of a chain P' can be 1000 to 100,000 Daltons, 1000 to 20000 Daltons, or preferably 1000 to 15000 Daltons.

In an embodiment, each chain P''' independently comprises a repeat unit selected from the group consisting of ethylene oxide (*—CH$_2$CH$_2$O—*), propylene oxide (*—CH$_2$CH(CH$_3$)O—*), and mixtures thereof. In an embodiment, each P''' comprises a poly(ethylene oxide) chain. The weight average molecular weight (Mw) of the poly(ethylene oxide) chain of a chain P''' can be 1000 to 100,000 Daltons, 1000 to 20000 Daltons, or more preferably 1000 to 15000 Daltons.

For biocompatibility purposes, the preferred weight average molecular weight (Mw) of the poly(alkylene oxide) chain of chains P', chains P''', block A', and block D' is about 1000 Daltons to about 5000 Daltons.

Each L' is an independent divalent linking group, each L" is an independent divalent linking group, and each L''' is an independent divalent linking group. In a specific embodiment, each of the linking groups L', L", and L''' comprises a backbone sulfide group (i.e., *—CH$_2$SCH$_2$—*). In a more specific embodiment, each of the linking groups L', L", and L''' comprises a backbone beta-sulfido carbonyl group having the structure

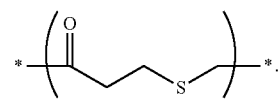

In this instance, L', L", and L''' can be selected independently from linking groups of the formula (4):

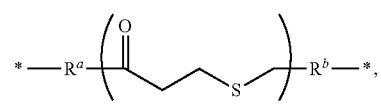

(4)

wherein R$^a$ and R$^b$ independently represent single bonds or divalent functional groups comprising 0 to 100 carbons. R$^a$ and R$^b$ can comprise heteroatoms such as oxygen, sulfur and/or nitrogen. R$^a$ and R$^b$ can further comprise an aliphatic and/or aromatic ring.

Linking group L' covalently joins a chain P' to a block A' of the pendant cationic block copolymer A'-B'. When L' is a linking group of formula (4), a chain P' or block A' can be covalently linked to the carbonyl end or the sulfur end of the linking group represented by formula (4). In an embodiment, R$^a$ represents a single bond that covalently links a chain P' to the carbonyl of the beta-sulfido carbonyl group of formula (4), and R$^b$ is a functional group linked to a first end unit of block A'.

Linking group L" covalently joins a chain P' to a chain P'''. When L" is a linking group of formula (4), a chain P' or a chain P''' can be linked to the carbonyl end or the sulfur end of the linking group represented by formula (4). In an embodiment, R$^a$ represents a single bond that covalently links a chain P' to the carbonyl of the beta-sulfido carbonyl group, and R$^b$ is a divalent alkyl group linked to a chain P'''.

Linking group L''' covalently joins a chain P' to a block D' of the pendant non-charged block copolymer D'-E'. When L''' is a linking group of formula (4), a chain P' or a block D' can be covalently linked to the carbonyl end or the sulfur end of the linking group represented by formula (4). In an embodiment, R$^a$ represents a single bond that covalently links a chain P' to the carbonyl of the beta-sulfido carbonyl group of formula (4). In another embodiment, L''' has the same structure as L'.

Preparation of Hydrogels.

The disclosed hydrogels can be prepared using the following components: i) an electrophilic polymeric crosslinking agent, referred to as the first crosslinking agent, which comprises an electrophilic group F', ii) a nucleophilic cationic block copolymer, which comprises a nucleophilic group N$^a$ capable of reacting with electrophilic group F' to form a linking group L', iii) a nucleophilic polymeric crosslinking agent, referred to as the second crosslinking agent, which comprises a nucleophilic group $N^b$ capable of reacting with F' to form a linking group L'', and optionally iv) a second non-charged nucleophilic block copolymer comprising a nucleophilic group $N^c$ capable of reacting with electrophilic group F' to form linking group L'''.

The first crosslinking agent has the formula (5):

wherein C', P' and t' are defined as above for formula (1), and each F' is an independent monovalent electrophilic group. In an embodiment, F' comprises an alpha,beta-unsaturated carbonyl group (*—C(=O)—CH=CH—*) capable of undergoing a Michael addition reaction with $N^a$ and/or $N^b$.

The second crosslinking agent has the formula (6):

wherein C'', P'' and u' are defined as above, and each $N^b$ is an independent monovalent nucleophilic group capable of reacting with electrophilic group F' of the first branched material to form a second linking group L''. In an embodiment, $N^b$ reacts with F' by a Michael addition reaction.

The cationic nucleophilic block copolymer has the general formula (7):

$$N^a\text{-}A'\text{-}B' \quad (7),$$

wherein A' and B' are defined above and $N^a$ represents a monovalent nucleophilic group capable of reacting with an electrophilic group F' of the first crosslinking agent to form the above described first linking group L'. Cationic nucleophilic block copolymer $N^a$-A'-B' can be prepared as described further below by ring opening polymerization of one or more cyclic carbonyl monomer(s). In an embodiment, $N^a$ reacts with F' by a Michael addition reaction.

The optional non-charged nucleophilic block copolymer has the general formula (7a):

$$N^c\text{-}D'\text{-}E' \quad (7a),$$

wherein D' and E' are defined above and $N^c$ represents a monovalent nucleophilic group capable of reacting with an electrophilic group F' of the first crosslinking agent to form the above described linking group L'''. Cationic nucleophilic block copolymer $N^c$-D'-E' can be prepared as demonstrated further below by ring opening polymerization of one or more cyclic carbonyl monomer(s). In an embodiment, $N^c$ reacts with F' by a Michael addition reaction.

Non-limiting electrophilic groups F' include, for example, alkyl halides, epoxides, and active esters, which can react with a nucleophile to eliminate a halide, ring open an epoxide, or transesterify an ester group, respectively. Preferred electrophilic groups F' include i) alpha,beta-unsaturated carbonyl-containing functionalities such as vinyl ketones, acrylates, acrylamides, and maleimides, and ii) alpha,beta-unsaturated sulfonyl-containing functionalities such as vinyl sulfonamides and vinyl sulfones. These groups can react by Michael addition of a nucleophilic group $N^a$ and/or $N^b$ to the double bond of the alpha,beta-unsaturated carbonyl and/or sulfonyl group.

Non-limiting examples of first crosslinking agents C'[—P'—F']$_{t'}$ include materials of Table 2 below. The materials designated "4Arm" in Table 2 comprise a pentaerythritolyl core group C[CH$_2$O—*]$_4$. The compounds designated "8Arm" in Table 2 comprise a hexaglycerolyl core group, which has the structure:

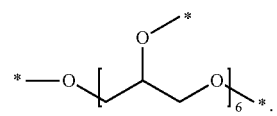

The commercially available materials of Table 2 comprise derivatized poly(ethylene glycol) HO(CH$_2$CH$_2$O)$_n$H (PEG). Hence, PEG appears in the commercial names of these materials. The *—(CH$_2$CH$_2$O)$_n$—* chain is also be referred to as a poly(ethylene oxide) (PEO) chain.

TABLE 2

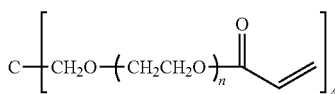

(4Arm-PEG-Acrylate)

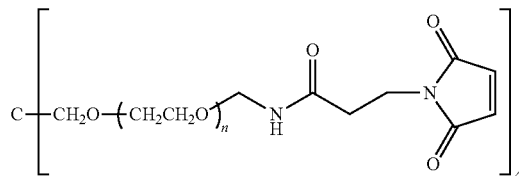

(4Arm-PEG-Maleimide)

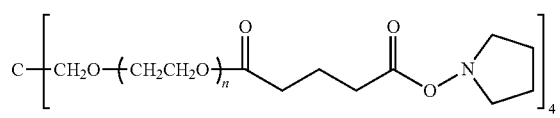

(4Arm-PEG-Succinimidyl Glutarate)

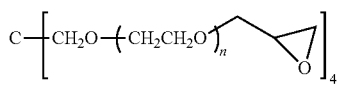

(4Arm-PEG-Epoxide)

TABLE 2-continued
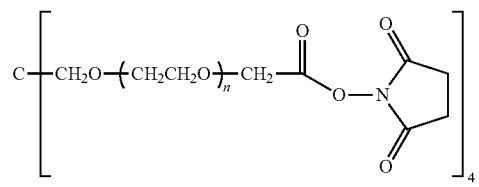
(4Arm-PEG-Succinimidyl Ester)
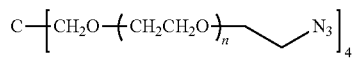
(4Arm-PEG-Azide)
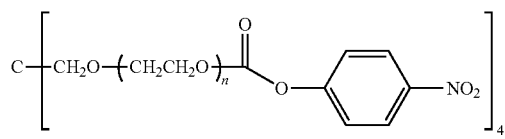
(4Arm-PEG-p-Nitrophenyl Carbonate)
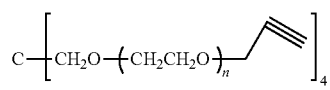
(4Arm-PEG-Alkyne)
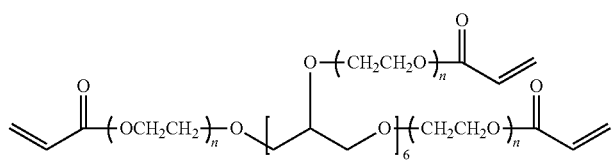
(8Arm-PEG-Acrylate)
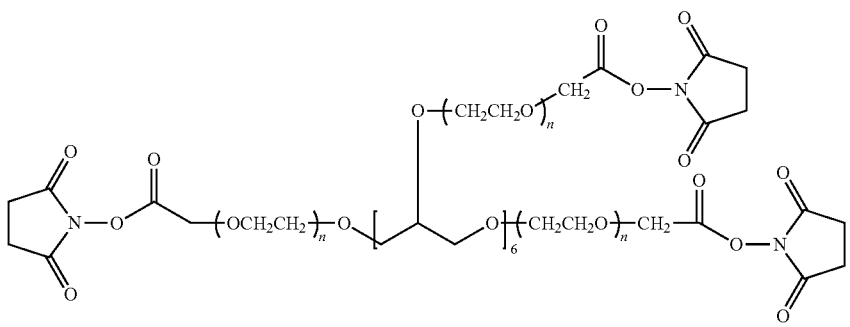
(8Arm-PEG-Succinimidyl Ester)
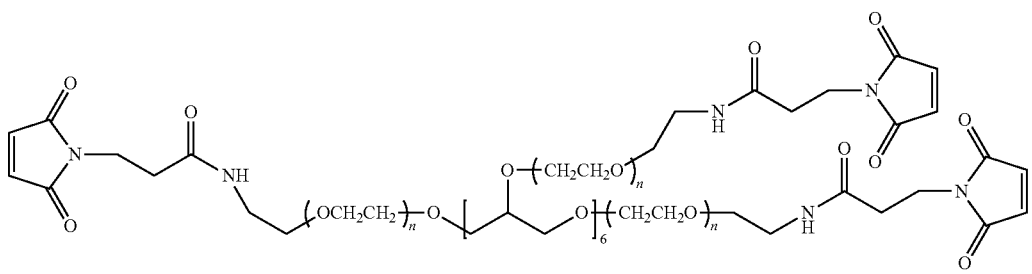
(8Arm-PEG-Maleimide)

TABLE 2-continued

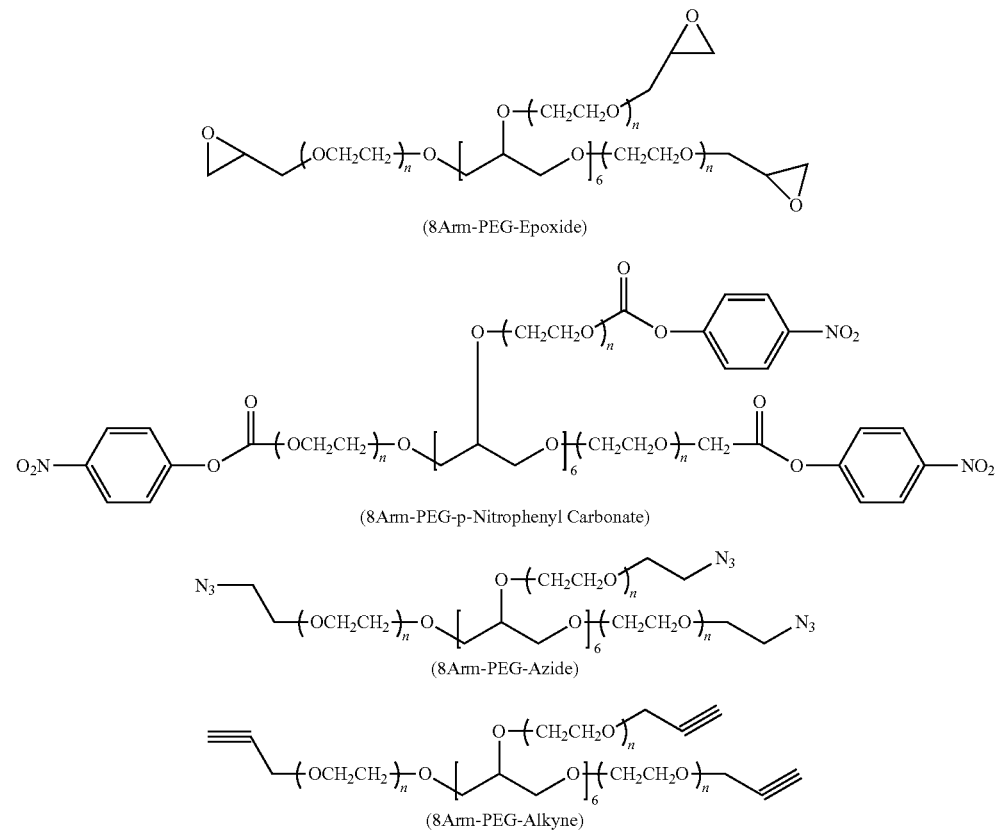

In an embodiment the electrophilic groups F' comprise an acrylate or methacrylate group capable of a Michael addition reaction with a suitable nucleophilic group $N^a$, $N^b$ and/or $N^c$.

Non-limiting examples of nucleophilic groups $N^a$, $N^b$ and/or $N^c$ include alcohols, hydroxylates, amines, thiols, thiolates, enols, enolates, active methylenes, carbanions, and carboxylates.

Non-limiting examples of second crosslinking agents $C''[\text{—}P''\text{—}N^b]_{u'}$ include the materials of Table 3.

TABLE 3

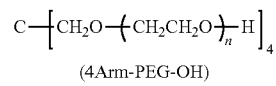
(4Arm-PEG-OH)

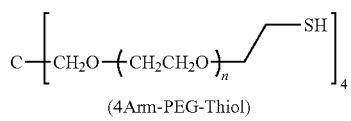
(4Arm-PEG-Thiol)

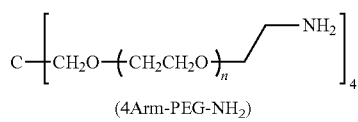
(4Arm-PEG-NH$_2$)

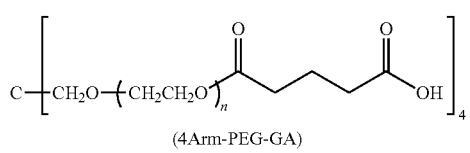
(4Arm-PEG-GA)

TABLE 3-continued

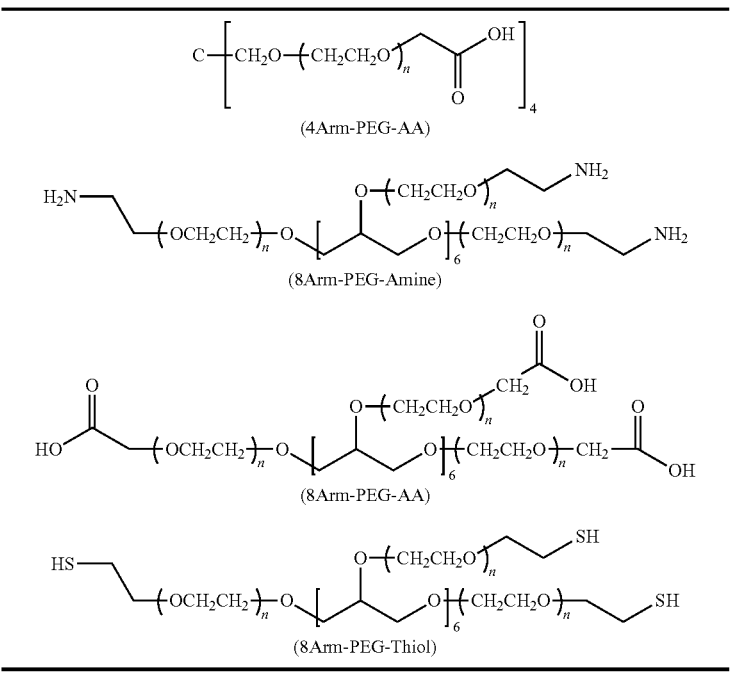

In an embodiment, nucleophilic group $N^a$ of the block copolymer $N^a$-A'-B', nucleophilic group $N^b$ of the second crosslinking agent, and (when present) nucleophilic group $N^c$ of the non-charged block copolymer $N^c$-D'-E' comprise a thiol group, and the thiol group undergoes Michael addition with the F' group of the first crosslinking agent. In another embodiment, the F' group of the first crosslinking agent is an acrylate ester group.

The hydrogels can be prepared sequentially. A method comprises:
forming a mixture comprising i) a first crosslinking agent $C'[—P'—F'']_{t'}$, ii) a cationic nucleophilic block copolymer $N^a$-A'-B' wherein $N^a$ is capable of reacting with F' to form a divalent linking group L', iii) a base, and optionally iv) a nucleophilic non-charged amphiphilic block copolymer $N^c$-D'-E' wherein $N^c$ is capable of reacting with F' to form a divalent linking group L";
agitating the mixture, thereby forming an adduct, wherein the adduct comprises unreacted electrophilic groups F';
forming a hydrogel precursor mixture comprising the adduct and a second crosslinking agent $C''[—P'''—N^b]_{u'}$, wherein $N^b$ is capable of reacting with F' to form a divalent linking group L''';
and allowing and/or inducing the hydrogel precursor mixture to crosslink, thereby forming a covalently crosslinked cationic hydrogel. $C'[—P'—F']_{t'}$, $N^a$-A'-B', $C''[—P'''—N^b]_{u'}$, and $N^c$-D'-E' have the definitions described further above. $N^a$, $N^b$, and optionally $N^c$ react with F' to form linking groups L', L", and L''', respectively, which have the definitions described above. $N^a$-A'-B', $N^c$-D'-E', and $C''[—P'''—N^b]_{u'}$ can be added to the reaction mixture in any order. In an embodiment the hydrogel has the formula (1). In another embodiment, $N^a$, $N^b$ and $N^c$ react by a Michael addition reaction with F'.

Alternatively, the hydrogel can be prepared by co-reacting the hydrogel precursor materials in one step. The method comprises combining i) a first crosslinking agent $C'[—P'—F']_{t'}$, ii) a cationic nucleophilic block copolymer $N^a$-A'-B', iii) a base, iv) the second crosslinking agent $C''[—P'''—N^b]_{u'}$, and optionally v) a non-charged nucleophilic block copolymer $N^c$-D'-E', thereby forming a hydrogel precursor mixture; and allowing and/or inducing the hydrogel precursor mixture to crosslink, thereby forming a covalently crosslinked cationic hydrogel. $C'[—P'—F']_{t'}$, $N^a$-A'-B', $N^c$-D'-E', and $C''[—P'''—N^b]_{u'}$, L', L", and L''' have the definitions described further above. In an embodiment, the hydrogel precursor mixture reacts by a Michael addition reaction to form the crosslinked hydrogel network. In another embodiment, L', L", and L''' comprise a beta-sulfido carbonyl group. In another embodiment, the hydrogel has a structure according to formula (1).

The method can further comprise disposing the hydrogel precursor mixture on a surface of a substrate in the form a fluid solution before substantial crosslinking occurs, thereby forming a hydrogel precursor layer comprising the hydrogel precursor mixture disposed on the surface of the substrate; and allowing and/or inducing the hydrogel precursor layer to crosslink, thereby forming an antimicrobial layer comprising a covalently crosslinked cationic hydrogel disposed on the surface of the substrate.

The hydrogel precursor mixture and/or the hydrogel precursor layer can be induced to crosslink, for example, by a treating by a thermal and/or photochemical treatment. More specifically, the hydrogel precursor layer can be heated at a temperature of 30° C. to 50° C. for 1 to 10 minutes to form the crosslinked cationic hydrogel.

The hydrogel precursor mixture can further include a gene and/or a drug, referred to as a loaded hydrogel precursor mixture. In this instance, allowing and/or inducing the loaded hydrogel precursor mixture to crosslink forms a composition, referred to as a loaded hydrogel, which comprises i) a covalently crosslinked cationic hydrogel and ii) a gene and/or a drug occluded therein. The gene and/or the drug preferably does not react with any of the hydrogel precursors to form a covalent bond.

The loaded hydrogel precursor mixture can be disposed on a surface of a substrate, thereby forming a loaded hydrogel precursor layer. Allowing and/or inducing the loaded hydrogel precursor layer to crosslink results in an antimicrobial layer composition comprising i) a covalently crosslinked cationic hydrogel and ii) a gene and/or a drug occluded therein, which is disposed on the surface of the substrate.

A method of forming a loaded hydrogel based on formula (1) comprises:
  forming a first mixture comprising i) a first crosslinking agent C'[—P'—F']$_{t'}$, ii) a cationic nucleophilic block copolymer N$^a$-A'-B' formed by organocatalyzed ring opening polymerization, iii) a base; and optionally v) a nucleophilic non-charged amphiphilic block copolymer N$^c$-D'-E', wherein F' is an electrophilic group and N$^a$ and N$^c$ are nucleophilic groups capable of reacting independently with F' to form divalent linking groups L' and L''', respectively;
  agitating the first mixture, thereby forming an adduct, wherein the adduct comprises unreacted electrophilic groups F' and/or F'';
  forming a hydrogel precursor mixture comprising i) the adduct, ii) a second crosslinking agent C''[—P''—N$^b$]$_{u'}$, and iii) a drug and/or a gene, wherein N$^b$ is a nucleophilic group capable of reacting independently with F' to form divalent linking group L''; and
  allowing and/or inducing the hydrogel precursor mixture to crosslink, thereby forming the loaded hydrogel comprising i) the hydrogel of formula (1) and ii) the gene and/or the drug occluded therein.

Another method of forming a loaded hydrogel based on formula (1) comprises:
  combining i) a first crosslinking agent C'[—P'—F']$_{t'}$, ii) a cationic nucleophilic block copolymer N$^a$-A'-B' formed by organocatalyzed ring opening polymerization, iv) a base; and optionally iii), a nucleophilic non-charged amphiphilic block copolymer N$^c$-D'-E', v) a second crosslinking agent C''[—P''—N$^b$]$_{u'}$, and iv) a gene and/or a drug, thereby forming a hydrogel precursor mixture, wherein F' is an electrophilic group, and N$^a$, N$^b$, and N$^c$ are nucleophilic groups capable of reacting independently with F' to form divalent linking groups L', L'', and L''', respectively; and
  allowing and/or inducing the mixture to crosslink, thereby forming the loaded hydrogel comprising i) the hydrogel of formula (1) and ii) the gene and/or the drug occluded therein.

The above-described methods can further include an optional electrophilic non-polymeric (i.e., oligomeric and/or monomeric) crosslinking agent S'[—F'']$_{v'}$, wherein v' is 2 or more, S' is a non-polymeric group comprising at least one carbon, and F'' is an electrophilic group. F'' is capable of reacting with the nucleophilic groups N$^a$ of the nucleophilic block copolymer N$^a$-A'-B', N$^b$ of the second crosslinking agent C''[—P''—N$^b$]$_{u'}$, and/or N$^c$ of the nucleophilic block copolymer N$^c$-D'-E'. When present, the S' core group becomes covalently linked to two or more members selected from the groups consisting of chains P''', block A', block D' and combinations thereof. The electrophilic non-polymeric crosslinking agent S'[—F'']$_{v'}$ can be added at any stage before gelation. Electrophilic non-polymeric crosslinking agents include diacrylates, triacrylates, and tetraacrylates, bis(vinyl sulfones), and bis(maleimides). The S' group of the electrophilic non-polymeric crosslinking agent becomes a non-polymeric core group covalently linked to two or more members of the group consisting of chains P''', cationic block A'-B', non-charged block copolymer D'-E', and combinations thereof. In an embodiment, the electrophilic non-polymeric crosslinking agent S'[—F'']$_{v'}$ is pentaerythritol tetraacrylate.

The hydrogel precursor mixture can further include an optional nucleophilic non-polymeric crosslinking agent S''[—N$^d$]$_{w'}$, wherein w' is 2 or more, S'' is a non-polymeric core group comprising at least one carbon, and N$^d$ is an nucleophilic group capable of reacting with the electrophilic groups F' of the first crosslinking agent C'[—P'—F']$_{t'}$ and/or the electrophilic groups F'' of the electrophilic non-polymeric crosslinking agent S'[—F'']$_{v'}$. The nucleophilic non-polymeric crosslinking agent S''[—N$^d$]$_{w'}$ can be added at any stage before gelation. Non-limiting nucleophilic non-polymeric crosslinking agents include, for example, dithiols, trithiols, tetrathiols, diols, diamines, and compounds comprising combinations of amines, alcohols and thiols. The S'' becomes a non-polymeric core group in the hydrogel covalently linked to two or more members selected from the groups consisting of chains P', S', and combinations thereof.

Generally, the electrophilic and/or nucleophilic non-polymeric crosslinking agents can be used in an amount of 0 mol % to 30 mol %, preferably 0 mol % to 10 mol %, based on total moles of the hydrogel precursors.

Using the notation of formula (1) and including the optional electrophilic and nucleophilic non-polymeric crosslinking agents, the hydrogel can have a structure in accordance with formula (1a):

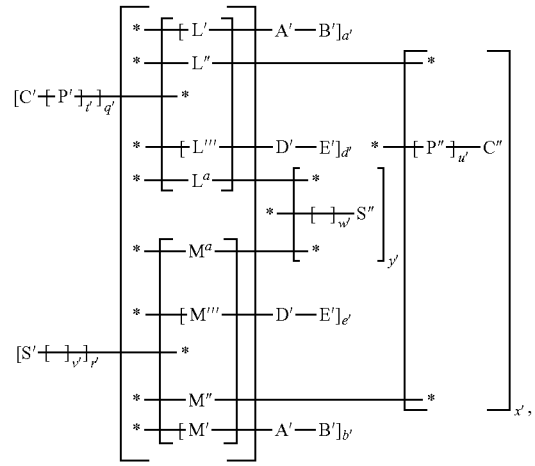

(1a)

wherein
  starred bonds indicate attachment points,
  A'-B' is a pendant cationic block copolymer comprising i) a divalent block A' comprising a poly(alkylene oxide) backbone and ii) a monovalent cationic block B' comprising a first repeat unit, the first repeat unit comprising a backbone carbonate group and a cationic side chain group,
  D'-E' is a pendant non-charged amphiphilic block copolymer comprising i) a block D' comprising a poly(alkylene oxide) backbone and a hydrophobic block E,
  each C' is an independent branched first core group comprising at least one carbon and having a valency of t',
  t' is an integer greater than or equal to 3,
  each C'' is an independent branched second core group comprising at least one carbon and having a valency of u',
  u' is an integer greater than or equal to 3,
  each P' is an independent divalent poly(alkylene oxide) chain, each P''' is an independent divalent poly(alkylene oxide) chain, each L' is an independent divalent linking group that covalently links a chain P' to a block A', each L'' is an independent divalent linking group that covalently links a chain P' to a chain P''', each L''' is an independent divalent linking group that covalently links a chain P' to a block D', each S' is an independent non-polymeric core group (e.g., derived from an electrophilic non-polymeric crosslinking agent) comprising at least one carbon and having a valency of v', wherein v' is a positive integer greater than or equal to 2, each S'' is an independent non-polymeric core group (e.g., derived from an nucleophilic non-polymeric crosslinking agent) comprising at least one carbon and having a valency of w', wherein w' is a positive integer greater than or equal to 2, each $L^a$ is an independent divalent linking group that covalently links a S'' group to a chain P', each $M^a$ is an independent divalent linking group that covalently links a S'' group to a S' group, each M' is an independent divalent linking group that covalently links a S' group to a block A' of block copolymer A'-B', M'' is an independent divalent linking group that covalently links a S' group to a chain P''', M''' is an independent divalent linking group that covalently links a S' group to a block D' of block copolymer D'-E', a' is a number greater than 0 representing moles of A'-B' linked to chains P' in the hydrogel, b' is a number greater than or equal to 0 representing moles of A'-B' linked to S' in the hydrogel, d' is a number greater than or equal to 0 representing moles of D'-E' linked to chains P' in the hydrogel, e' is a number greater than or equal to 0 representing moles of D'-E' linked to S' in the hydrogel, q' is a number greater than 0 representing moles of C' in the hydrogel, x' is a number greater than 0 representing moles of C'' in the hydrogel, y' is a number greater than or equal to 0 representing moles of S'' in the hydrogel, r' is a number greater than or equal to 0 representing moles of S' in the hydrogel, each C' is linked to t' number of chains P', each C'' is linked to u' number of chains P''', each S' group is linked to v' number of linking groups independently selected from the group consisting of M', M'', M''', and $M^a$, each S'' group is linked to w' number of linking groups independently selected from the group consisting of $L^a$ and $M^a$, and between 0% and 100% of the chains P' are independently covalently linked to chains P''' in the hydrogel.

It should be understood from the above notation that each chain P''' is covalently linked to a linking group independently selected from the group consisting of L'' and M'', each chain P' is covalently linked to a linking group independently selected from the group consisting of L', L'', L''' and $L^a$, each S'' (when present) is covalently linked to w' number of linking groups independently selected from the group consisting of $L^a$ and $M^a$, and each S' (when present) is covalently linked to v' number of linking groups independently selected from the group consisting of M', M'', M''', and $M^a$. The tallest bracket encloses the linking groups L', L'', L''' $L^a$, M', M'', M''', and $M^a$. The brackets within the tallest bracket enclose the linking groups according to whether they connect to chains P' or core group S'.

The molar relationship q't'+v'r'=(a'+b')+(d'+e')+w'y'+u'x' is preferably followed when calculating amounts of the hydrogel precursor materials used in the preparation of the hydrogel. That is, total moles of electrophilic groups F' and F'' used in the hydrogel precursor mixture preferably equals total moles of nucleophilic groups $N^a$, $N^b$, $N^c$, and $N^d$. Linking groups L', L'', L''', $L^a$, M', M'', M''', and $M^a$ are preferably formed in amounts such that q't'+v'r'=(a'+b')+(d'+e')+w'y'+u'x' in the hydrogel.

The quantity y't'+v'r' can have a value of 0.50((a'+b')+(d'+e')+w'y'+u'x') to 1.5((a'+b')+(d'+e')+w'y'+u'x'), preferably 0.95((a'+b')+(d'+e')+w'y'+u'x') to 1.05((a'+b')+(d'+e')+w'y'+u'x'), and more preferably 0.99((a'+b')+(d'+e')+w'y'+u'x') to 1.01((a'+b')+(d'+e')+w'y'+u'x'). That is, y't'+v'r' can have a value of +/−50%, +/−5%, or +/−1% of ((a'+b')+(d'+e')+w'y'+u'x'), inclusive.

In an embodiment, y' is 0, and L', L'', L''', M', M'', and M''' comprise a backbone beta-sulfido carbonyl group having the structure

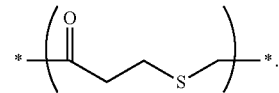

In another embodiment, S' and/or S'' is a pentaerythritolyl group $C(CH_2O-*)_4$.

Another method comprises:

forming a first mixture comprising i) a first crosslinking agent $C'[-P'-F']_{t'}$, optionally ii) an electrophilic non-polymeric crosslinking agent, $S'[-F'']_{v'}$, iii) a cationic nucleophilic block copolymer $N^a$-A'-B' formed by organocatalyzed ring opening polymerization, iv) a base; and optionally v), a nucleophilic non-charged amphiphilic block copolymer $N^c$-D'-E;

agitating the first mixture, thereby forming an adduct, wherein the adduct comprises unreacted electrophilic groups F' and/or F'';

forming a hydrogel precursor mixture comprising i) the adduct, ii) a second crosslinking agent $C''[-P'''-N^b]_{u'}$, and optionally iii) a nucleophilic non-polymeric crosslinking agent $S''[-N^d]_{w'}$;

and allowing and/or inducing the hydrogel precursor mixture to crosslink, thereby forming a covalently crosslinked cationic hydrogel. In this method, $C'[-P'-F']_{t'}$, $N^a$-A'-B', $N^c$-D'-E', and $C''[-P'''-N^b]_{u'}$, $S'[-F'']_{v'}$, and $S''[-N^d]_{w'}$ have the definitions described further above.

Another method comprises:

combining i) a first crosslinking agent $C'[-P'-F']_{t'}$, optionally ii) an electrophilic non-polymeric crosslinking agent, $S'[-F'']_{v'}$, iii) a cationic nucleophilic block copolymer $N^a$-A'-B', iv) a base; optionally v) a nucleophilic non-charged amphiphilic block copolymer $N^c$-D'-E', vi) a second crosslinking agent $C''[-P'''-N^b]_d$, and optionally vii) a nucleophilic non-polymeric crosslinking agent $S''[-N^d]_{w'}$, thereby forming a hydrogel precursor mixture; and allowing and/or inducing the hydrogel precursor mixture to crosslink, thereby forming a covalently crosslinked hydrogel. $C'[-P'-F']_{t'}$, $N^a$-A'-B', $N^c$-D'-E', and $C''[-P'''-N^b]_{u'}$, $S'[-F'']_{v'}$, and $S''[-N^d]_{w'}$ have the definitions described further above.

Nucleophilic group $N^a$ is capable of reacting with electrophilic group F' to form a divalent linking group L' and/or reacting with electrophilic group F''' to form a divalent linking group M'. Nucleophilic group $N^b$ is capable of reacting with F' to form a divalent linking group L'' and/or reacting with F''' to form a divalent linking group M''. Nucleophilic group $N^c$ is capable of reacting with F' to form a divalent linking group L''' and/or reacting with F''' to form divalent linking group M'''. $N^d$ is a nucleophilic group capable of reacting with F' to form a divalent linking group $L^a$ and/or reacting with F''' to form a divalent linking group $M^a$. In an embodiment. the hydrogel has the formula (1a). $N^a$-A'-B', $N^c$-D'-E', and C''[—P''—$N^b$]$_{u'}$ and S''[—$N^d$]$_{w'}$ can be added to the reaction mixture in any suitable order relative to C'[—P'—F']$_{t'}$ and S'[—F'']$_{v'}$. In another embodiment, the adduct forms by a Michael addition reaction. In another embodiment, nucleophilic groups $N^a$, $N^b$, $N^c$ and $N^d$ independently react by a Michael addition reaction with F' and/or F''' to form covalent bonds. In another embodiment, the method comprises disposing the hydrogel precursor mixture on a surface of a substrate before substantial crosslinking occurs, thereby forming a hydrogel precursor layer comprising the hydrogel precursor mixture disposed on the surface of the substrate; and allowing and/or inducing the hydrogel precursor layer to crosslink, thereby forming an antimicrobial layer comprising the covalently crosslinked cationic hydrogel disposed on the surface of the substrate. In another embodiment, the hydrogel precursor mixture comprises the gene and/or the drug, and the antimicrobial microbial layer comprises a loaded hydrogel, the loaded hydrogel comprising i) the covalently crosslinked cationic hydrogel and ii) the gene and/or the drug occluded therein.

The gene and/or the drug can be occluded reversibly or non-reversibly in the loaded hydrogel network. The gene and/or the drug preferably does not react with any of the hydrogel precursors to form a covalent bond. The gene and/or the drug can be added at any suitable stage in the preparation of the hydrogel, and in an amount sufficient to obtain a desired biological response. In some instances, the hydrogel can be loaded with a gene and/or drug after gelation is complete, for example by bathing a layer of the hydrogel in a solution of the gene and/or the drug in an suitable solvent (e.g., water, PBS). The loaded hydrogels containing the gene and/or drug can have useful controlled release properties. Controlled release of a drug from the loaded hydrogel can be sustained for a period of 1 or more hours, in particular 1 or more days.

A method of forming a loaded hydrogel based on formula (1a) comprises:

forming a first mixture comprising i) a first crosslinking agent C'[—P'—F']$_{t'}$, optionally ii) an electrophilic non-polymeric crosslinking agent, S'[—F'']$_{v'}$, iii) a cationic nucleophilic block copolymer $N^a$-A'-B' formed by organocatalyzed ring opening polymerization, iv) a base; and optionally v) a nucleophilic non-charged amphiphilic block copolymer $N^c$-D'-E', wherein F' and F''' are electrophilic groups and $N^a$ and $N^c$ are nucleophilic groups capable of reacting independently with F' and/or F''' to form a covalent bond;

agitating the first mixture, thereby forming an adduct, wherein the adduct comprises unreacted electrophilic groups F' and/or F''';

forming a hydrogel precursor mixture comprising i) the adduct, ii) a second crosslinking agent C''[—P''—$N^b$]$_{u'}$, optionally iii) a nucleophilic non-polymeric crosslinking agent S''[—$N^d$]$_{w'}$ wherein $N^b$ and $N^d$ are nucleophilic groups capable of reacting independently with F' and/or F''' to form a covalent bond, and a gene and/or a drug; and allowing and/or inducing the hydrogel precursor mixture to crosslink, thereby forming the loaded hydrogel comprising the i) the hydrogel of formula (1) and ii) the gene and/or the drug occluded therein.

Another method of forming a loaded hydrogel based on formula (1a) comprises:

forming a mixture comprising i) a first crosslinking agent C'[—P'—F']$_{t'}$, optionally ii) an electrophilic non-polymeric crosslinking agent, S'[—F'']$_{v'}$, iii) a cationic nucleophilic block copolymer $N^a$-A'-B' formed by organocatalyzed ring opening polymerization, iv) a base, optionally v) a nucleophilic non-charged amphiphilic block copolymer $N^c$-D'-E', v) a second crosslinking agent C''[—P''—$N^b$]$_{u'}$, optionally vi) a nucleophilic non-polymeric crosslinking agent S''[—$N^d$]$_{w'}$ and vii) a gene and/or a drug, wherein F' and F''' are electrophilic groups, and $N^a$, $N^b$, $N^c$, and $N^d$ are nucleophilic groups capable of reacting independently with F' and/or F''' to form a covalent bond; and allowing and/or inducing the mixture to crosslink, thereby forming the loaded hydrogel comprising i) the hydrogel of formula (1a) and ii) the gene and/or the drug occluded therein.

The cationic hydrogels can be prepared using the cationic nucleophilic block copolymer $N^a$-A'-B' in an amount of more than 0 mol %, more particularly 1 mol % to 60 mol %, 5 mol % to 52 mol % or more preferably 10 mol % to 52 mol % based on total combined moles of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent used to prepare the hydrogel. The total mol % of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent equals 100 mol %.

The cationic hydrogels can be prepared using the first crosslinking agent C'[—P'—F']$_{t'}$ in an amount of 15 mol % to 60 mol %, 20 mol % to 55 mol % or more preferably 25 mol % to 50 mol % based on total combined moles of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent used to prepare the hydrogel. The total mol % of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent equals 100 mol %.

The cationic hydrogels can be prepared using the second crosslinking agent C''[—P''—$N^b$]$_{u'}$ in an amount of 5 mol % to 70 mol %, 10 mol % to 60 mol % or more preferably 15 mol % to 50 mol % based on total combined moles of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent used to prepare the hydrogel. The total mol % of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent equals 100 mol %.

The cationic hydrogels can be prepared using the nucleophilic non-charged block copolymer $N^c$-D'-E' in an amount of 0 mol % to 20 mol %, 0 mol % to 10 mol %, or more preferably 0 mol % to 5 mol % based on total combined moles of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent. The total mol % of the first crosslinking agent, the second crosslinking agent, the cationic nucleophilic block copolymer, the nucleophilic non-charged block copolymer, the electrophilic non-polymeric crosslinking agent, and the nucleophilic non-polymeric crosslinking agent equals 100 mol %.

Preparation of the Nucleophilic Cationic Block Copolymer $N^a$-A'-B'.

The nucleophilic cationic block copolymer $N^a$-A'-B' can be prepared by organocatalyzed ring opening polymerization of one or more cyclic carbonyl monomers initiated by a poly(alkylene oxide) initiator. The ring opening polymerization produces a precursor block copolymer comprising a first repeat unit. The first repeat unit comprises a side chain leaving group capable of reacting with a tertiary amine to form a quaternary amine. Treatment of the precursor block copolymer with a tertiary amine produces a cationic nucleophilic block copolymer $N^a$-A'-B' comprising nucleophilic group $N^a$, a first block A' and a second block B', wherein block A' comprises a poly(alkylene oxide) backbone derived from the poly(alkeylene oxide) initiator. The poly(alkylene oxide) initiator comprises at least one nucleophilic initiator group. In an embodiment, the poly(alkylene oxide) initiator comprises two nucleophilic groups, wherein one of the two nucleophilic groups selectively initiates the ring opening polymerization. A second nucleophilic group of the poly(alkylene oxide) initiator can serve as the $N^a$ nucleophilic group that reacts with the above-described F' group to form linking group L' of the hydrogel.

In the following description of cyclic carbonyl monomers, the "first cyclic carbonyl monomer" comprises a monovalent leaving group capable of reacting with a tertiary amine to form a quaternary amine. The first repeat unit of block B' of the cationic nucleophilic block copolymer $N^a$-A'-B' is preferably derived from the first cyclic carbonyl monomer. The first cyclic carbonyl monomer can be stereospecific or non-stereospecific. An optional "second cyclic carbonyl monomer" is a non-charged cyclic carbonyl monomer that serves as a diluent for the first cyclic carbonyl monomer in order to adjust, for example, hydrophobicity and/or hydrophilicity of block B'. The second repeat unit of block B' of the cationic nucleophilic block copolymer $N^a$-A'-B' is preferably derived from the second cyclic carbonyl monomer. Second cyclic carbonyl monomers can be stereospecific or non-stereospecific. The first and/or second cyclic carbonyl monomers can be used singularly or in combination. That is, one or more different first cyclic carbonyl monomers and/or one or more different second cyclic carbonyl monomers can be used to prepare the cationic nucleophilic block copolymer.

The first cyclic carbonyl monomer and the second cyclic carbonyl monomer can be independently selected from cyclic esters, cyclic carbonates, cyclic carbamates, cylic ureas, cyclic thiocarbamates, cyclic thiocarbonates, and cyclic dithiocarbonates as shown in Table 4.

TABLE 4

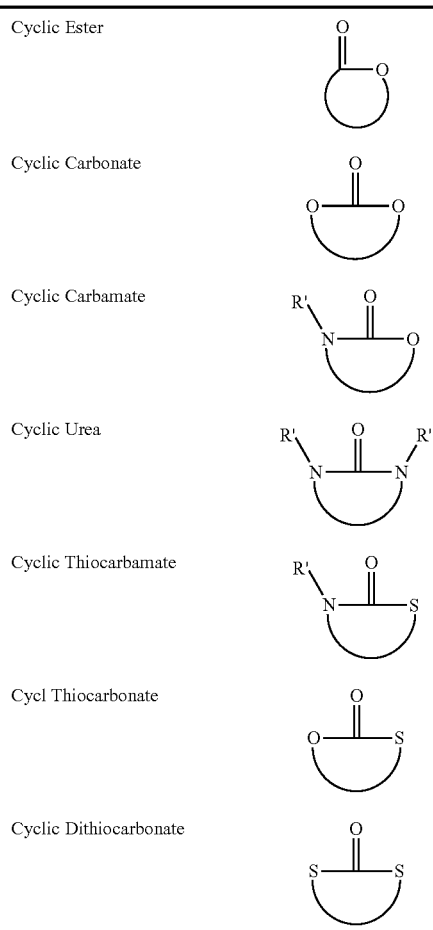

More specifically, the first and second cyclic carbonyl monomers can be selected independently from compounds of the general formula (8):

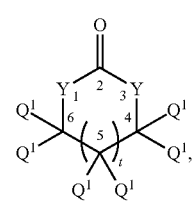
(8)

wherein t is an integer from 0 to 6, and when t is 0 carbons labeled 4 and 6 are linked together by a single bond. Each Y is a divalent radical independently selected from

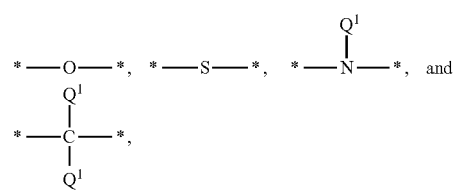

wherein the starred bond indicates the point of attachment. The latter two groups are also expressed herein as *—N $(Q^1)$-* and *—$C(Q^1)_2$-*. Each $Q^1$ is a monovalent radical independently selected from the group consisting of hydrogen, halides, alkyl groups comprising 1 to 30 carbons, aryl groups comprising 6 to 30 carbon atoms, and groups having the structure

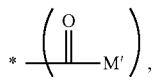

wherein M' is a monovalent radical selected from the group consisting of *-$R^1$, *—$OR^1$, *—$N(H)(R^1)$, *—$N(R^1)_2$, and *—$SR^1$, wherein the starred bond represents the point of attachment, and each $R^1$ is a monovalent radical independently selected from the group consisting of alkyl groups comprising 1 to 30 carbons and aryl groups comprising 6 to 30 carbons. One or more $Q^1$ groups can further comprise a monovalent leaving group capable of reacting with a tertiary amine to form a moiety comprising a quaternary amine (i.e., a positive charged quaternary ammonium ion bonded to four carbons). Non-limiting examples of monovalent leaving groups include halides in the form of an alkyl halide (e.g., alkyl chloride, alkyl bromide, or alkyl iodide), sulphonate esters (e.g., tosylate or mesylate esters), and epoxides. Each $Q^1$ group can independently be branched or non-branched. Each $Q^1$ group can also independently comprise one or more additional functional groups selected from the group consisting of ketones, aldehydes, alkenes, alkynes, cycloaliphatic rings comprising 3 to 10 carbons, heterocylic rings comprising 2 to 10 carbons, ethers, amides, esters, and combinations of the foregoing functional groups. A heterocyclic ring can comprise oxygen, sulfur and/or nitrogen. Two or more $Q^1$ groups can together form a ring. A first cyclic carbonyl monomer of formula (8) comprises one or more $Q^1$ groups comprising a monovalent leaving group capable of reacting with a tertiary amine to form a quaternary amine. The first cyclic carbonyl monomer can be stereospecific or non-stereospecific. A second cyclic carbonyl monomer of formula (8) does not comprise a monovalent leaving group capable of reacting with a tertiary amine to form a quaternary amine. In an embodiment, at least one Y group is *—O—*.

A ring opened polymer formed using a cyclic carbonyl monomer of formula (8) can have a backbone functional group selected from the group consisting of polyesters, polycarbonates, polyureas, polycarbamates, polythiocarbamates, polydithiocarbonates, and combinations thereof, which have a repeat structure as shown in Table 5.

TABLE 5

| Polyester | 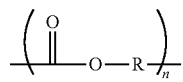 |
| Polycarbonate | 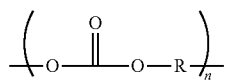 |
| Polyurea | 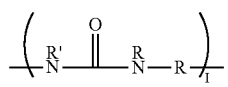 |
| Polycarbamate | 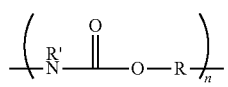 |

TABLE 5-continued

| Polythiocarbamate | 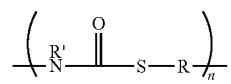 |
| Polythiocarbonate | 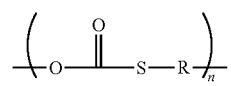 |
| Polydithiocarbonate | 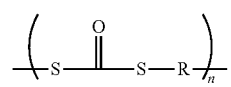 |

The ring opened polymer chain formed with a cyclic carbonyl monomer of formula (8) has a repeat unit having the general formula (9):

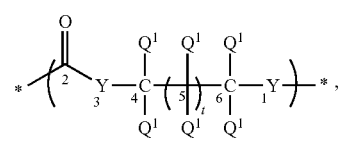

(9)

wherein Y, t, and $Q^1$ are defined as above, with backbone atoms numbered.

The first and second cyclic carbonyl monomers can be selected independently from compounds of the general formula (10):

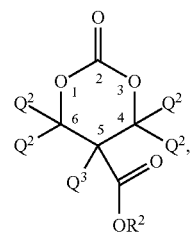

(10)

wherein $Q^2$ is a monovalent radical independently selected from the group consisting of hydrogen, halides, alkyl groups comprising 1 to 30 carbons, aryl groups comprising 6 to 30 carbon atoms, and groups having the structure

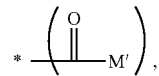

wherein M' is a monovalent radical selected from the group consisting of *-$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons, $R^2$ is a monovalent radical independently selected from the group consisting of alkyl groups comprising 1 to 30 carbons and aryl groups comprising 6 to 30 carbons, and $Q^3$ is a monovalent radical selected from the group consisting of hydrogen, alkyl groups having 1 to 30 carbons, and aryl groups having 6 to 30 carbons. In an embodiment, each $Q^2$ is hydrogen, and $Q^3$ is a methyl or ethyl group. A first cyclic carbonyl monomer of formula (10) comprises an $R^2$ group comprising a monovalent leaving group capable of reacting with a tertiary amine to form a moiety comprising a quaternary amine. A second cyclic carbonyl monomer of formula (10) does not comprise a monovalent leaving group capable of reacting with a tertiary amine to form a quaternary amine.

The ring opened polymer chain formed with a cyclic carbonyl monomer of formula (10) has a backbone carbonate repeat unit having the general formula (11):

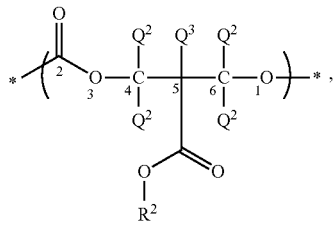

(11)

wherein $Q^2$, $Q^3$, and $R^2$ are defined as above. Backbone carbons and oxygens are numbered in formula (11).

The first and second cyclic carbonyl monomers can be selected from cyclic esters of the general formula (12):

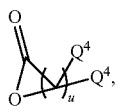

(12)

wherein u is an integer from 1 to 8, each $Q^4$ is a monovalent radical independently selected from the group consisting of hydrogen, halides, alkyl groups comprising 1 to 30 carbons, aryl groups comprising 6 to 30 carbon atoms, and groups having the structure

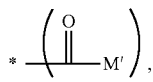

where M' is a monovalent radical selected from the group consisting of *—$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons. The lactone ring can optionally comprise a carbon-carbon double bond; that is, optionally, a

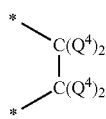

group of formula (12) can independently represent a

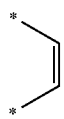

group. The lactone ring can also comprise a heteroatom such as oxygen, nitrogen, sulfur, or a combination thereof; that is, optionally a

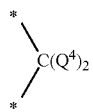

group of formula (12) can independently represent a *—O—*, *—S—*, *—N(H)—*, or an *—$N(R^1)$—* group, wherein $R^1$ has the same definition as above. A first cyclic carbonyl monomer of formula (12) comprises one or more $Q^4$ groups comprising a monovalent leaving group capable of reacting with a tertiary amine to form a moiety comprising a quaternary amine. The second cyclic carbonyl monomer of formula (12) does not comprise a monovalent leaving group capable of reacting with a tertiary amine to form a quaternary amine.

The ring opened polymer chain formed with a cyclic carbonyl monomer of formula (12) has a backbone ester repeat unit having the general formula (13):

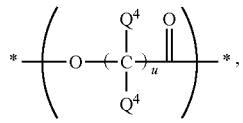

(13)

wherein $Q^4$ and u are defined as above.

The first and second cyclic carbonyl monomers can be selected from a dioxane dicarbonyl monomers of the general formula (14):

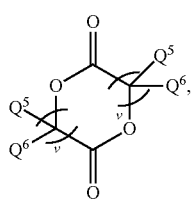

(14)

wherein each v is an independent integer from 1 to 6, each $Q^5$ is a monovalent radical independently selected from the group consisting of hydrogen, halides, carboxy groups, alkyl groups comprising 1 to 30 carbons, aryl groups comprising 6 to 30 carbon atoms, and groups having the structure

wherein M' is a monovalent radical selected from the group consisting of *-$R^1$, *—$OR^1$, *—$N(H)(R^1)$, *—$N(R^1)_2$, and *—$SR^1$, wherein each $R^1$ is a monovalent radical independently selected from the group consisting of alkyl groups comprising 1 to 30 carbons and aryl groups comprising 6 to 30 carbons, and each $Q^6$ is a monovalent group independently selected from the group consisting of hydrogen, alkyl groups having 1 to 30 carbons, and aryl groups having 6 to 30 carbons. A first cyclic carbonyl monomer of formula (14) comprises one or more $Q^5$ groups and/or a $Q^6$ groups comprising a monovalent leaving group capable of reacting with a tertiary amine to form a moiety comprising a quaternary amine. The second cyclic carbonyl monomer of formula (14) does not comprise a monovalent leaving group capable of reacting with a tertiary amine to form a quaternary amine.

The ring opened polymer chain formed with a cyclic carbonyl monomer of formula (14) has a backbone ester repeat unit having the general formula (15):

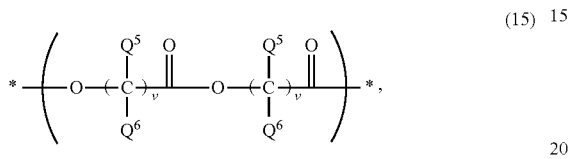
(15)

wherein $Q^5$, $Q^6$, and v are defined as above.

Examples of cyclic carbonyl monomers of formulas (8) or (10) having a monovalent leaving group in the form of an alkyl halide include the cyclic monomers of Table 6.

TABLE 6

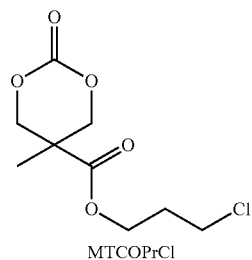
MTCOPrCl

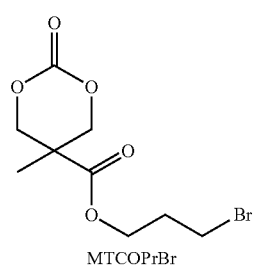
MTCOPrBr

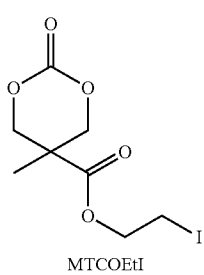
MTCOEtI

Additional examples of cyclic carbonyl monomers of formula (8) and (10) include the compounds of Table 7.

TABLE 7

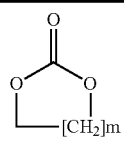
m = 1: Trimethylene carbonate (TMC)
m = 2: Tetramethylene carbonate (TEMC)
m = 3: Pentamethylene carbonate (PMC)

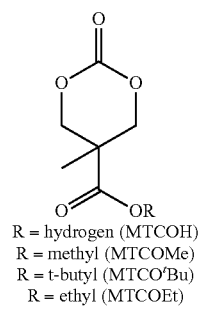
R = hydrogen (MTCOH)
R = methyl (MTCOMe)
R = t-butyl (MTCO$^t$Bu)
R = ethyl (MTCOEt)

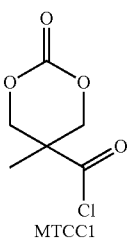
MTCCl

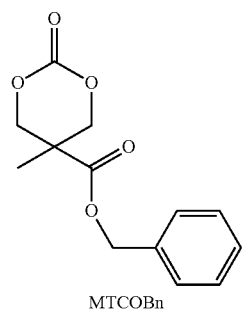
MTCOBn

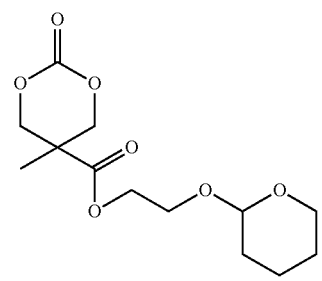 [SMILES: CC1(C(=O)OCCOC2CCCCO2)COC(=O)OC1]

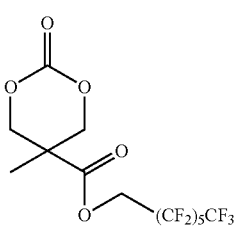
$(CF_2)_5CF_3$

TABLE 7-continued
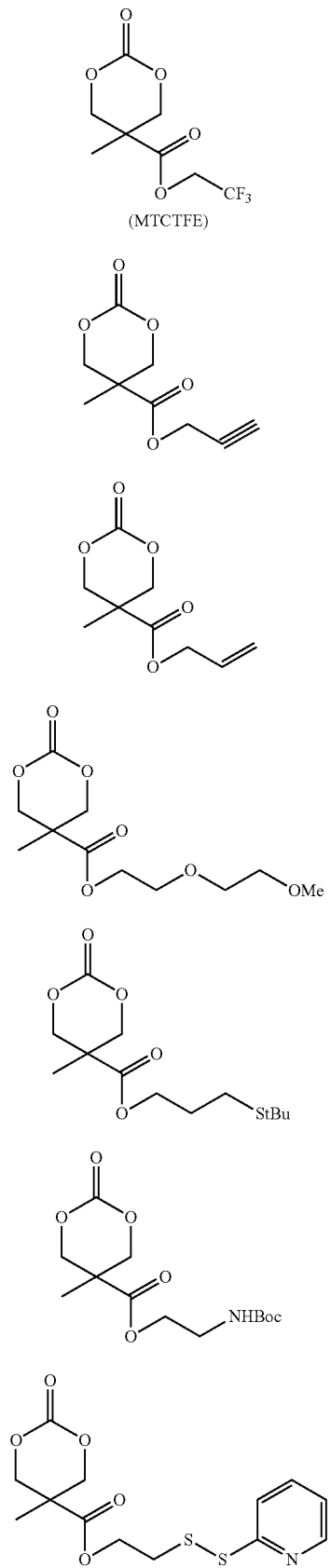
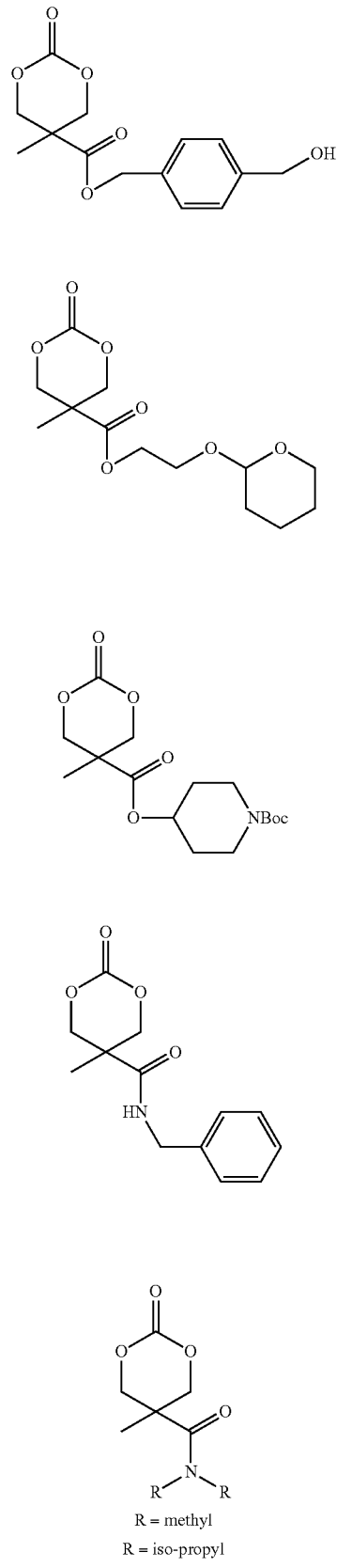

TABLE 7-continued

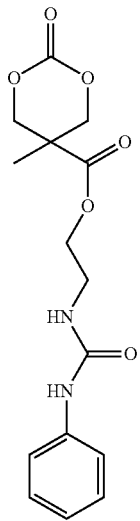 [SMILES: CC1(C(=O)OCCNC(=O)Nc2ccccc2)COC(=O)OC1]

MTCU

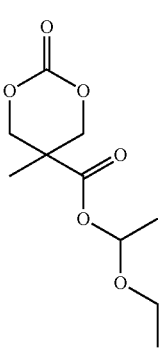 [SMILES: CCOC(C)OC(=O)C1(C)COC(=O)OC1]

MTCOEE

Examples of cyclic carbonyl monomers of formula (12) include the compounds of Table 8, and stereospecific versions thereof, where feasible, comprising one or more stereospecific asymmetric ring carbons.

TABLE 8

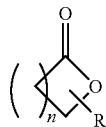

R = H, n = 1: beta-Propiolactone (b-PL)
R = H, n = 2: gamma-Butyrolactone (g-BL)
R = H, n = 3: delta-Valerolactone (d-VL)
R = H, n = 4: epsilon-Caprolactone (e-CL)
R = CH$_3$, n = 1: beta-Butyrolactone (b-BL)
R = CH$_3$, n = 2: gamma-Valerolactone (g-VL)

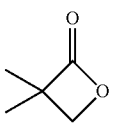

Pivalolactone
(PVL)

TABLE 8-continued

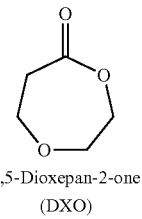

1,5-Dioxepan-2-one
(DXO)

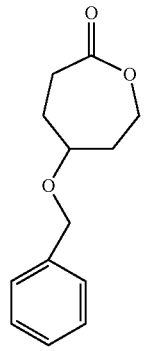 [SMILES: O=C1CCC(OCc2ccccc2)CCO1]

5-(Benzyloxy)oxepan-2-one
(BXO)

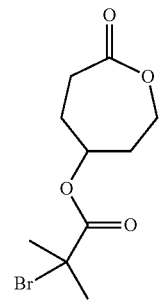

7-Oxooxepan-4-yl 2-bromo-2-methylpropanoate
(BMP-XO)

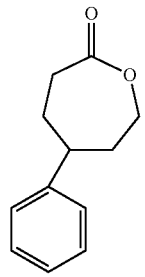 [SMILES: O=C1CCC(c2ccccc2)CCO1]

5-Phenyloxepan-2-one
(PXO)

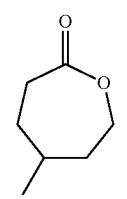

5-Methyloxepan-2-one
(MXO)

TABLE 8-continued

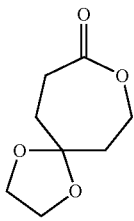 [SMILES: O=C1CCC2(CCO1)OCCO2]

1,4,8-Trioxa(4,6)spiro-9-undecane (TOSUO)

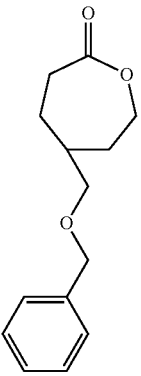 [SMILES: O=C1CCC(COCc2ccccc2)CCO1]

5-(Benzyloxymethyl)oxepan-2-one (BOMXO)

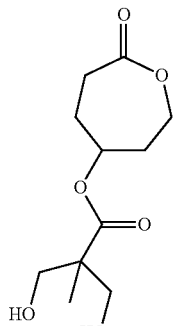

7-Oxooxepan-4-yl 3-hydroxy-2-(hydroxymethyl)-2-methylpropanoate (OX-BHMP)

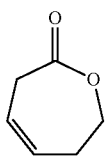

(Z)-6,7-Dihydrooxepin-2(3H)-one (DHXO)

Examples of cyclic carbonyl monomers of formula (14) include the compounds of Table 9.

TABLE 9

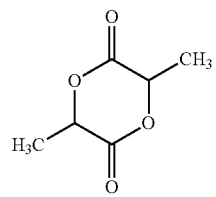

D-Lactide (DLA),
L-Lactide (LLA), or
racemic Lactide, 1:1 D:L forms (DLLA)

TABLE 9-continued

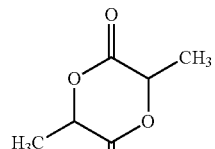

meso-Lactide (MLA)
(two opposite centers of assymetry, R and S)

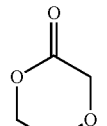

Glycolide (GLY)

In an embodiment, the first cyclic carbonyl monomer and the second cyclic carbonyl monomer are independently selected from the group consisting of cyclic carbonate monomers and cyclic ester monomers.

The above monomers can be purified by recrystallization from a solvent such as ethyl acetate or by other known methods of purification, with particular attention being paid to removing as much water as possible from the monomer. The monomer moisture content can be from 1 ppm to 10,000 ppm, 1 ppm to 1,000 ppm, 1 ppm to 500 ppm, and most specifically 1 ppm to 100 ppm, by weight of the monomer.

ROP Initiators.

Initiators for ring opening polymerizations generally include nucleophilic groups such as alcohols, primary amines, secondary amines, and thiols. The initiator can comprise one or more active nucleophilic initiator groups. The initiator can include protected nucleophilic groups that include protected thiols, protected amines, and protected alcohols. The initiator is preferably a polyether initiator, such as a poly(alkylene oxide) initiator. Exemplary polymeric mono-nucleophilic initiators include mono-endcapped poly (ethylene glycols), and mono-endcapped polypropylene glycols).

Dinucleophilic polyether initiators include poly(alkylene glycol) initiators of the general formula (16):

$$HO\text{---}[CH_2(CHR^1)_xCHR^1O]_n\text{---}H \qquad (16),$$

wherein x is 0 to 8, n is an integer from 2 to 10000, each $R^1$ is a monovalent radical independently selected from the group consisting of hydrogen, and groups comprising 1 to 10 carbons. Thus, the ether repeat unit can comprise 2 to 10 backbone carbons between each backbone oxygen. As non-limiting examples, the poly(alkylene glycol) can be a poly (ethylene glycol) (PEG), having the structure HO—[CH$_2$CH$_2$O]$_n$—H, a polypropylene glycol) (PPG), having the structure HO—[CH$_2$C(H)(CH$_3$)O]$_n$—H, or a mixture thereof.

Preferably, the polyether initiator is a hydrophilic dinucleophilic polyether material represented by the poly(alkylene oxide)s of general formula (17):

$$Z'\text{-}[CH_2CH(R^d)O]_n\text{---}Z'' \qquad (17)$$

wherein n is an integer from 2 to 10000, each $R^d$ in the chain is hydrogen or methyl, Z' is a monovalent radical selected from the group consisting of *—OH, *—SH, *—NH$_2$,

*—NH(R$^e$) and C$_1$-C$_{50}$ groups comprising a nucleophilic initiator group for ring opening polymerization wherein R$^e$ is hydrogen or C$_1$-C$_{10}$ alkyl, and Z" is a monovalent radical selected from the group consisting of hydrogen and C$_1$-C$_{50}$ groups comprising a nucleophilic initiator group for a ring opening polymerization. Preferably, Z' and Z" comprise different nucleophilic groups selected from alcohols, amines and thiols. In an embodiment, Z' comprises a thiol group and Z" comprises a hydroxy group.

Exemplary hydrophilic dinucleophilic polyether initiators include:

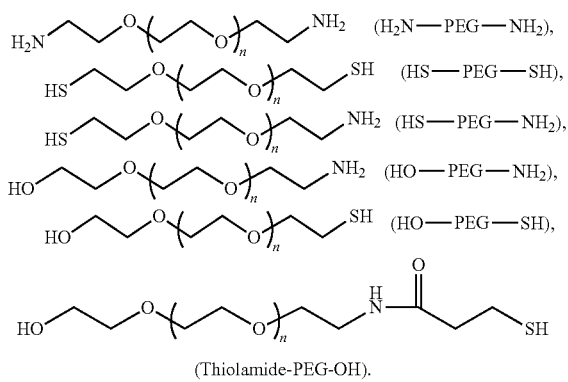

(Thiolamide-PEG-OH).

The dinucleophilic polyether initiator can have a number average molecular weight (Mn) of 100 to 100,000, more specifically 100 to 10000, and even more specifically, 100 to 5000.

Endcap Agents.

Endcapping the precursor block copolymer formed by the ring opening polymerization is optional. An endcap agent can prevent further chain growth and stabilize the reactive end groups, minimizing unwanted side reactions such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can also be a biologically active moiety.

Quaternization Reaction.

The precursor block copolymer comprises first repeat units derived from the first cyclic carbonyl monomer. The first repeat unit comprises a side chain moiety comprising a reactive monovalent leaving group capable of reacting with a tertiary amine to form a quaternary amine. The precursor block copolymer can be treated with a tertiary amine to form the cationic nucleophilic block copolymer. The quaternization reaction is accompanied by minimal, if any, crosslinking of the resulting cationic nucleophilic block copolymer. The quaternary nitrogen is preferably linked to a polymer side chain carbon. Alternatively, the quaternary nitrogen can be linked directly to a backbone carbon. The positively charged quaternary amine groups can provide binding strength to negatively charged biologically active materials.

No limitation is placed on the structure of the tertiary amine, providing the tertiary amine is capable of reacting with more than 0% of the monovalent leaving groups of the precursor block copolymer to form a quaternary amine. More preferably 10% or more, 20% or more, 30% or more, 40% or more, 50% or more, 60% or more, 70% or more, or 80% or more of the monovalent leaving groups of the precursor block copolymer react with the tertiary amine to form a quaternary amine.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic nucleophilic block copolymer will comprise first repeat units comprising a side chain moiety comprising a quaternary amine group and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell. The radioactive moiety can comprise a heavy metal radioactive isotope.

In an embodiment, the tertiary amine is a bis-tertiary amine, and the cationic nucleophilic block copolymer comprises a side chain moiety comprising a quaternary amine group and a tertiary amine group. The side chain tertiary amine groups can potentially provide buffering capacity to facilitate release of a biologically active material from the cationic hydrogel. Bis-tertiary amines have the general formula (18):

wherein L$^c$ is a divalent linking group comprising 2 to 30 carbons, and each monovalent R$^c$ group is independently selected from alkyl groups comprising 1 to 30 carbons or aryl groups comprising 6 to 30 carbons. Each R$^c$ group can independently be branched or non-branched. Each R$^c$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more R$^c$ groups can also together form a ring. Representative L$^c$ groups include *—(CH$_2$)$_{z'}$—* where z' is an integer from 2 to 30, *—(CH$_2$CH$_2$O)$_{z''}$CH$_2$CH$_2$—* where z" is an integer from 1 to 10, *—CH$_2$CH$_2$SCH$_2$CH$_2$—*, *—CH$_2$CH$_2$SSCH$_2$CH$_2$—*, *—CH$_2$CH$_2$SOCH$_2$CH$_2$—*, and *—CH$_2$CH$_2$SO$_2$CH$_2$CH$_2$—*. L$^c$ can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocyclic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The precursor block copolymer is treated with the tertiary amine in a suitable organic solvent, such as acetonitrile, dimethylsulfoxide (DMSO), dimethylformamide (DMF), combinations thereof, and the like, to form the cationic nucleophilic block copolymer. The reaction is conducted under anhydrous conditions, at ambient or elevated temperature using excess tertiary amine relative to the monovalent leaving group. In general, the tertiary amine is used in an amount of from 2 to 30 moles per mole of monovalent leaving group in the precursor block copolymer, more particularly 3 to 20 moles per mole of monovalent leaving group in the precursor block copolymer. The positive charged quaternary amine forms a salt with the displaced leaving group, which becomes a negatively charged counterion. Alternatively, the negatively charged counterion can be ion exchanged with another more suitable negatively charged counterion using known methods, if desired.

The cationic nucleophilic block copolymer can be isolated by removing excess solvent and amine by vacuum, or by precipitating the cationic nucleophilic block copolymer in an organic solvent such as tetrahydrofuran, followed by filtration and drying in vacuo. More than 0% of the first repeat units derived from the first cyclic carbonyl monomer comprise a side chain moiety comprising a quaternary amine group. When the precursor block copolymer is treated with a bis-tertiary amine, more than 0% of the first repeat units derived from the first cyclic carbonyl monomer comprise a side chain moiety comprising a quaternary amine group and a tertiary amine group. When the precursor block copolymer is treated with a tertiary amine comprising a carboxy group or a latent carboxylic acid group, more than 0% of the first repeat units derived from the first cyclic carbonyl monomer comprise the side chain moiety comprising the quaternary amine and a carboxylic acid or a latent carboxylic acid group. The quaternary amine group is present in the cationic nucleophilic block copolymer in an amount greater than 0% of the side chain monovalent leaving groups derived from the first cyclic carbonyl monomer. More particularly, the quaternary amine group is present in the cationic nucleophilic block copolymer in an amount of 10% to 100%, 20% to 100%, 30% to 100%, 40% to 100%, 50% to 100%, 60% to 100%, 70% to 100%, or 80% to 100% of the side chain monovalent leaving groups derived from the first cyclic carbonyl monomer. When the precursor block copolymer is treated with a bis-tertiary amine, the tertiary amine group can be present in the cationic nucleophilic block copolymer in an amount greater than 0% of the repeat units comprising a monovalent leaving groups of the precursor block copolymer, more particularly 10% to 100%, 20% to 100%, 30% to 100%, 40% to 100%, 50% to 100%, 60% to 100%, 70% to 100%, or 80% to 100% of the repeat units comprising a monovalent leaving groups of the precursor block copolymer.

Preparation of the Nucleophilic Non-Charged Block Copolymer N$^c$-D'-E'.

The optional nucleophilic non-charged block copolymer N$^c$-D'-E' can be prepared by organocatalyzed ring opening polymerization of cyclic carbonyl monomers. In an embodiment, block D' of the non-charged block copolymer comprises a poly(alkylene oxide) backbone, and block E' comprises a random copolycarbonate and/or copolyestercarbonate backbone and a repeat unit having a side chain urea group. In another embodiment, block E' is formed by organocatalyzed ring opening polymerization of MTCU, having the following structure.

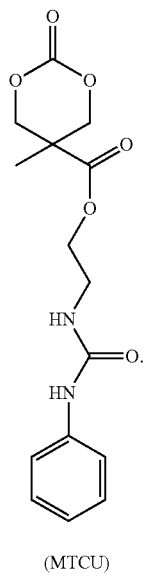

(MTCU)

Ring Opening Polymerizations (ROP).

The following description of methods, conditions and materials for ring opening polymerizations is applicable to the preparation of the cationic nucleophilic block copolymer and non-charged nucleophilic block copolymer.

The ring-opening polymerization can be performed at a temperature that is about ambient temperature or higher, 15° C. to 40° C., and more specifically 20° C. to 40° C. Reaction times vary with solvent, temperature, agitation rate, pressure, and equipment, but in general the polymerizations are complete within 1 hour to 100 hours.

The ROP reaction is preferably performed with a solvent. Solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter.

The ROP polymerizations are conducted under an inert (i.e., dry) atmosphere, such as nitrogen or argon, and at a pressure of from 100 MPa to 500 MPa (1 atm to 5 atm), more typically at a pressure of 100 MPa to 200 MPa (1 atm to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetra-ethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

The catalyst is preferably an organocatalyst whose chemical formula contains none of the restricted metals described further above. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexyl-thiourea (TU):

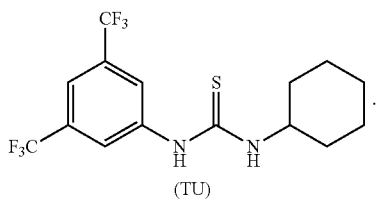

(TU)

Other ROP organocatalysts comprise at least one 1,1,1,3,3,3-hexafluoropropan-2-ol-2-yl (HFP) group. Singly-donating hydrogen bond catalysts have the formula (19):

R$^2$—C(CF$_3$)$_2$OH     (19), wherein R$^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 10.

TABLE 10

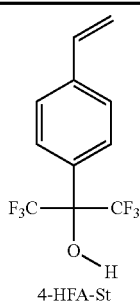

4-HFA-St

TABLE 10-continued

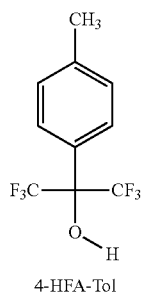

4-HFA-Tol

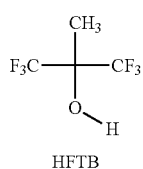

HFTB

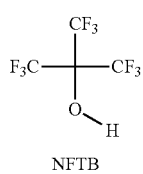

NFTB

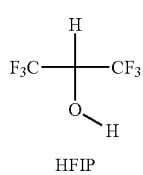

HFIP

Doubly-donating hydrogen bonding catalysts have two HFP groups, represented by the general formula (20):

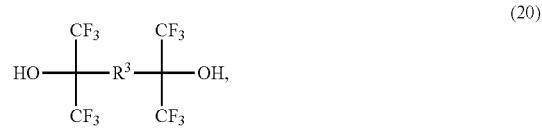

(20)

wherein R$^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (20) include those listed in Table 11. In a specific embodiment, R$^2$ is an arylene or substituted arylene group, and the HFP groups occupy positions meta to each other on the aromatic ring.

TABLE 11

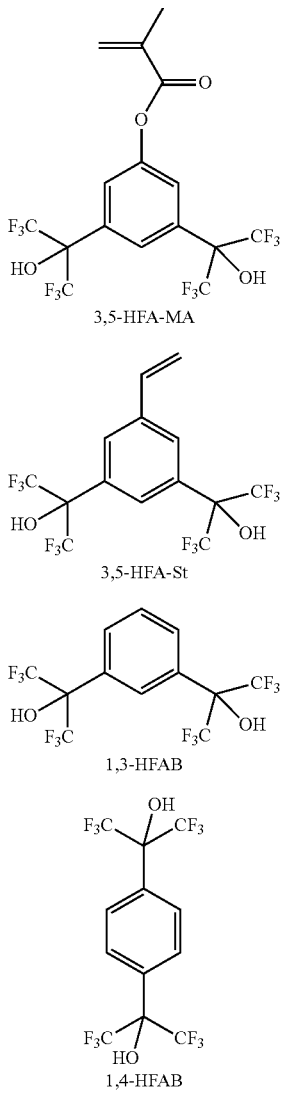

3,5-HFA-MA 3,5-HFA-St 1,3-HFAB 1,4-HFAB

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl(imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 12.

TABLE 12

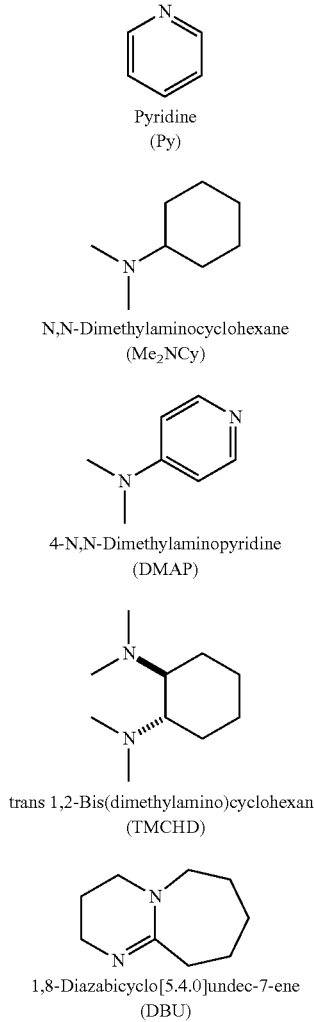

Pyridine (Py)

N,N-Dimethylaminocyclohexane (Me$_2$NCy)

4-N,N-Dimethylaminopyridine (DMAP)

trans 1,2-Bis(dimethylamino)cyclohexane (TMCHD)

1,8-Diazabicyclo[5.4.0]undec-7-ene (DBU)

TABLE 12-continued

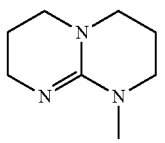

7-Methyl-1,5,7-triazabicyclo[4.4.0]dec-5-ene
(MTBD)

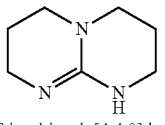

1,5,7-Triazabicyclo[4.4.0]dec-5-ene
(TBD)

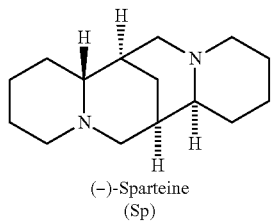

(−)-Sparteine
(Sp)

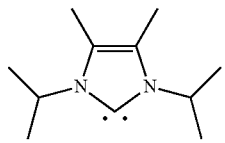

1,3-Bis(2-propyl)-4,5-dimethylimidazol-2-ylidene
(Im-1)

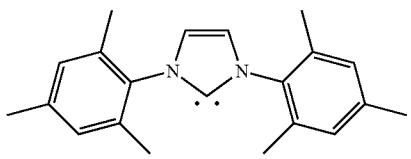

1,3-Bis(2,4,6-trimethylphenyl)imidazol-2-ylidene
(Im-2)

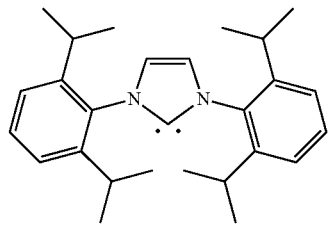 [SMILES: CC(C)c1cccc(C(C)C)c1N1C=CN(c2c(C(C)C)cccc2C(C)C)C1]

1,3-Bis(2,6-di-i-propylphenyl(imidazol-2-ylidene
(Im-3)

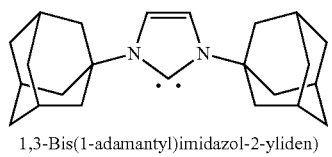

1,3-Bis(1-adamantyl)imidazol-2-yliden)
(Im-4)

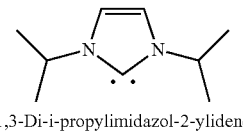

1,3-Di-i-propylimidazol-2-ylidene
(Im-5)

TABLE 12-continued

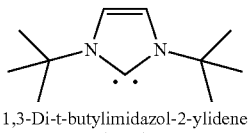

1,3-Di-t-butylimidazol-2-ylidene
(Im-6)

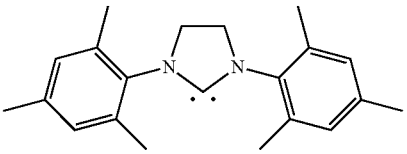

1,3-Bis(2,4,6-trimethylphenyl)-4,5-dihydroimidazol-2-ylidene
(Im-7)

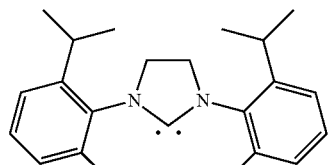

1,3-Bis(2,6-di-i-propylphenyl)-4,5-dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per participating nucleophilic initiator group in the ring opening polymerization. The participating initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has two participating hydroxyl initiator groups, the equivalent molecular weight per hydroxyl group is 50 g/mole. If the polymerization calls for 5 mol % reactive hydroxyl groups per mole of cyclic carbonyl monomers, the amount of initiator is 0.05×50=2.5 g per mole of cyclic carbonyl monomers. If the initiator has one participating hydroxyl initiator group and one non-participating thiol group, the equivalent molecular weight per participating initiator group is 100 g/mole. In an embodiment, the polyether initiator comprises two different non-protected initiator groups, and one of the two initiator groups initiates (i.e., participates) in the ring opening polymerization.

In a specific embodiment, the catalyst is present in an amount of about 0.2 mol % to 20 mol %, the nitrogen base accelerator is present in an amount of 0.1 mol % to 5.0 mol %, and the participating nucleophilic initiator groups of the initiator are present in an amount of 0.1 mol % to 5.0 mol % based on the equivalent molecular weight per participating nucleophilic initiator group of the initiator.

The catalysts can be removed by selective precipitation or in the case of the solid supported catalysts, simply by filtration. The precursor block copolymer can comprise residual catalyst in an amount greater than 0 wt. % (weight percent), based on total weight of the block copolymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the precursor block copolymer and the residual catalyst.

Average Molecular Weight.

The cationic nucleophilic block copolymer and/or the precursor block copolymer preferably have a number average molecular weight (Mn) as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the cationic nucleophilic block copolymer and/or the precursor block copolymer has a number average molecular weight of 10,000 g/mole to 20,000 g/mole. The cationic nucleophilic block copolymer and/or the precursor block copolymer also preferably has a narrow polydispersity index (PDI), generally from 1.01 to 2.0, more particularly 1.01 to 1.30, and even more particularly 1.01 to 1.25.

Industrial Applicability.

Hydrogels have found widespread application in the field of medicine particularly in wound healing, regenerative medicine, and decolonization of MRSA or other types of microbes. The antimicrobial activity of the disclosed compositions toward at least Gram-positive microbes can be attributed in part to the cationic charge density. The hydrogel forming materials described above can incorporate many types of chemical functionality heretofore unavailable in biodegradable hydrogel forming materials, providing a wider range of applications for these materials. The crosslinked structure of the hydrogels combined with their toxicity to microbes makes these materials attractive as antimicrobial layers, which can be disposed on a variety of medically useful substrates.

The substrate can have any shape or contour suitable for disposing the hydrogel precursor mixture. Substrates can comprise materials such as cloth, gauze, glass, metal, plastic, and combinations thereof. The substrate can be flexible such as a cloth or plastic tubing, rigid such as a metal instrument, 1-dimensional such as a needle, 2-dimensional such as a sheet material, or 3-dimensional such as a hand held medical instrument or an implanted mechanical device such as an artificial heart. The substrates can have a smooth surface or a topographical surface, such as in a woven fabric and/or gauze. The substrates can have rounded surfaces, such as the convex and concave surfaces of a tubular material. The surfaces of the substrate can be contoured. The substrate can comprise one or more layers. The substrate can include a surface layer to enhance adhesion of the hydrogel precursor mixture and/or the crosslinked hydrogel to the surface of the substrate.

The hydrogel precursor mixture is a fluid mixture capable of forming a coated film layer. The hydrogel precursor mixture preferably includes a solvent, which can include water and/or an organic solvent. The covalently crosslinked hydrogels can be formed in a single step by combining the above-described first crosslinking agent, the second crosslinking agent, and the cationic nucleophilic block copolymer in a hydrogel precursor mixture, and allowing or inducing (e.g., thermally, chemically, and/or photochemically) the hydrogel precursor mixture to form a covalently crosslinked hydrogel. Alternatively, the covalently crosslinked hydrogels can be formed sequentially by first forming an initial adduct of the cationic nucleophilic block copolymer and the first crosslinking agent, adding the second crosslinking agent to the initial adduct, thereby forming the hydrogel precursor mixture, and allowing or inducing the hydrogel precursor mixture to form a covalently crosslinked hydrogel. The hydrogel precursor mixture preferably includes a base, which can serve as a solvent, wherein the base has a pH effective in producing a crosslinked hydrogel in the coated film layer. In the examples further below, the hydrogels are formed in minutes at 37° C. and a pH of 8.0 using triethanolamine (TEOA) as a solvent.

In an exemplary method illustrated in the layer diagrams of FIG. 8, a hydrogel precursor mixture is disposed on an concave surface 14 (inner wall) of a tubular substrate 10. Air 16 is indicated. Tubular substrate 10 also has a convex surface 12 (outer wall) exposed to air 16. Depositing the hydrogel precursor mixture on concave surface 14 results in hydrogel precursor layer 22 comprising the hydrogel precursor mixture. Hydrogel precursor layer 22 has interface 24 with substrate 10 and concave surface 26 exposed to air 16. Hydrogel precursor layer 22 is allowed and/or induced to crosslink, thereby forming a covalently crosslinked hydrogel layer 32 disposed on tubular substrate 10. Hydrogel layer 32 has interface 34 with substrate 10 and concave surface 36 exposed to air 16.

In an extension of the above method, illustrated in the layer diagrams of FIG. 9, a hydrogel precursor mixture is disposed on the concave surface 14 (inner wall) and convex surface 12 (outer wall) of tubular substrate 10. Air 16 is indicated. Depositing the hydrogel precursor mixture on concave surface 14 and convex surface 12 produces hydrogel precursor layer 22 comprising the hydrogel precursor mixture and hydrogel precursor layer 42 comprising the hydrogel precursor mixture. Hydrogel precursor layer 22 has interface 24 with substrate 10 and concave surface 26 exposed to air 16. Hydrogel precursor layer 42 has interface 44 with tubular substrate 10 and convex surface 46. Hydrogel precursor layers 22 and 42 are allowed and/or induced to crosslink, thereby forming, respectively, covalently crosslinked hydrogel layer 32 disposed on concave surface 14 of tubular substrate 10 and covalently crosslinked hydrogel layer 52 disposed on convex surface 12 of tubular substrate 10. Hydrogel layer 32 has interface 34 with tubular substrate 10 and concave surface 36 exposed to air 16. Hydrogel layer 52 has interface 54 with tubular substrate 10 and convex surface 56 exposed to air 16.

FIG. 10A illustrates a two-dimensional flexible woven substrate 100 comprising threads 102, such as would be used in a wound dressing. FIG. 10B is a series of layer diagrams showing a method of coating woven substrate 100 using an end on view of one of the threads 102, which comprises surface 104 exposed to air. Thread 102 can be porous or non-porous, and can comprise a natural (e.g., cotton) and/or synthetic material (e.g., polyester, nylon, etc.). The hydrogel precursor mixture is deposited on thread 102, thereby forming hydrogel precursor layer 110 disposed on thread 102. Hydrogel precursor layer 110 has interface 114 with thread 102, and surface 116 exposed to air. The hydrogel precursor layer 110 is allowed and/or induced to crosslinked, thereby forming crosslinked hydrogel layer 120 disposed on thread 102, having interface 124 with thread 102, and surface 126 exposed to air.

The hydrogel precursor mixture can be deposited on a substrate using any suitable technique, for example dip coating, brush coating, injection coating, spin coating, spray coating, and combinations thereof.

The substrate can be a medical device. Medical devices include swabs, catheters, sutures, stents, bedpans, gloves, facial masks, absorbent pads, absorbent garments, internal absorbent devices, and insertable mechanical devices, which can include artificial organs. In an embodiment, an article comprises the covalently crosslinked hydrogel disposed on a surface of a medical device. In another embodiment the medical device is a catheter. In another embodiment, the medical device is a material suitable for a wound dressing, such as gauze.

Dressings for wound healing have become an important area of research particularly for the treatment of burns, battlefield injuries, surgical and diabetic wounds, and other injuries. Dressings are designed to prevent loss of fluids, mitigate bacterial infection and accelerate tissue regeneration. The material requirements for such a dressing are stringent and include gas permeability, mechanical integrity and the ability to control water uptake/loss. The dressing should be easy to apply, cure or set rapidly, and adhere to the desired substrate. The dressing should show no systemic toxicity, should be comfortable, and should be easy to remove without damaging underlying tissue. The most commonly used wound dressings are gauze that tends to become trapped in the nascent tissue making the eventual removal difficult and painful. Dressings that have to be changed frequently often remove epithelial cells that have proliferated and migrated to the dressing material causing secondary damage to the wound. The hydrogels can encapsulate cells such as human dermal fibroblasts or keratinocytes to accelerate the wound healing process. Furthermore, the disclosed hydrogels can be substantially or wholly biodegradable. Therefore, they can be used for healing of various types of wounds.

Another critical component to a wound-dressing design is the ability to fight bacterial infection. Due to the increasing resistance of bacteria to conventional antibiotics, macromolecular peptide-based antimicrobial agents have received significant attention. Cationic peptides (e.g., magainins, cecropins, protegrins and defensins) do not have a specific target in microbes, and they interact with microbial membranes based on electrostatic interaction, thereby inducing damage to the microbial membranes, which is hard to repair.

The disclosed crosslinked hydrogels contain pendant cationic block copolymers that can inhibit growth of microbes. Therefore, they can also be used for prevention and treatment of infections that occur in catheters caused by drug-resistant microbes such as methicillin-resistant *Staphylococcus aureus* (MRSA). A central venous catheter is widely used in many patients who have chronic diseases. To prevent infections of the catheter, chlorhexidine-impregnated disk or sponge that is slipped over the central catheter during insertion is used, which lasts for about a week. However, chlorhexidine is a small molecular antibiotic, and chlorhexidine resistance in bacteria has been reported. Central venous catheter surfaces having a crosslinked hydrogel surface layer can help to prevent MRSA infections.

The examples below demonstrate that compositions comprising crosslinked hydrogels that comprise a pendant cationic block copolymer, have strong antimicrobial activity against Gram-negative microbes, such as *Escherichia coli*, and Gram-positive microbes, such as *Staphylococcus aureus*, fungi, and yeast. In an embodiment, a method comprises contacting a microbe with the composition, thereby killing the microbe.

The hydrogel precursor mixture and the crosslinked hydrogel formed therefrom can include a biologically active material, such as a drug and/or a gene. The biologically active material can be bound covalently and/or non-covalently to the crosslinked hydrogel. The crosslinked hydrogel can be a controlled release vehicle for the biologically active material.

Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diclofenac, Diclofenac Sodium Salt (DCF), Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraprod®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AVD, Prednisolone, Prednisone, Prelone®, Procarbazine, PRO-CRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Charge Shifting.

The release of a biologically active material from the crosslinked hydrogel can be facilitated by pendant cationic block copolymers capable of charge-shifting. In charge shifting, the net positive charge of the pendant cationic block copolymer is reduced by the conversion of a non-charged group on the pendant cationic block copolymer side chain into a negatively charged group. A pendant cationic block copolymer capable of charge-shifting can comprise, for example, a latent carboxylic acid group, such as an acetal ester, in addition to the quaternary amine. The acetal ester group has the general formula (21):

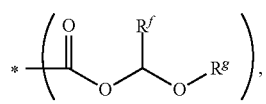

(21)

wherein the starred bond represents the attachment point to a cyclic carbonyl moiety, and $R^f$ and $R^g$ are monovalent radicals independently comprising from 1 to 20 carbons. In an embodiment, $R^f$ is methyl and $R^g$ is ethyl. In another embodiment, a second cyclic carbonyl monomer is MTCOEE:

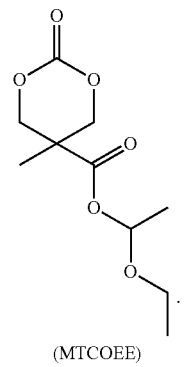 [SMILES: CCOC(C)OC(=O)C1(C)COC(=O)OC1]

(MTCOEE)

Acetal esters can be hydrolyzed under the mildly acidic conditions (about pH 5) to form a carboxylic acid group. The carboxylic acid groups can become ionized, thereby lowering the net positive charge of the hydrogel and allowing the release of a negatively charged biologically active material from the hydrogel. Thus, the hydrogels can be easily modified to tune the charge and the buffering strength for a specific biologically active material.

Another strategy for facilitating release of a biologically active material involves non-covalent interactions to stabilize a biologically active cargo, for example, using diluent cyclic carbonyl monomers comprising a fluorinated tertiary alcohol group. Fluorinated tertiary alcohol groups are known to bind to phosphates and related structures, but with interaction energies that are lower than electrostatic interactions, and hence more easily released.

Other functional groups can be used to facilitate the release of the biologically active material from the crosslinked hydrogel, such as secondary amine groups, citraconic amide groups, ester groups, and imine groups.

The following examples demonstrate the preparation and uses of the crosslinked hydrogels comprising a pendant cationic block copolymer produced by organocatalytic ring-opening polymerization.

EXAMPLES

Materials used in the following examples are listed in Table 13.

TABLE 13

| ABBREVIATION | DESCRIPTION[a] | SUPPLIER |
|---|---|---|
| 4Arm-PEG-OH | C[CH$_2$O(CH$_2$CH$_2$O)$_{m-1}$CH$_2$CH$_2$OH]$_4$ Mw 10,000, sold under the tradename 4-Arm PEG-OH, m is approximately 55 | Creative PEGWorks, USA |
| 4Arm-PEG-SH | C[CH$_2$O(CH$_2$CH$_2$O)$_{m'}$CH$_2$CH$_2$SH]$_4$ Mw 10,000; sold under the tradename 4Arm PEG-sulfhydryl, m' is approximately 54. | Sunbio (South Korea) |
| Thiolamide-PEG-OH | HS—CH$_2$CH$_2$C(=O)NH(CH$_2$CH$_2$O)$_n$H Mn 5000, PDI 1.03 dinucleophilic initiator, n is approximetely 112. | RAPP Polymere GmbH |
| BisMPA | 2,2-Bis(hydroxymethyl)propionic acid | Sigma-Aldrich |
| DBU | 1,8-Diazabicyclo[5.4.0]undec-7-ene | Sigma-Aldrich |

TABLE 13-continued

| ABBREVIATION | DESCRIPTION[a] | SUPPLIER |
| --- | --- | --- |
| TU | N-bis(3,5-Trifluoromethyl)phenyl-N'-cyclohexylthiourea | Prepared below |
| Sparteine | (6R,8S,10R,12S)-7,15-Diazatetracyclo[7.7.1.0$^{2,7}$.0$^{10,15}$]heptadecane | Sigma-Aldrich |
| TEOA | Triethanolamine | Merck, Singapore |
| PBS | Phosphate Buffered Saline | Invitrogen |
| TSB | Tryptic Soy Broth | Becton, Dickinson and Co., USA |
| TMEDA | N,N,N',N'-tetramethylethylenediamine | Merck, Singapore |
| TCTP | Tissue Culture Plate, Nunc MicroWell ™ Treated Polystyrene (Catlog No. 167008) | Nunc |
| DCF | Diclofenac Sodium Salt, MW 318.13 | Sigma-Aldrich |
| PETA | Pentaerythritol Tetraacrylate, MW 318.13 | Sigma-Aldrich |

[a]Herein, Mn is the number average molecular weight. Mw is the weight average molecular weight. MW is molecular weight.

Acryloyl chloride, diethyl ether, triethylamine (TEA), KOH and N,N,N',N'-tetramethylethylenediamine (TMEDA) were purchased from Merck, Singapore. Anhydrous dichloromethane (DCM), DMF, THF and pyridine were purchased from Sigma-Aldrich. 2,2-Bis(hydroxymethyl)propionic acid (bisMPA), benzyl bromide (BnBr), triphosgene and Pd/C (10%) were purchased from Sigma-Aldrich. 1,8-Diazabicyclo[5.4.0]undec-7-ene (DBU) was dried with CaH$_2$ overnight and distilled under reduced pressure before stored in a glove box. *Staphylococcus aureus* (*S. aureus*), *Escherichia coli* (*E. coli*) and *Candida albicans* (*C. albicans*) were purchased from ATCC. All other chemicals were of analytical grade, and used as received.

N-bis(3,5-trifluoromethyl)phenyl-N'-cyclohexylthiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over CaH$_2$, filtering, and removing solvent under vacuum.

Polymer Characterization.

The nuclear magnetic resonance ($^1$H-NMR) spectra of the polymers were studied using a Bruker Avance 400 spectrometer (400 MHz), and chloroform-d (CDCl$_3$) was used as the solvent. The molecular weights and polydispersity indices were determined by a gel permeation chromatography (GPC) (Waters 2690, MA, USA, mobile phase: THF at 1.0 ml/min, relative to polystyrene standards).

I. Monomer Syntheses.

A particularly useful synthon for functional biodegradable monomers is so-called MTC family of cyclic carbonate monomer derived from 2,2-bis(methylol)propionic acid (bisMPA). BisMPA provides a facile route to 5-methyl-5-carboxyl-1,3-dioxan-2-one (MTCOH) and derivative thereof, as shown in Scheme 1.

Scheme 1.

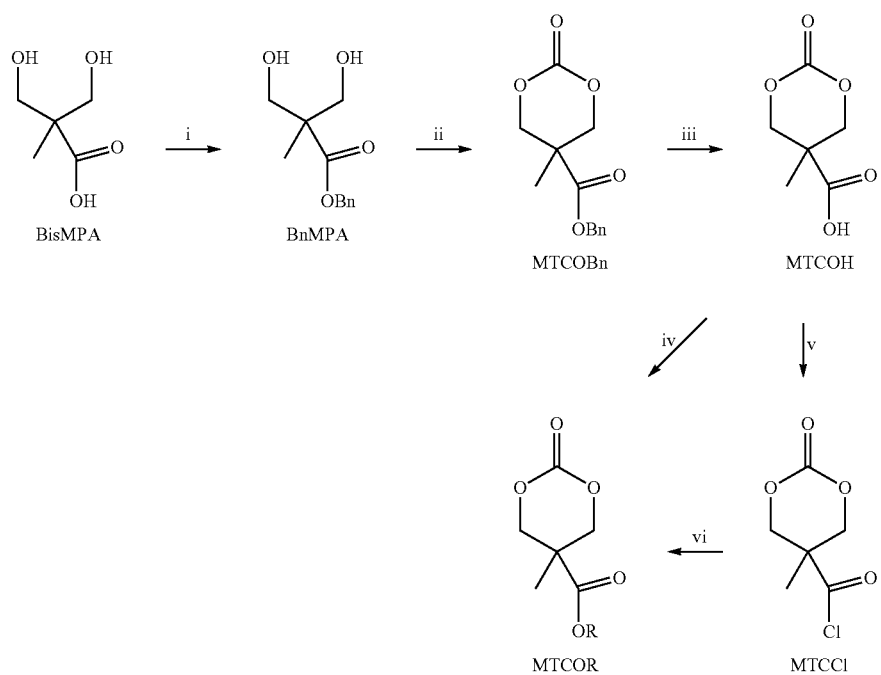

This approach parallels that of (meth)acrylate derivatization and has been demonstrated to create a wide selection of functional monomers capable of undergoing ring-opening polymerization. 2,2-Bis(methylol)propionic acid (bisMPA) can be first converted (i) to a benzyl ester BnMPA (herein also used as an initiator for the polymerizations), followed by reaction (ii) of BnMPA with triphosgene to form a cyclic carbonyl monomer, MTCOBn. MTCOBn is debenzylated (iii) to produce the cyclic carbonyl carboxylic acid, MTCOH. Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCCl followed by treatment (vi) of MTCCl with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bisMPA; (ii) triphosgene, pyridine, $CH_2Cl_2$, −78° C. to 0° C., 95% yield of MTCOBn; (iii) Pd/C (10%), H2 (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCCl; (vi) ROH, $NEt_3$, RT, 3 hours yields MTCOR.

The preparation of cyclic carbonate haloesters MTCOPrBr, MTCOPrCl, MTCOEtI by reaction of MTCCl with 3-bromopropanol, 3-choloropropanol, and 2-iodoethanol, respectively, are described below. The haloesters were purified by either recrystallization or by flash chromatography (ethyl acetate/hexane) in high yields (>85%).

Example 1

Preparation of 5-methyl-5-(3-chloropropyl)oxycarboxyl-1,3-dioxan-2-one, (MTCOPrCl), molecular weight 236.65

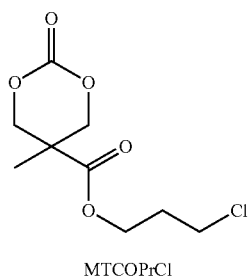

MTCOPrCl

A catalytic amount (3 drops) of DMF was added to a THF solution (200 mL) of MTCOH (11.1 g, 69 mmol), followed by a solution of oxalyl chloride (7.3 mL, 87 mmol) in THF (100 mL), gently added over 20 min under $N_2$ atmosphere. The solution was stirred for 1 hour, bubbled with $N_2$ flow to remove volatiles, and evaporated under vacuum to give the intermediate MTCCl. A mixture of 3-chloro-1-propanol (5.4 mL, 76 mmol) and pyridine (6.2 mL, 65 mmol) in dry THF (50 mL) was added dropwise to a dry THF solution (100 mL) of the intermediate MTCCl over 30 min, while maintaining a solution temperature below 0° C. with an ice/salt bath. The reaction mixture was kept stirring for another 3 hours at room temperature before it was filtered and the filtrate evaporated. The residue was dissolved in methylene chloride and washed with 1N HCl aqueous solution, saturated $NaHCO_3$ aqueous solution, brine and water, stirred with $MgSO_4$ overnight, and the solvent evaporated. The crude product was passed through a silica gel column by gradient eluting of ethyl acetate and hexane (50/50 to 80/20) to provide the product as a colorless oil that slowly solidified to a white solid (9.8 g, 60%).

Example 2

Preparation of 5-methyl-5-(3-bromopropyl)oxycarboxyl-1,3-dioxan-2-one, (MTCOPrBr), molecular weight 281.10

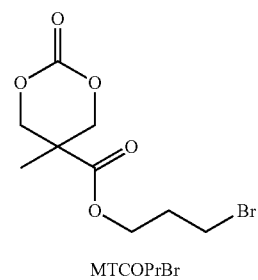

MTCOPrBr

MTCOPrBr was prepared by the procedure of Example 1 on a 45 mmol scale using 3-bromo-1-propanol as the alcohol. The product was purified by column chromatography, and subsequently recrystallized to yield white crystals (6.3 g, 49%). $^1$H NMR (400 MHz, $CDCl_3$): delta 4.69 (d, 2H; $CH_2OCOO$), 4.37 (t, 2H; $OCH_2$), 4.21 (d, 2H; $CH_2OCOO$), 3.45 (t, 2H; $CH_2Br$), 2.23 (m, 2H; $CH_2$), 1.33 (s, 3H; $CH_3$). $^{13}$C NMR (100 MHz, $CDCl_3$): delta 171.0, 147.3, 72.9, 63.9, 40.2, 31.0, 28.9, 17.3.

Example 3

Preparation of 5-methyl-5-(2-iodoethyl)oxycarboxyl-1,3-dioxan-2-one, (MTCOEtI), molecular weight 314.08

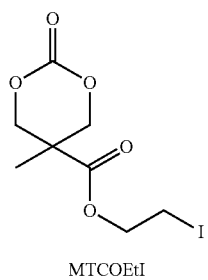

MTCOEtI

MTCOEtI was prepared by the procedure of Example 1 on a 45 mmol scale, using 2-iodoethanol as the alcohol, and was purified by column chromatography and subsequent recrystallization to yield yellowish crystals (7.7 g, 54%). $^1$H NMR (400 MHz, CDCl$_3$): delta 4.73 (d, 2H; CH$_2$OCOO), 4.45 (t, 2H; OCH$_2$), 4.22 (d, 2H; CH$_2$OCOO), 3.34 (t, 2H; CH$_2$I), 1.38 (s, 3H; CH$_3$). $^{13}$C NMR (100 MHz, CDCl$_3$): delta 170.5, 147.3, 72.8, 65.6, 40.3, 17.5, −0.3.

MTCOEt was prepared from bisMPA as a non-functional counterpart for dilution effects and to introduce hydrophobic repeat units in the polycarbonate chain.

Example 4

Preparation of Ethyl 2,2-bis(methylol)propionate (EtMPA), Molecular Weight 162.2

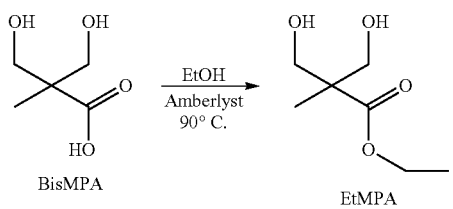

2,2-Bis(methylol)propionic acid (bisMPA; molecular weight 134.1, 22.1 g, 0.165 mol) was added in ethanol (150 mL) with Amberlyst-15 (6.8 g) and refluxed overnight. The resins were then filtered out and the filtrate was evaporated. Methylene chloride (200 mL) was added to the resulting viscous liquid to filtrate the unreacted reagent and byproduct. After the solution was dried over MgSO$_4$ and evaporated, ethyl 2,2-bis(methylol)propionate (EtMPA) was obtained as a clear and colorless liquid (21.1 g, 86%).

Example 5

Preparation of 5-methyl-5-ethyloxycarbonyl-1,3-dioxan-2-one (MTCOEt), molecular weight 188.2

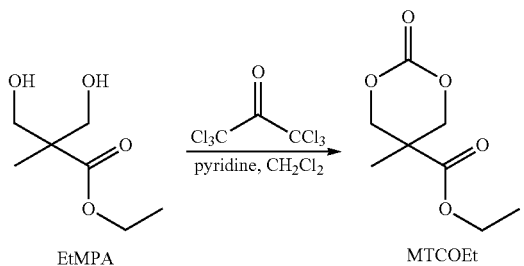

A solution of triphosgene (19.5 g, 0.065 mol) in CH$_2$Cl$_2$ (200 mL) was added stepwise to a CH$_2$Cl$_2$ solution (150 mL) of ethyl 2,2-bis(methylol)propionate (EtMPA) (21.1 g, 0.131 mol) and pyridine (64 mL, 0.786 mol) over 30 min at −75° C. with dry ice/acetone. The reaction mixture was kept stirring for another 2 hours under chilled condition and then allowed to heat to room temperature. Saturated NH$_4$Cl aqueous solution (200 mL) was added to the reaction mixture to decompose excess triphosgene. The organic phase was then treated with 1 N HCl aq (200 mL), followed by saturated NaHCO$_3$ (200 mL), brine (200 mL), and water (200 mL). After the CH$_2$Cl$_2$ solution was dried over MgSO$_4$ and evaporated, the residue was recrystallized from ethyl acetate to give white crystals (13.8 g, 56%). $^1$H NMR: delta 4.68 (d, 2H, CH$_2$OCOO), 4.25 (q, 1H, OCH$_2$CH$_3$), 4.19 (d, 2H, CH$_2$OCOO), 1.32 (s, 3H, CH$_3$), 1.29 (t, 3H, CH$_3$CH$_2$O). $^{13}$C NMR: delta 171.0, 147.5, 72.9, 62.1, 39.9, 17.3, 13.8. HR-ESI-MS: m/z calcd for C$_8$H$_{12}$O$_5$; Na, 211.0582; found, 221.0578.

Example 6

Preparation of 4Arm-PEG-Acrylate

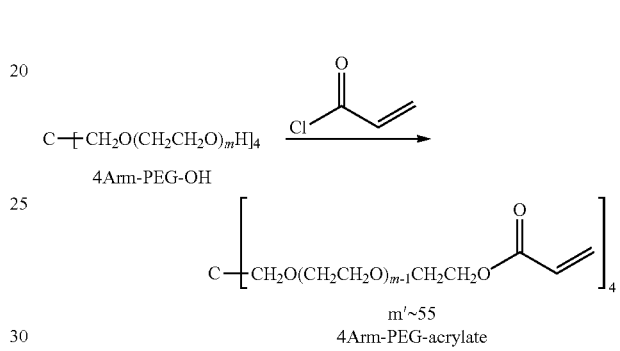

4Arm-PEG-acrylate was prepared by reacting 4Arm-PEG-OH with acryloyl chloride in DCM in the presence of TEA. 4Arm-PEG-OH (Mw 10,000, 8 g, 0.8 mmol) was dissolved in 200 mL of anhydrous DCM, and the trace water in the system was removed through azeotropic distillation. The flask was then cooled to room temperature and triethylamine (TEA) (1.5 mL, 13.2 molar equivalents) was added. Acryloyl chloride (12 molar equivalents) in DCM was then added dropwise to the flask. The reaction was allowed to proceed at room temperature under a nitrogen atmosphere for 24 hours. The reaction mixture was filtered, and excess diethyl ether was added to the filtrate to precipitate the product. The polymer was further precipitated twice in diethyl ether, filtered and dried in a vacuum oven. The chemical structure of the product was verified by $^1$H-NMR spectrum. The presence of vinyl group was identified by the characteristic protons CHCH$_2$ at delta 6.1 and CHCH2 at delta 5.8 and 6.4 in the $^1$H-NMR spectrum. The degree of conversion of hydroxyl group to acrylate group was found to be 95%, which was determined by comparing the integrated areas corresponding to OCH2CH2O and CHCH2 respectively.

II. Ring Opening Polymerizations.

Examples 7 to 10

Synthesis and characterization of cationic polycarbonate block copolymers, also referred to as aminated polycarbonates APC-x-y (x and y representing numbers of repeat units), was accomplished in two steps.

The first step is the ring opening polymerization of the cyclic carbonate monomers as shown in Scheme 2 to form a precursor block copolymer PCP-x-y.

Scheme 2.

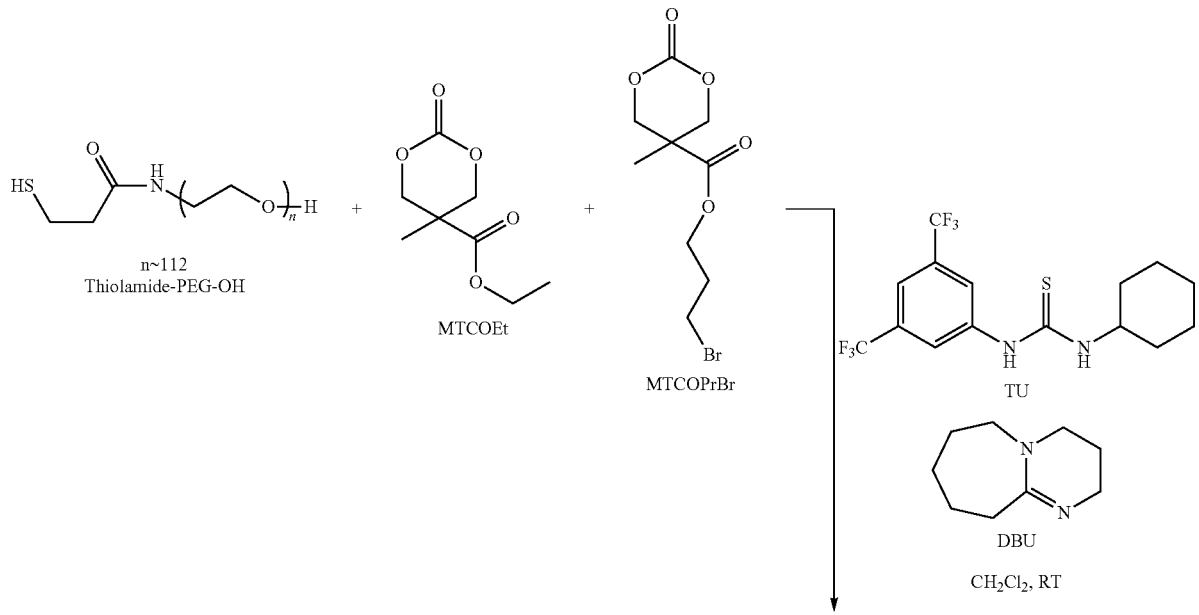

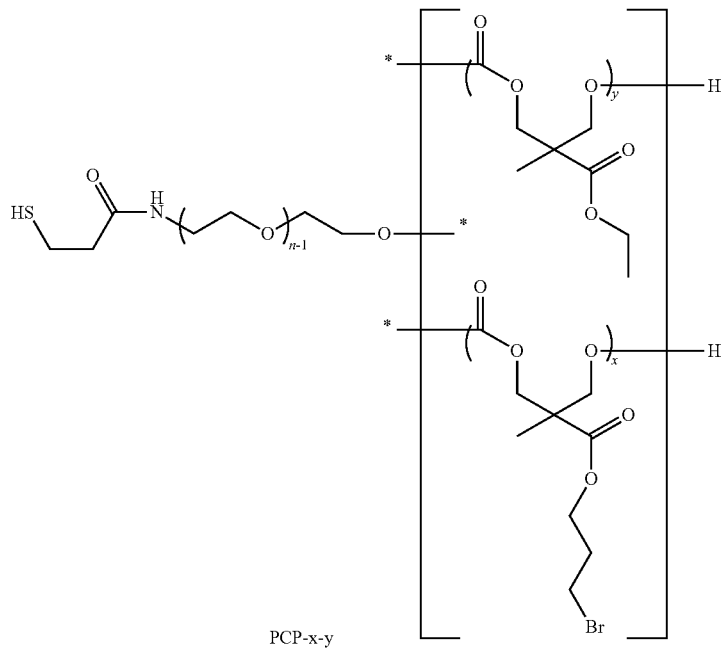

PCP-x-y

The ring opening polymerization was conducted using cyclic carbonate monomers MTCOEt and MTCOPrBr as polymer chain building blocks, thiolamide-PEG-OH (Mn 5,000 Dalton, PDI 1.03) as a macroinitiator, and Lewis acid N-bis(3,5-bis(trifluoromethyl)phenyl)-N'-cyclohexylthiourea (TU) with the Lewis base 1,8-diazabicyclo[5.4.0]undec-7-ene (DBU) (1:1 m/m) as cocatalysts. Thiolamide-PEG-OH comprises a linear poly(ethylene oxide) chain terminated on a first end unit with a hydroxy group and on a second end unit with a beta-thiopropionamide group. The subscripts "x" and "y" in the name PCP-x-y represent NMR analyzed numbers of repeat units derived from MTCOPrBr and MTCOEt, respectively, in the polycarbonate block formed by the ring opening polymerization. The vertical brackets in the block polymer structure of Scheme 2 indicate the polycarbonate chain is a random copolymer comprising the stacked repeat units within the brackets. Using the polymerization conditions described below, it was unexpectedly found that the thiol group of the thiolamide-PEG-OH does not initiate a ring opening polymerization of MTCOPrBr and/or MTCOEt. This finding allowed direct formation of a functionalized polycarbonate block copolymer having a terminal thiol group without the additional steps of protecting and deprotecting the thiol group.

The following procedure for preparing the precursor block copolymer PCP-18-10 is representative. A 20 mL glass vial equipped with a stir bar was charged in a glove-box with thiolamide-PEG-OH initiator (0.3 mg, 0.06 mmol, Mn 5000 Dalton, PDI 1.03, degree of polymerization (DP) approximately 112), MTCOPrBr (0.338 g, 1.2 mmol, for an aim DP of 20), and MTCOEt (0.113 g, 0.6 mmol, for an aim DP of 10, y=10 in the structure above). Dichloromethane was added and the concentration was adjusted to 2 M. TU (22.2 mg, 0.06 mmol) and DBU (9 microliters, 0.06 mmol) were added to the clear solution to initiate the polymerization. The polymerization was allowed to proceed for five hours at room temperature (18° C. to 27° C.), after which 5 mg to 10 mg of benzoic acid was added to quench the polymerization. The solution of the crude product was removed from the glove-box and the product diblock copolymer comprising a side chain haloester group was precipitated in cold methanol. The precipitate was allowed to settle, and the supernatant was decanted. The collected precursor block copolymer PCP-18-10 (x=18 and y=10, analyzed by NMR) is a diblock copolymer. The precursor block copolymer was dried in a vacuum oven until a constant weight was reached.

Table 14 summarizes the precursor block copolymers (PCP-x-y) formed by the above-described procedure. PCP-18-0 was formed using only MTCOPrBr for the polycarbonate block. PCP-0-25 was formed using only MTCOEt for the polycarbonate block.

TABLE 14

| PCP-x-y | # Units (x) | # Units (y) | Mn |
|---|---|---|---|
| PCP-14-7 | 14 | 7 | 10250 |
| PCP-18-0 | 18 | 0 | 11120 |
| PCP-18-10 | 18 | 10 | 11938 |
| PCP-18-25 | 18 | 25 | 14758 |
| PCP-0-25 | 0 | 25 | 10820 |

In the second step, shown in Scheme 3, precursor block copolymers PCP-x-y comprising a side chain haloester group (x>0 in Table 14) were quaternized with trimethylamine, thereby forming a cationic nucleophilic block copolymer of formula $N^\alpha$-A'-B'. The nucleophilic group $N^\alpha$, hydrophilic poly(ethylene oxide) block A', and hydrophilic polycarbonate random copolymer block B' are indicated in Scheme 3.

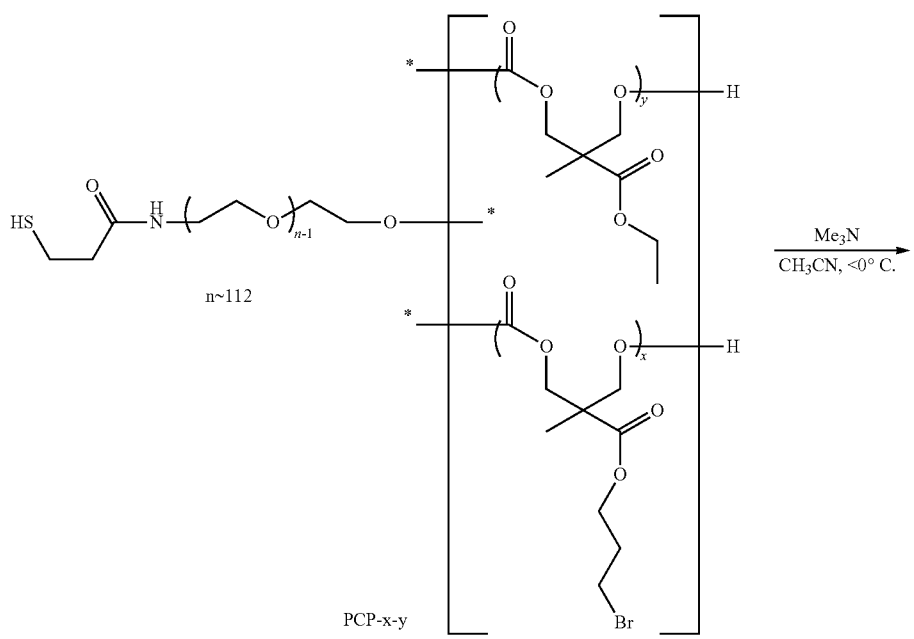

-continued

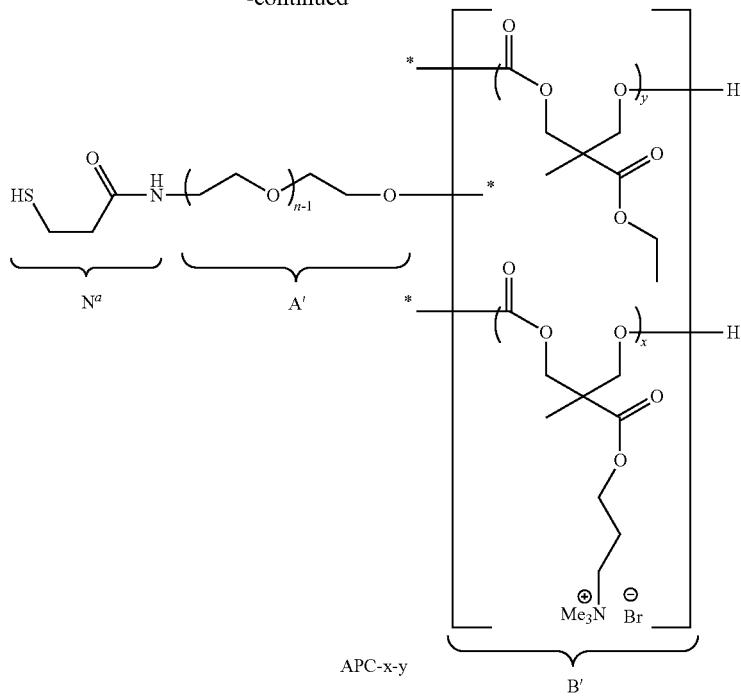

APC-x-y

In the examples that follow, block B' is not endcapped. Block B' has an end unit comprising a nucleophilic hydroxy group capable of initiating a ring opening polymerization to form a third block, if desired. The cationic diblock copolymers are referred to as aminated polycarbonates, represented by the name "APC-x-y". The x and y represent the analyzed number of repeat units derived from MTCOPrBr and MTCOEt, respectively, in the polycarbonate block.

The following procedure for the preparation of APC-18-10 is representative, where x=18 and y=10 in the polycarbonate block. The precursor block copolymer PCP-18-10 (0.70 g, about 0.06 mmol) was dissolved in acetonitrile (50 mL) and the solution was transferred (under nitrogen) into a 100 mL pressure safe Schlenk tube equipped with a stir bar. Under nitrogen the solution was cooled with dry ice, after which trimethylamine (about 0.5 g) was condensed into the Schlenk tube. The Schlenk tube was sealed and the solution was held overnight under stirring. Following the quaternization reaction the solution was cooled to ambient temperature and nitrogen was bubbled through to remove excess trimethylamine. The solvent was removed by rotary evaporation, and the obtained product was dried in a vacuum oven until a constant weight was reached. The presence of thiol group was verified with Ellman's assay.

Table 15 summarizes the cationic block copolymers (APC-x-y) formed and their properties. A CMC value was not obtained for APC-18-0 due to the absence of hydrophobic segment.

TABLE 15

| Ex. | APC-x-y | # Units (x) | # Units (y) | CMC (ppm) | Particle size (nm) | Zeta Potential (mV) | Mn | MIC (microM) S. aureus | MIC (microM) E. coli |
|---|---|---|---|---|---|---|---|---|---|
| 7 | APC-14-7 | 14 | 7 | 105 | 143.4 ± 2.3 | 39.7 ± 2.0 | 12000 | 41.6 | 416.6 |
| 8 | APC-18-0 | 18 | 0 | | | | 11120 | 449.6 | >449.6 |
| 9 | APC-18-10 | 18 | 10 | 70 | 177.5 ± 1.5 | 44.4 ± 0.5 | 13080 | 38.2 | 191.2 |
| 10 | APC-18-25 | 18 | 25 | 30 | 133.4 ± 7.5 | 45.9 ± 0.8 | 15782 | 15.8 | 63.3 |

[a] Mn is the number average molecular weight of the APC-x-y block copolymer.

Each example of Table 15 is a linear cationic diblock copolymer comprising i) a first block comprising a cationic random polycarbonate copolymer chain and ii) a second block comprising a poly(ethylene oxide) chain terminated with a thiol group. Each of the two blocks of the diblock copolymer is hydrophilic; however, the cationic block comprises a hydrophobic repeat unit derived from MTCOEt that acts as a spacer group to the cationic repeat units derived from MTCOPrBr. These spacer groups, as shown further below, can be used to tune the antimicrobial properties of the cationic hydrogels. CMC in Table 15 is the critical micelle concentration in ppm. The micelle particle size and zeta potential are also listed in Table 15. The minimum inhibitory concentration (MIC) of each block copolymer was tested against S. aureus and E. coli as described below. The MIC is expressed in units of micromoles per liter (microM) based on the number average molecular weight (Mn) of the cationic block copolymer. The CMC, particle size and zeta potential were not measured for APC-18-0. APC-18-0 has no hydrophobic repeat unit derived from MTCOEt, and therefore the tendency for this polymer to self-assemble into micelles is low.

Minimal Inhibitory Concentration (MIC) of APC-x-y Polymers and PCP-0-25.

Gram-positive bacteria (e.g., *S. aureus*) and Gram-negative bacteria (e.g., *E. coli*) account for the majority of infections of implanted devices. For example, 70% of catheter-associated infections are caused by *S. aureus*, and 8% by *E. coli*. Therefore, cationic block copolymers APC-x-y were evaluated for their ability to inhibit the growth of *S. aureus* and *E. coli*.

Minimal inhibitory concentrations (MIC) of the cationic block copolymers of Table 15 in aqueous solution were determined against *S. aureus* and *E. coli* using a broth microdilution method. In this method, 100 microliters of polymer solution with various concentrations was placed into each well of 96-well plates. 100 microliters of microorganism solution at a concentration that gave an optical density reading of about 0.1 at 600 nm was added into each well. The cell cultures were then incubated for 8 hours and the optical density was monitored at 2 hour intervals. The minimum inhibitory concentration (MIC) in mg/L of cationic diblock copolymer was taken at the concentration at which no growth was observed. Broth containing cells alone was used as control. A lower MIC value indicates higher antimicrobial activity. As shown in Table 15 above, Example 10 (APC-18-25), which comprises the highest number of cationic repeat units and the highest number of hydrophobic repeat units, had the highest activity (lowest MIC value in micromoles) against *S. aureus* and *E. coli*. Without being bound by theory, increasing the number of cationic repeat units in the cationic block copolymer might enhance the electrostatic interaction between the polymer and the bacterial cell wall/membrane, which potentially translates to more effective antimicrobial activity. An increased content of the hydrophobic repeat units in the cationic diblock copolymer might also promote interactions of the cationic polymer with the lipid regions of the bacterial cell membrane, potentially causing disintegration of the membrane and leading to more efficient lysis of the bacteria.

Although the trend in growth inhibition by the cationic block copolymers against *E. coli* was similar to the trend in the growth inhibition against *S. aureus*, the cationic diblock copolymers were not as efficient in inhibiting growth of *E. coli* compared to *S. aureus*, evidenced by the MIC exceeding 50 microM in each case (Table 15). A MIC less than or equal to 50 microM is preferable.

Non-charged block copolymer PCP-0-25 was not effective in inhibiting the growth of *S. aureus* and *E. coli* up to a concentration of 462.1 microM.

C. Hydrogels.

Covalently crosslinked cationic hydrogels were formed by a single pot sequential reaction sequence shown in Scheme 4.

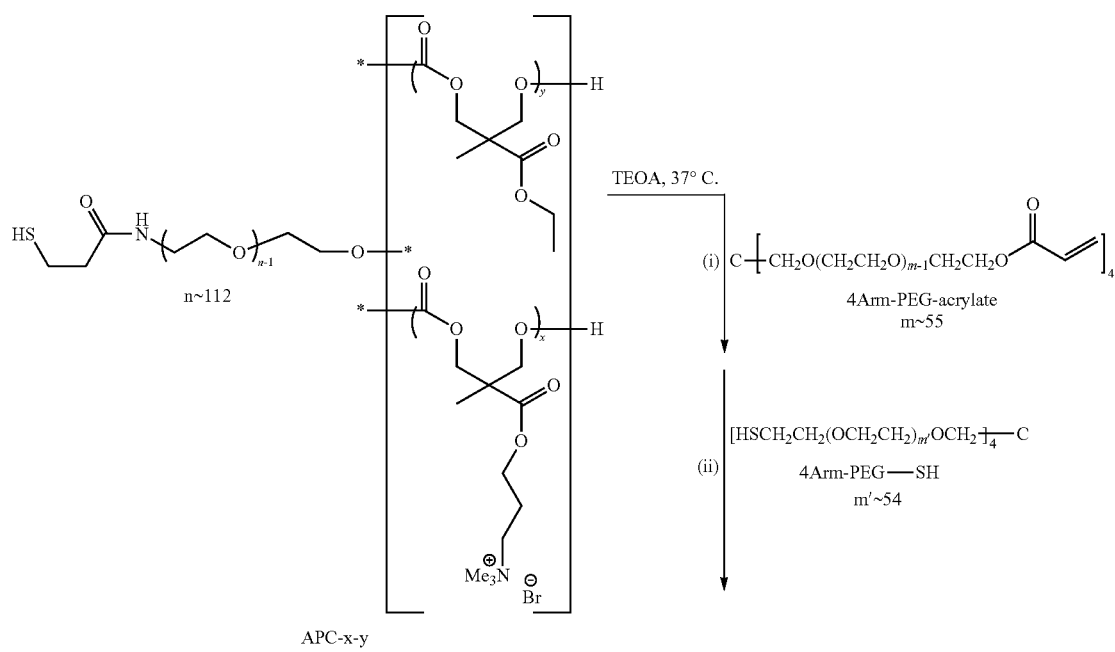

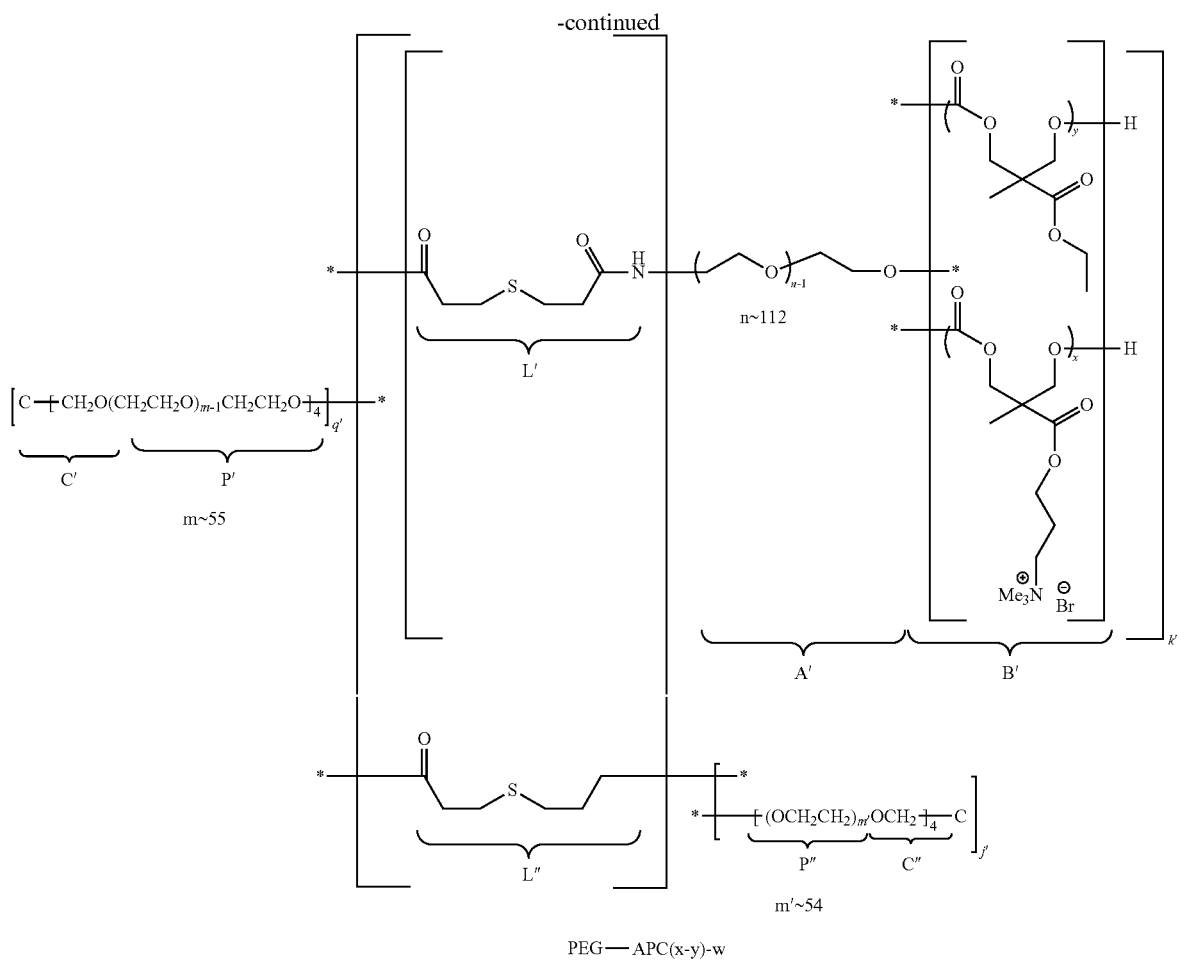

PEG—APC(x-y)-w

In the hydrogel PEG-APC(x-y)-w of Scheme 4, C', C", P', P''', L', L", A', and B' are shown in accordance with formula (1). For clarity, starred bonds indicate attachment sites. L' in Scheme 4 has the structure:

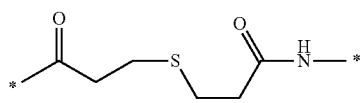

L" in Scheme 4 has the structure:

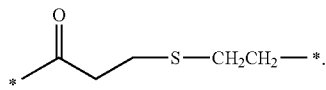

Subscripts j', k', and q' of Scheme 4 represent relative moles of 4Arm-PEG-SH, APC-x-y cationic diblock copolymer, and 4Arm-PEG-acrylate, respectively, used to make the hydrogel. The molar ratio of thiol groups to acrylate groups was 1:1 m/m in the preparation of hydrogel Examples 11 to 25. That is, the relationship $(4j+k)/4q=1$ was maintained for each hydrogel. The name of the cationic hydrogel is represented as PEG-APC(x-y)-w, wherein the APX(x-y) portion of the name indicates the cationic block polymer used to prepare the hydrogel, x is the number of analyzed repeat units derived from MTCOPrBr, y is the number of analyzed repeat units derived from MTCOEt, and w represents the concentration in millimoles per liter (mM) of APC-x-y in the total volume of hydrogel precursor mixture used to prepare the hydrogel. A higher w value indicates a higher content of APC-x-y in the cationic hydrogel.

In the first reaction, 4Arm-PEG-acrylate was treated with thiol-terminated APC-x-y, the acrylate units in molar excess of the thiol units, thereby forming an intermediate thioether adduct by Michael addition of the thiol group to the acrylate double bond. The intermediate thioether adduct comprises unreacted acrylate vinyl groups. The reaction rate of the Michael addition is greatly affected by pH and temperature. In this study, the reaction was conducted at pH 8.0 because deprotonated thiols rather than thiols are the reactive species in the Michael addition reaction with acrylate groups. The reactivity of acrylate groups towards thiol terminated APC-x-y polymers was evaluated by UV-Vis spectroscopy using Ellman's reagent. The results showed that the concentration of thiol groups decreased gradually and they were completely consumed in 2 hours at pH 8.0 and 37° C. A cationic hydrogel was formed by treating the intermediate thioether adduct in situ with a branched tetra-thiol compound, 4Arm-PEG-SH, thereby forming a cationic crosslinked hydrogel network.

Examples 11 to 25

Preparation of covalently crosslinked cationic hydrogels via Michael addition. The following procedure for preparing the cationic hydrogel of Example 19 from APC-18-10 is representative. 4Arm-PEG-acrylate (2.0 mg, 0.20 micromoles) was dissolved in triethanolamine (TEOA) (10 microliters, 0.3M, pH 8.0) and then reacted with APC-18-10 (1.308 mg, 0.1 micromoles, in 30 microliters TEOA). The reaction solution was kept in a 37° C. incubator for 2 hours. 4Arm-PEG-SH (1.75 mg, 0.175 micromoles, in 10 microliters of TEOA) was then added to the solution to give total volume of 50 microliters. The reaction mixture was kept at 37° C., and a hydrogel formed in minutes.

The working molecular weights in grams per mole (g/mol) of the component used to prepare the hydrogels of Examples 11 to 25 are listed in Table 16. The working molecular weight of the 4ARM-PEG-Acrylate and 4ARM-PEG-SH is based on the weight average molecular weight (Mw) of these components. The working molecular weight of the APC-x-y polymers and UBC1 is based on the number average molecular weight (Mn) of these materials.

TABLE 16

| Hydrogel Precursor | (g/mol) |
| --- | --- |
| 4Arm-PEG-Acrylate | 10000 |
| 4Arm-PEG-SH | 10000 |
| APC-14-7 | 12000 |
| APC-18-0 | 11120 |
| APC-18-10 | 13080 |
| APC-18-25 | 15782 |

Table 17 summarizes the amounts in milligrams and micromoles of each precursor used to prepare the hydrogels of Examples 11 to 25, using the working molecular weight of Table 16.

For clarity using Example 13, the name PEG-APC(14-7)-2 denotes the hydrogel synthesized with APC-14-7, which comprises 14 cationic repeat units (x=14) derived from MTCOPrBr and 7 hydrophobic repeat units (y=7) derived from MTCOEt, and w=2. A w=2 value indicates APC-14-7 was present in the hydrogel precursor mixture at a concentration of 2 millimoles per liter (2 mM). Specifically, APC-14-7 (1.2 mg, 0.1 micromoles) was dissolved in a total volume of hydrogel precursor mixture of 50 microliters, resulting in a concentration of APC-14-7 in the hydrogel precursor mixture of 0.1 micromoles/50 microliters=0.002 mol/L=2 mM. The total volume of hydrogel precursor mixture was 50 microliters in each example.

Likewise, APC-14-7 was present at a concentration of 4 mM in the hydrogel precursor mixture used to prepare Example 15, PEG-APC(14-7)-4.

The combined concentration of the precursors (4Arm-PEG-acrylate, APC-x-y, 4Arm-PEG-SH) in the hydrogel precursor mixture was 10% (weight/volume) in each of the Examples 11 to 25.

Table 18 lists the weight percent (wt. %) of each hydrogel precursor used in Examples 11 to 25, based on total combined dry weight of the hydrogel precursors (i.e., APC-x-y, 4Arm-PEG-acrylate, and 4Arm-PEG-SH) in the hydrogel precursor mixture. Table 18 also lists the mole percent (mol %) of each hydrogel precursor used in Examples 11 to 25, based on total moles of the hydrogel precursors present in the hydrogel precursor mixture. The sum of the mole percents of the hydrogel precursors equals 100 percent.

TABLE 17

| Ex. | Cationic Hydrogel | APC-x-y | Hydrogel Precursors (mg) | | | | Hydrogel Precursors (micromoles) | | |
| --- | --- | --- | --- | --- | --- | --- | --- | --- | --- |
| | | | APC-x-y | UBC1 | 4Arm-PEG-acrylate | 4Arm-PEG-SH | APC-x-y | 4Arm-PEG-acrylate | 4Arm-PEG-SH |
| 11 (comp) | PEG-APC-0 | None | 0.000 | 0 | 2.500 | 2.500 | 0.000 | 0.250 | 0.250 |
| 12 | PEG-APC(14-7)-1 | APC-14-7 | 0.600 | 0 | 2.260 | 2.140 | 0.050 | 0.226 | 0.214 |
| 13 | PEG-APC(14-7)-2 | APC-14-7 | 1.200 | 0 | 2.000 | 1.750 | 0.100 | 0.200 | 0.175 |
| 14 | PEG-APC(14-7)-3 | APC-14-7 | 1.800 | 0 | 1.800 | 1.400 | 0.150 | 0.180 | 0.140 |
| 15 | PEG-APC(14-7)-4 | APC-14-7 | 2.400 | 0 | 1.560 | 1.060 | 0.200 | 0.156 | 0.106 |
| 16 | PEG-APC(18-0)-1 | APC-18-0 | 0.556 | 0 | 2.300 | 2.175 | 0.050 | 0.230 | 0.218 |
| 17 | PEG-APC(18-0)-2 | APC-18-0 | 1.112 | 0 | 2.070 | 1.820 | 0.100 | 0.207 | 0.182 |
| 18 | PEG-APC(18-10)-1 | APC-18-10 | 0.650 | 0 | 2.250 | 2.125 | 0.050 | 0.225 | 0.213 |
| 19 | PEG-APC(18-10)-2 | APC-18-10 | 1.300 | 0 | 2.000 | 1.750 | 0.099 | 0.200 | 0.175 |
| 20 | PEG-APC(18-10)-3 | APC-18-10 | 1.960 | 0 | 1.720 | 1.350 | 0.150 | 0.172 | 0.135 |
| 21 | PEG-APC(18-10)-4 | APC-18-10 | 2.600 | 0 | 1.450 | 0.950 | 0.199 | 0.145 | 0.095 |
| 22 | PEG-APC(18-25)-1 | APC-18-25 | 0.780 | 0 | 2.170 | 2.050 | 0.049 | 0.217 | 0.205 |
| 23 | PEG-APC(18-25)-2 | APC-18-25 | 1.570 | 0 | 1.830 | 1.580 | 0.099 | 0.183 | 0.158 |
| 24 | PEG-APC(18-25)-3 | APC-18-25 | 2.370 | 0 | 1.500 | 1.130 | 0.150 | 0.150 | 0.113 |
| 25 | PEG-APC(18-25)-4 | APC-18-25 | 3.100 | 0 | 1.200 | 0.700 | 0.196 | 0.120 | 0.070 |

TABLE 18

| Ex. | Cationic Hydrogel | APC-x-y | Hydrogel Precursors (wt. %) | | | Hydrogel Precursors (mol %) | | | Crosslink Density (%)[a] |
|---|---|---|---|---|---|---|---|---|---|
| | | | APC-x-y | 4Arm-PEG-acrylate | 4Arm-PEG-SH | APC-x-y | 4Arm-PEG-acrylate | 4Arm-PEG-SH | |
| 11 (comp) | PEG-APC-0 | None | 0.0 | 50.0 | 50.0 | 0.0 | 50.0 | 50.0 | 100.0 |
| 12 | PEG-APC(14-7)-1 | APC-14-7 | 12.0 | 45.2 | 42.8 | 10.2 | 46.2 | 43.6 | 94.4 |
| 13 | PEG-APC(14-7)-2 | APC-14-7 | 24.2 | 40.4 | 35.4 | 21.1 | 42.1 | 36.8 | 87.4 |
| 14 | PEG-APC(14-7)-3 | APC-14-7 | 35.8 | 35.8 | 28.4 | 31.7 | 38.1 | 30.2 | 79.3 |
| 15 | PEG-APC(14-7)-4 | APC-14-7 | 47.8 | 31.1 | 21.1 | 43.3 | 33.8 | 22.9 | 67.8 |
| 16 | PEG-APC(18-0)-1 | APC-18-0 | 11.1 | 45.7 | 43.2 | 10.1 | 46.2 | 43.7 | 94.6 |
| 17 | PEG-APC(18-0)-2 | APC-18-0 | 22.2 | 41.4 | 36.4 | 20.5 | 42.3 | 37.2 | 87.9 |
| 18 | PEG-APC(18-10)-1 | APC-18-10 | 13.0 | 44.7 | 42.3 | 10.3 | 46.1 | 43.6 | 94.6 |
| 19 | PEG-APC(18-10)-2 | APC-18-10 | 25.7 | 39.6 | 34.7 | 21.1 | 42.1 | 36.8 | 87.4 |
| 20 | PEG-APC(18-10)-3 | APC-18-10 | 39.0 | 34.2 | 26.8 | 32.9 | 37.7 | 29.4 | 78.0 |
| 21 | PEG-APC(18-10)-4 | APC-18-10 | 52.0 | 29.0 | 19.0 | 45.5 | 33.0 | 21.6 | 65.5 |
| 22 | PEG-APC(18-25)-1 | APC-18-25 | 15.8 | 43.4 | 40.7 | 10.6 | 46.0 | 43.4 | 94.3 |
| 23 | PEG-APC(18-25)-2 | APC-18-25 | 31.5 | 36.7 | 31.7 | 22.7 | 41.5 | 35.8 | 86.3 |
| 24 | PEG-APC(18-25)-3 | APC-18-25 | 47.4 | 30.0 | 22.5 | 36.3 | 36.3 | 27.4 | 75.5 |
| 25 | PEG-APC(18-25)-4 | APC-18-25 | 62.0 | 24.0 | 14.0 | 51.3 | 30.8 | 17.9 | 58.1 |

[a] Estimated percentage of chains P' covalently linked to chains P''' based on molar ratio of 4Arm-PEG-SH to 4Arm-PEG-acrylate used to prepare the hydrogel.

Summarizing the weight percents of the hydrogel precursors used in Examples 12 to 25 that contain a cationic block copolymer, APC-x-y was present in the hydrogel precursor mixture in an amount of 11.1 wt. % to 62.0 wt. %, 4Arm-PEG-acrylate was present in the hydrogel precursor mixture in an amount of 24.0 wt. % to 45.7 wt. %, and 4Arm-PEG-SH was present in the hydrogel precursor mixture in an amount of 14.0 wt. % to 43.2 wt. % based on total dry weight of the hydrogel precursors.

Summarizing the mole percents of the hydrogel precursors used in Examples Examples 12 to 25, the APC-x-y was present in the hydrogel precursor mixture in an amount of 10.1 mol % to 51.3 mol %, 4Arm-PEG-acrylate was present in the hydrogel precursor mixture in an amount of 30.8 mol % to 46.2 mol %, and 4Arm-PEG-SH was present in the hydrogel precursor mixture in an amount of 17.9 mol % to 43.7 mol %, based on total moles of the hydrogel precursors, where the sum of the mol % of the three components equaled 100%.

The efficiency of the reaction of the 4Arm-PEG-acrylate with APC-x-y block copolymers was determined by monitoring the consumption of thiol groups by UV-VIS absorbance using Ellman's reagent. For example, 16 mg of 4Arm-PEG-acrylate was dissolved in 50 microliters of TEOA, and 9.6 mg of APC-18-10 was dissolved in 200 microliters of TEOA was then added. At predetermined time intervals, aliquots (50 microliters) of the reaction mixture were withdrawn for Ellman's analysis. The absorbance of the mixture at 412 nm was measured using a UV-VIS spectrometer (Shimadzu, UV-2501PC, Japan). The percent thiol was estimated using thiolamide-PEG-OH (Mn 5000 Da) as standard. The results showed that the concentration of thiol decreased gradually and was completely consumed in 2 hours at pH 8.0 and 37° C., indicating the complete reaction between vinyl acrylate and thiol groups.

In Examples 11 to 25, the percentage of chains P' of the 4Arm-PEG-acrylate that are covalently linked to chains P''' of the 4Arm-PEG-thiol is in the range of 58.1% to 94.6% (Example 25 and Example 15, respectively) based on molar ratios of 4Arm-PEG-thiol to 4Arm-PEG-acrylate.

Physical Characterization of Hydrogels.

Table 19 summarizes the physical properties of hydrogels of Examples 11 (non-charged, comparative) and Examples 14 to 25 (cationic). PEG-APC-0 of example 11 was formed without using any APC-x-y polymer in the hydrogel precursor mixture.

TABLE 19

| Example | Cationic Hydrogel | APC-x-y | Gel Time (min) | Swell Ratio | Ww[a] (mg) | Wd[b] (mg) | Gel yield[c] (%) | Ge[d] (Pa) |
|---|---|---|---|---|---|---|---|---|
| 11 (comp) | PEG-APC-0 | None | 2 | 19.9 | 94.1 | 4.5 | 90 | 4056.0 |
| 12 | PEG-APC(14-7)-1 | APC-14-7 | | | | | | |
| 13 | PEG-APC(14-7)-2 | APC-14-7 | 6 | 21.9 | 96.2 | 4.2 | 84 | 3137.2 |
| 14 | PEG-APC(14-7)-3 | APC-14-7 | | | | | | |
| 15 | PEG-APC(14-7)-4 | APC-14-7 | 10 | 33.9 | 111.6 | 3.2 | 64 | 788.5 |
| 16 | PEG-APC(18-0)-1 | APC-18-0 | | | | | | |
| 17 | PEG-APC(18-0)-2 | APC-18-0 | 4 | 21.4 | 91.5 | 4.1 | 82 | |
| 18 | PEG-APC(18-10)-1 | APC-18-10 | | | | | | |
| 19 | PEG-APC(18-10)-2 | APC-18-10 | 8 | 22.2 | 95.1 | 4.1 | 82 | 2642.7 |
| 20 | PEG-APC(18-10)-3 | APC-18-10 | | | | | | |
| 21 | PEG-APC(18-10)-4 | APC-18-10 | 13 | 36.0 | 114.7 | 3.1 | 62 | 583.1 |
| 22 | PEG-APC(18-25)-1 | APC-18-25 | 6 | 16.8 | 74.7 | 4.2 | 84 | |
| 23 | PEG-APC(18-25)-2 | APC-18-25 | 10 | 23.9 | 97.1 | 3.9 | 78 | 2175.0 |

TABLE 19-continued

| Example | Cationic Hydrogel | APC-x-y | Gel Time (min) | Swell Ratio | Ww$^a$ (mg) | Wd$^b$ (mg) | Gel yield$^c$ (%) | Ge$^d$ (Pa) |
|---|---|---|---|---|---|---|---|---|
| 24 | PEG-APC(18-25)-3 | APC-18-25 | 14 | 29.5 | 94.5 | 3.1 | 62 | |
| 25 | PEG-APC(18-25)-4 | APC-18-25 | 15 | 36.5 | 116.2 | 3.1 | 62 | 509.3 |

$^a$Ww: weight of the swollen gel.
$^b$Wd: weight of the dried gel.
$^c$Gel yield: calculated as the weight ratio between Wd and the combined precursor weight converted to percent.
$^d$Ge: defined as the value of the dynamic storage modulus G' at a frequency of 1 Hz.

Gelation times are listed in Table 19. The gelation time was determined qualitatively by a vial tilting method. When the sample showed no ability to flow, it was regarded as a gel. The time to gel was measured from the addition of 4Arm-PEG-SH.

Gelation occurred within 2 minutes for the non-charged hydrogel PEG-APC-0 prepared without APC-x-y cationic block copolymer (Example 11, comparative).

Increasing the APC-x-y concentration in the cationic hydrogel resulted in longer gelation times. For example, hydrogels formed in 6 minutes and 10 minutes when 2.0 and 4.0 mM APC-14-7, respectively, were used to prepare the cationic hydrogel (Examples 13 and 15, respectively).

The gels were subsequently incubated in deionized (DI) water and allowed to swell, and weighed at various time intervals until a constant weight was observed. Swelling degree was calculated from the formula: Swell Ratio=($W_w$−Wd)/Wd, where $W_w$ represents the weight of swollen gels, and Wd represents the weight of the freeze-dried gels. Gel Yield was calculated as the weight ratio between Wd and the combined precursor weight, converted to percent. All samples were analyzed in triplicate.

Rheology experiments were performed at room temperature using a control-strain rheometer (ARES G2, TA instruments). The rheometer was equipped with two sensitive force transducers for torque ranging from 0.05 microNewton·meter to 200 milliNewton·meter. The swollen gel was placed onto a parallel-plate geometry (8 mm in diameter). The dynamic storage modulus (G') and loss modulus (G") of the gel were examined as a function of frequency from 1 to 100 rad/sec. The measurements were carried out at a strain amplitude (y) of 5% to ensure the linearity of viscoelasticity. The value Ge, defined as G' value at frequency of 1 Hz, is listed in Table 19 for each cationic hydrogels. A lower Ge value indicates a weaker gel. The storage moduli (G') of the hydrogels were significantly decreased by increasing the concentration of the cationic polycarbonate copolymer. For example, the values of G' were 4056.0, 2175.0 and 509.3 Pa, respectively, when 0, 2 and 4 mM of APC-18-25 was used to make the hydrogel (Examples 11, 23 and 25, respectively).

In Vitro Antibacterial Assays of the Cationic Hydrogels.

The cationic hydrogels were evaluated for their ability to inhibit the growth of S. aureus and E. coli. Hydrogels for antibacterial assays were prepared using the procedure described above in 96-well tissue culture plates TCTP (NUNC, treated polystyrene). 50 microliters of hydrogel precursor mixture was transferred to the wells. Gelation occurred in minutes at 37° C. The bacteria were grown in tryptic soy broth (TSB) from Becton, Dickinson and Company (BD) overnight in an incubator at 37° C. The optical density of the bacterial solution was adjusted to OD=0.1 at 600 nm by the addition of TSB. This yielded a bacterial stock solution with $10^8$ colony forming units (CFU)/mL. The stock solution was sequentially diluted to obtain bacterial solutions with various concentrations (i.e., $2\times10^5$, $2\times10^6$, $2\times10^7$, $2\times10^8$ and $2\times10^9$ CFU/dm$^2$). The growth of bacteria was measured using a broth dilution method. In this method, 50 microliters of TSB were introduced onto the surface of the hydrogels, followed by the addition of 50 microliters of the bacterial solution. Four controls were used: i) TSB, ii) phosphate buffered saline (PBS), iii) triethanolamine (TEOA), and iv) PEG-APC-0 (i.e., hydrogel made without cationic block copolymer). Samples were incubated at 37° C. 50 microliters of TSB was added to each well after 12 hours of incubation. The optical density readings of bacterial solutions were monitored by measuring the optical density (OD) at 600 nm. The assay was performed in four replicates for each sample and the experiments were repeated at least three times.

The hydrogels were also tested for antimicrobial activity against 50 microliters of solution having an initial concentration of $10^8$ CFU/mL (colony forming units per milliliter) of the fungi Candida albicans (C. albicans). The C. albicans was incubated at room temperature for 24 hours.

The killing efficiency of the cationic hydrogels was also investigated through the spread agar plate method. After a predetermined incubation time of the hydrogels with the microbial solution (e.g. 8 hours for E. coli and S. aureus, 24 hours for C. albicans), a series of tenfold dilutions were prepared, and plated in Luria-Bertani agar. The plates with E. coli and S. aureus were incubated for 18 hours to 24 hours at 37° C., whereas plates with C. albicans were incubated 48 hours at room temperature. The colonies of the microbes were counted. PEG-APC-0 was used as a control, and its killing efficiency was defined at 0%. The killing efficiency of other gels was calculated relative to that of PEG-APC-0 gel. The killing efficiency, expressed as a percent, was calculated as follows: killing %=100%×[CFU on the PEG-APC-0 gel−CFU on the sample gel]/[CFU on the PEG-APC-0 gel], where CFU is colony forming units.

Long term biofilm formation assay. To evaluate the antimicrobial activities of hydrogels over a long period of time, the growth of S. aureus on the cationic hydrogels and PEG-APC-0 were monitored for 12 days. 50 microliters of the S. aureus solution with an initial concentration of $5.7\times10^6$ CFU/mL was applied to the hydrogels daily. After 24 hours of incubation, killing efficiency was assessed by the spreading agar plate method, where the PEG-APC-0 hydrogel was used as control.

Unlike the APC-x-y cationic diblock copolymers in solution, the cationic hydrogels inhibited the growth of S. aureus. FIG. 1A is a bar chart showing the growth inhibition effect of cationic hydrogel PEG-APC(14-7)-2 compared to the four controls against S. aureus when the initial concentration of S. aureus was $2\times10^9$ CFU/dm$^2$). The S. aureus was completely inhibited by the cationic hydrogel PEG-APC(14-7)-2, whereas S. aureus continued to grow in contact with the non-charged hydrogel PEG-APC-0 (formed with no APC-x-y polymer in the hydrogel precursor mixture). This finding suggests that the cationic polycarbonate chain plays an important role in the antimicrobial activity of the cationic hydrogel. S. aureus also displayed high growth in TEOA, in PBS, and in tryptic soy broth (TSB). These results further indicate the growth inhibition of the S. aureus was influenced by the cationic polycarbonate chain instead of the TEOA.

The cationic hydrogels also showed strong killing efficiency against S. aureus. For example, the killing efficiency of PEG-APC(14-7)-2 and PEG-(APC(14-7)-3 hydrogels against S. aureus was greater than 99.999% after 8 hour incubation (FIG. 1B, bar chart). Similarly, the killing efficiency of cationic hydrogels PEG-APC(18-25)-1, PEG-APC (18-25)-2, PEG-APC(18-25)-3, and PEG-APC(18-25)-4 against S. aureus was also greater than 99.999% after 8 hour incubation (FIG. 1C, bar chart). Cationic urea-containing hydrogel CUH1, also shown in FIG. 1C, is described further below. CUH1 had comparable killing efficiency to PEG-APC (18-25)-1 to PEG-APC(18-25)-4.

The cationic hydrogels were also active against E. coli. As shown in the bar chart of FIG. 2A, PEG-APC(18-25)-2 and PEG-APC(18-25)-4 effectively inhibited growth of E. coli during 8 hours of incubation using an initial E. coli concentration of $2 \times 10^9$ CFU/dm$^2$).

The initial bacterial loading density was also varied to simulate the clinical contamination level of microbes, which ranges from surgical theater operation (less than 100 CFU/dm$^2$) to massive contamination. The growth inhibition effect on E. coli by cationic hydrogels PEG-APC(18-25)-2 and PEG-APC(18-25)-4 when the E. coli was introduced at concentrations of $2 \times 10^5$ CFU/dm$^2$ to $2 \times 10^9$ CFU/dm$^2$ was followed for 8 hours (FIG. 2B) and 24 hours (FIG. 2C) of incubation. The scatter plots of FIGS. 2B and 2C demonstrate that a tissue culture plate (TCTP) control (Nunc MicroWell™ Plates, Catalog No. 167008) and PEG-APC-0 hydrogel control were ineffective in inhibiting growth of E. coli even when the initial concentration of E. coli was $2 \times 10^5$ CFU/dm$^2$ (FIG. 2C). By comparison, cationic hydrogel PEG-APC(18-25)-2 inhibited the growth of E. coli effectively for 24 hours (at least) when the initial concentration of E. coli was $2 \times 10^8$ CFU/dm$^2$ (FIG. 2C). Most promisingly, cationic hydrogel PEG-APC(18-25)-4 inhibited the growth of E. coli effectively for 24 hours (at least) when the initial concentration of E. coli was $2 \times 10^9$ CFU/dm$^2$ (FIG. 2C), showing that growth inhibition efficiency could be increased by increasing the APC-18-25 content in the hydrogel.

Cationic hydrogels formed with APC-18-25 also had greater effectiveness in killing E. coli compared to hydrogels formed with APC-14-7 and APC-18-10 (FIG. 2D, bar chart). In addition, PEG-APC(18-25)-3 killed E. coli as efficiently as PEG-APC(18-25)-2 (FIG. 2E, bar chart).

The relative antimicrobial activity of the cationic hydrogels formed with each of the APC-x-y polymers follows the trend of antimicrobial activity observed with the APC-x-y polymers in solution (see MIC data above).

In addition to bacteria, antifungal activity of hydrogels in inhibiting the growth of C. albicans was evaluated. FIG. 3A (bar chart) shows that hydrogel PEG-APC(18-25)-2 possesses excellent inhibitory activity against C. albicans. Particularly, PEG-APC(18-25)-2 demonstrates approximately 100% killing efficiency against C. albicans (FIG. 3B, bar chart), whereas PEG-APC(18-0)-2, containing no hydrophobic repeat unit in the polycarbonate block, was slightly less efficient. The presence of the hydrophobic repeat unit in the APC-18-25 cationic block copolymers appears to increase killing efficiency against the fungus C. albicans.

Importantly, there is no S. aureus biofilm formation observed on the hydrogels PEG-APC(18-25)-2 and PEG-APC(18-25)-3 over a 12 day period. However, S. aureus grew rapidly on the control hydrogel PEG-APC-0 (FIG. 4, bar chart).

Hemolysis Assays.

Fresh rat blood cells were washed with PBS three times. A red blood cell suspension in PBS (4% in volume, 100 microliters) was placed on the surface of hydrogel in each well of 96-well plates and PBS (100 microliters) was then added to the well. PBS, PEG-APC-0, and TRITON X-100 (0.2%) (a trademark of Rohm & Haas Company, Philadelphia, Pa.) were used as controls. The plates were incubated for one hour at 37° C. The 96 well plates were centrifuged at 4000 rpm for 5 minutes. Aliquots (100 microliters) of the supernatant were transferred to a clean 96 well plate. Hemoglobin release was measured at 576 nm using a microplate reader (TECAN). The red blood cells in PBS were used as a negative control. Absorbance of wells with red cells lysed with 0.2% TRITON X-100 was taken as 100% hemolysis. Percentage of hemolysis was calculated using the following formula: Hemolysis (%)= [(Sample OD$_{576nm}$−PBS OD$_{576nm}$)/(0.2% TRITON X-100 OD$_{576nm}$−PBS OD$_{576nm}$)×100, where OD$_{576nm}$ is the absorbance at 576 nm. The data were expressed as mean and standard deviation of four replicates and the tests were repeated 3 times.

As shown in FIG. 5, cationic hydrogels exhibit fairly low hemolytic activity especially at APC-x-y concentrations of 1 and 2 mM.

Scanning Electron Microscopy (SEM).

To gain insights into the antimicrobial activity of the cationic hydrogels, morphological changes of S. aureus and E. coli before and after the contact with the hydrogels were investigated.

The bacteria grown in broth alone and on the surface of hydrogels were collected by centrifugation at 4000 rpm for 5 min. The cells were washed by PBS three times and then fixed in formalin solution containing 4% formaldehyde for two days. The cells were further washed with DI water, followed by dehydration using a series of ethanol solutions with different volume contents (3-5%, 50%, 75%, 90%, 95% and 100%). The bacterial sample was placed on a carbon tape, which was further coated with platinum. The morphologies of the bacteria before and after treatment were observed using a field emission scanning electron microscope (SEM) (JEOL JSM-7400F) operated at an accelerating voltage of 10.0 kv and working distance of 8.0 mm.

Untreated Gram-positive S. aureus has round and smooth morphology when the cell wall is intact. As can be seen in the SEM images of FIGS. 6E to 6J, the bacterial cells remain round and intact when cultured in TEOA (FIGS. 6E and 6F), TSB (FIGS. 6G and 6H), and PBS (FIGS. 6I and 6J). Cells cultured on the surface of PEG-APC-0 hydrogel also remained healthy (FIGS. 6C and 6D). In contrast, aggregations of lipid vesicles and rough surfaces were observed for S. aureus in contact with PEG-APC (14-7)-2 hydrogel for 2 hours (FIGS. 6A and 6B).

Untreated Gram-negative E. coli cells have a rod-shaped structure and smooth surface. E. coli cells cultured in a TCTP control (Nunc MicroWell™ Plates, Catalog No. 167008) for 2 hours at 37° C. show no ruptures and no large pores (FIGS. 7G and 7H). E. coli cells cultured in contact with hydrogel PEG-APC-0 for 2 hours at 37° C. also showed no ruptures and no large pores (FIGS. 7E and 7F). *E. coli* cells cultured in contact with the cationic hydrogel PEG-APC(18-25)-2 for 2 hours at 37° C. retained their rod-like form (FIG. 7A). However, numerous vesicle-like structures were observed in the cells (FIG. 7B). In addition, debris was also observed around the disintegrated cells (FIG. 7A). The morphology of *E. coli* cultured in contact with the cationic hydrogel PEG-APC(18-25)-4 revealed a comparable number of vesicle-like structures in the cells (FIG. 7D). However, more debris was also seen (FIG. 7C).

D. Cationic Urea-Containing Hydrogel.

Preparation of Phenylureaethanol (PUE).

ture and then left under stirring for an additional 16 hours. THF was removed through rotational evaporation the following morning. The crude product was recrystallized from ethyl acetate and then stirred rigorously for an additional 4 hours. The solids thus formed were removed by filtration, washed with further ethyl acetate and dried until a constant weight was reached, yield 7.0 g (~86%). $^1$H-NMR (DMSO-d6) delta: 8.59 (s, 1H, NH), 7.39 (d, 2H, ArH), 7.21 (t, 2H, ArH), 6.95 (t, 1H, ArH), 6.10 (t, 1H, NH), 4.78 (t, 1H, OH), 3.43 (q, 2H, $CH_2$), 3.17 (q, 2H, $CH_2$).

Preparation of MTCU.

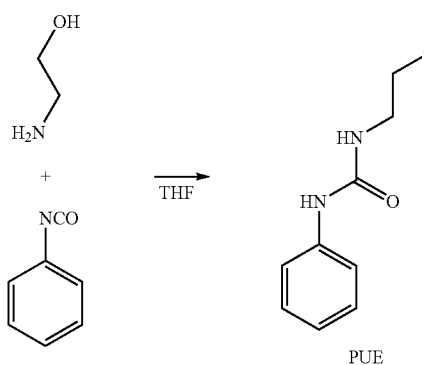

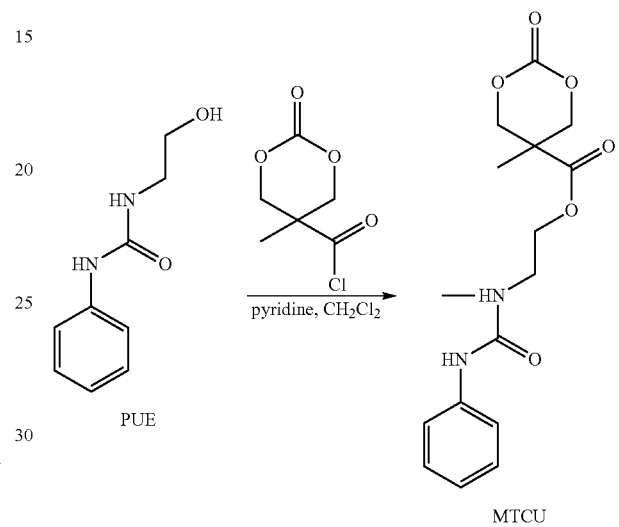

In a dry 100 mL round bottom flask equipped with a stir bar was charged ethanolamine (2.96 g, 48.5 mmol, 1 eq). Dry THF (30 mL) was added and the resulting solution cooled to 0° C. using an ice bath. A dropping funnel was attached in which phenylisocyanate (5.19 g, 4.74 mL, 43.6 mmol, 0.9 eq) and 30 mL of dry THF was charged. The resulting solution was added drop wise during a period of 30 minutes. The resulting solution was allowed to warm to ambient tempera- Preparation of hydrogel precursor UBC1. Using the above-described ROP polymerization procedure, a non-charged diblock copolymer UBC1 having a pendant urea group was prepared according to Scheme 5.

Scheme 5.

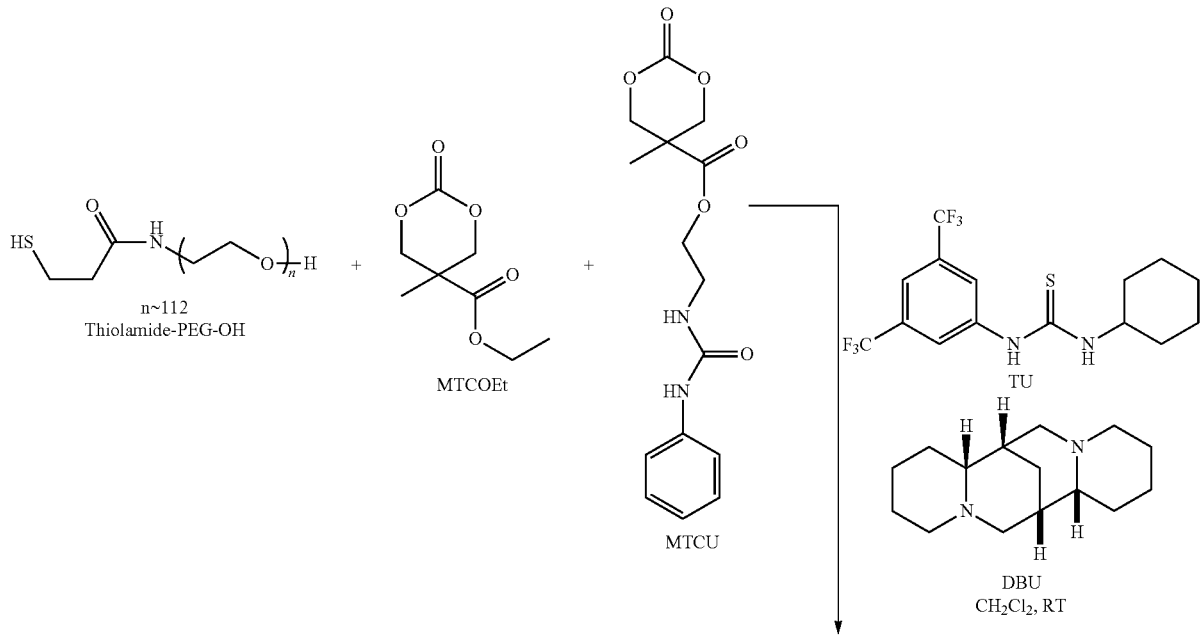

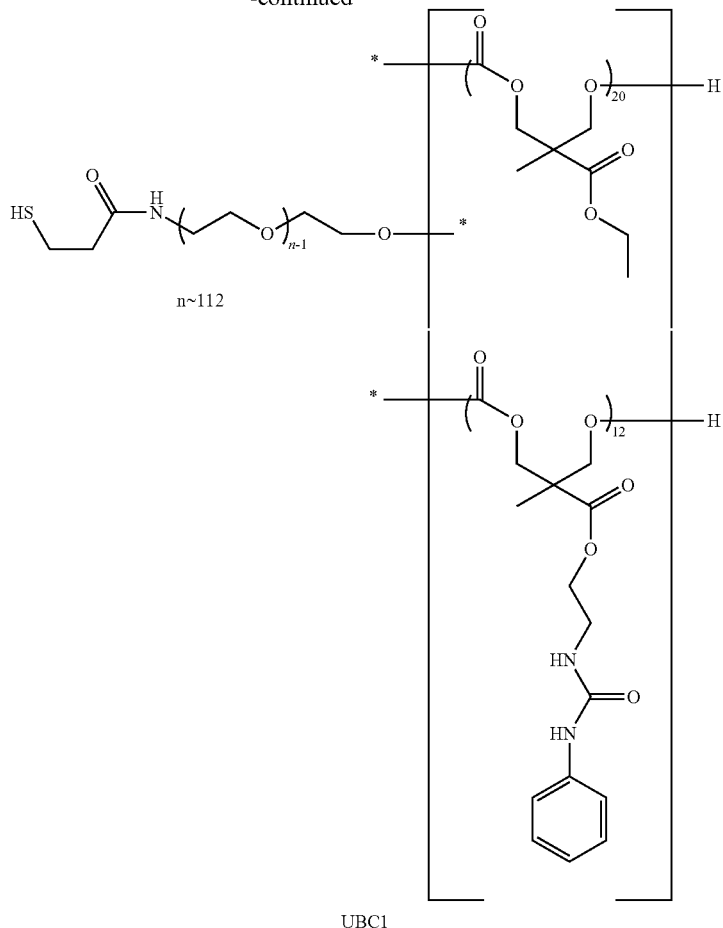

UBC1

Thus, a vial with stirbar was charged with thiolamide-PEG-OH (0.15 g, 0.030 mmol, Mn 5000), MTCOEt (0.056 g, 0.30 mmol), MTCU (0.040 g, 0.12 mmol), and TU (0.035 g, 0.094 mmol). Dichloromethane (DCM) (0.75 g) was then added and the reaction mixture was stirred until complete dissolution was observed. The polymerization was then initiated by the addition of (−)-sparteine (0.015 g, 0.063 mmol). Upon complete monomer conversion the reaction mixture was precipitated into cold diethyl ether yielding 0.21 g (85 white amorphous polymer UBC1. This hydrogel precursor material was used to investigate the effect of strong hydrogen bonding groups on the mechanical properties of the resultant hydrogel. The NMR analyzed number of subunits derived from MTCU and MTCOEt in UBC1 was 12 and 20, respectively. Mn=25700.

Example 26

Preparation of cationic urea-containing hydrogel CUH1. Following the above-described procedures, a cationic hydrogel was prepared using cationic block copolymer APC-18-25, non-charged urea-containing block copolymer UBC1, 4Arm-PEG-acrylate, and 4Arm-PEG-SH according to Scheme 6. 4Arm-PEG-acrylate was first incubated with APC-18-25 and UBC1 at 37° C. for 2 hours. Gelation occurred with the addition of 4Arm-PEG-SH.

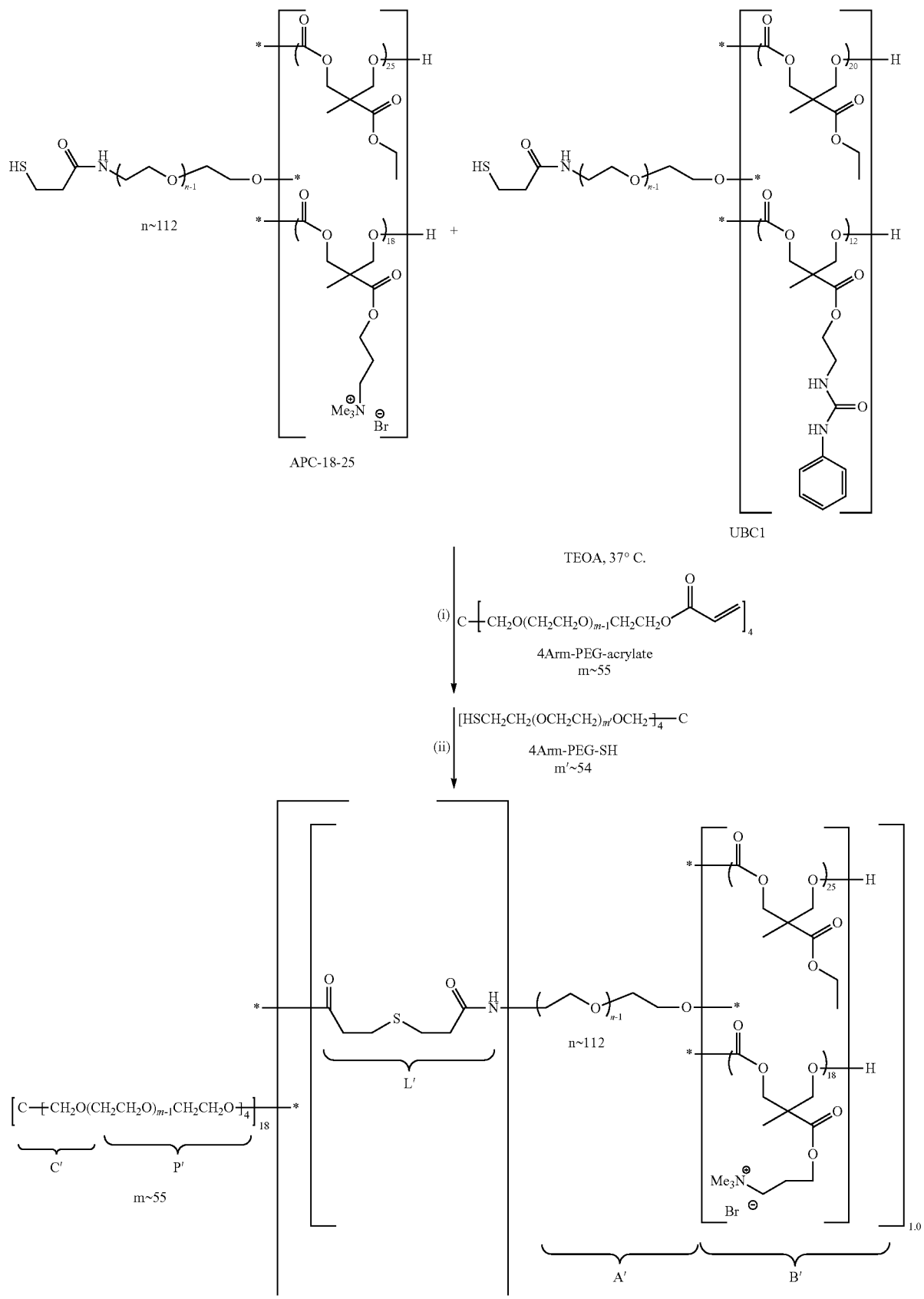

-continued

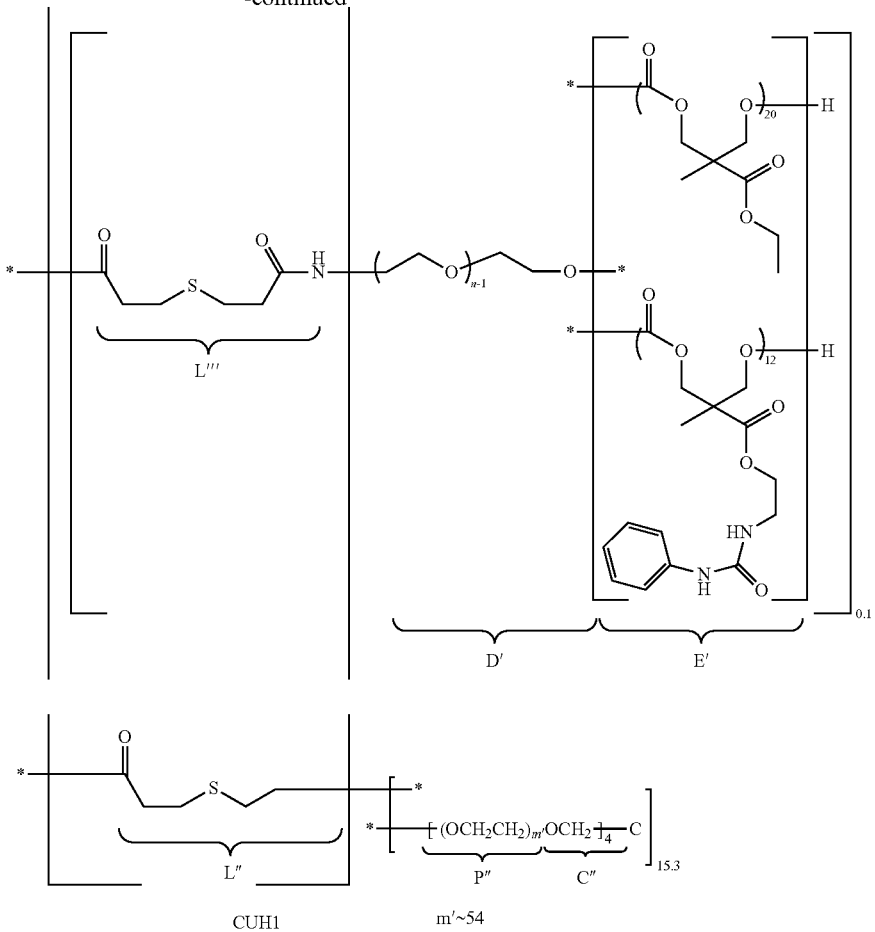

CUH1  m'~54

In the hydrogel CUH1 of Scheme 6, C', C'', P', P'', L', L'', L''', A', B', D', and E' are shown in accordance with formula (1). The amounts of each precursor used in the preparation of cationic hydrogel CUH1 in milligrams (mg) and micromoles (based on Mn or Mw) are listed in Table 20.

TABLE 20

| Ex. | Cationic Urea Hydrogel | Hydrogel Precursors (mg) | | | | Hydrogel Precursors (micromoles) | | | |
|---|---|---|---|---|---|---|---|---|---|
| | | APC-18-25 | UBC1 | 4Arm-PEG-acrylate | 4Arm-PEG-SH | APC-18-25 | UBC1 | 4Arm-PEG-acrylate | 4Arm-PEG-SH |
| 26 | CUH1 | 1.57 | 0.137 | 1.8 | 1.52 | 0.1 | 0.01 | 0.18 | 0.153 |

The combined concentration of APC-18-25 and UBC1 in the hydrogel precursor mixture was 2 millimoles per liter (2 mM). The molar ratio of APC-18-25 to UBC1 was 0.1 to 0.01 (10:1 m/m).

The amounts of hydrogel precursors in wt. % and mol % used in the preparation of cationic hydrogel CUH1 are listed in Table 21.

TABLE 21

| Ex. | Cationic Urea Hydrogel | APC-x-y | Hydrogel Precursors (wt. %) | | | | Hydrogel Precursors (mol %) | | | | Crosslink Density (%)[a] |
| --- | --- | --- | --- | --- | --- | --- | --- | --- | --- | --- | --- |
| | | | APC-18-25 | UBC1 | 4Arm-PEG-acrylate | 4Arm-PEG-SH | APC-18-25 | UBC1 | 4Arm-PEG-acrylate | 4Arm-PEG-SH | |
| 26 | CUH1 | APC-18-25 | 31.3 | 2.7 | 35.7 | 30.3 | 22.6 | 2.2 | 40.7 | 34.5 | 84.8 |

[a]Estimated percentage of chains P' covalently linked to chains P'' based on molar ratio of 4Arm-PEG-SH to 4Arm-PEG-acrylate used to prepare the hydrogel.

Cationic urea hydrogel CUH1 showed comparable killing efficiency against S. aureus compared to PEG-APC(18:25)-2, PEG-APC(18:25)-3, and PEG-APC(18:25)-4 (FIG. 1C, bar chart), indicating the incorporation of CUH1 does not adversely affect the antimicrobial activity of the resulting hydrogel. The CUH1 gel time was 12 minutes and the CUH1 dynamic storage modulus G' at 1 Hz (Ge in Table 19) was 3398.7 Pa. The closest cationic hydrogel to CUH1 formed without any UBC1 is PEG-APC(18:25)-2 (Example 23, Ge=2175.0 Pa, Table 19). Comparing the Ge values of PEG-APC(18:25)-2 and CUH1, it can be seen that 2.2 mol % UBC1 increases the dynamic storage modulus of the resulting cationic hydrogel by 156%. Thus, non-charge block copolymer UBC1 provides an additional tool for modulating cationic hydrogel properties while retaining potent antimicrobial activity.

Also contemplated is the formation of block B' of nucleophilic cationic block copolymer $N^\alpha$-A'-B' by using MTCU or another urea functionalized cyclic carbonyl monomer as a comonomer in the ring opening polymerization. In this instance, block B' would comprise a first repeat unit comprising a pendant quaternary amine, and a second repeat unit comprising a pendant urea group.

In the above Example 26, the estimated crosslink density (percentage of chains P' of the 4Arm-PEG-acrylate that are covalently linked to chains P'' of the 4Arm-PEG-SH) is 84.8%, based on molar ratio of 4Arm-PEG-SH to 4Arm-PEG-acrylate.

Example 27

Drug-Loaded Hydrogel and In Vitro Drug Release

This example demonstrates encapsulation of a drug by non-covalent interactions within a crosslinked hydrogel and controlled release of the drug from the hydrogel. Diclofenac sodium salt (DCF), which is used to treat pain, inflammatory disorders, and dysmenorrhea, was incorporated into PEG-APC(18:25)-2 hydrogel by mixing with the hydrogel precursors. Diclofenac sodium salt has the structure:

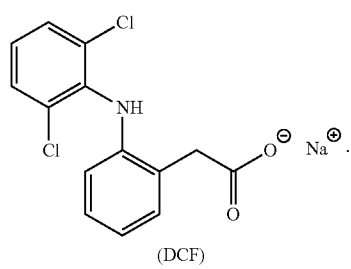

(DCF)

Multiple identical samples of DCF-loaded hydrogel were prepared as follows. 4Arm-PEG-acrylate (1.83 mg, 0.183 micromoles) was dissolved in triethanolamine buffer (TEOA) (9 microliters, 0.3M, pH 8.0) and then reacted with APC-18-25 (1.57 mg, 0.1 micromole) in triethanolamine buffer (TEOA) (25 microliters, 0.3M, pH 8.0). The reaction solution was incubated at 37° C. for 2 hours. 4Arm-PEG-SH (1.75 mg, 0.175 micromoles in 9 microliters TEOA) and DCF (5000 mg/L in phosphate buffered saline (PBS), pH 7.4, 7.5 microliters) were then added to the solution. The molar ratio of thiol groups to vinyl groups was 1.0, and the final precursor concentration was 10% w/v based on total weight of the hydrogel precursors. The reaction mixture was maintained at 37° C., and hydrogel formed in minutes. The crosslinked hydrogel was the same as PEG-APC(18-25)-2 (Example 23).

The samples of DCF-loaded hydrogels were washed with PBS and transferred to tubes with 2 mL PBS (pH 7.4). The tubes were then incubated in a 37° C. water bath shaken at a speed of 100 rev/min. At specific time intervals, the 2 mL aliquot was withdrawn from each tube and replaced with fresh PBS buffer. The DCF in each aliquot was analyzed using the UV VIS spectrophotometer (Shimadzu, UV-2501PC, Japan) at 275 nm. The drug release was calculated based on the standard curve obtained from diclofenac sodium salt in PBS.

As shown in the graph of FIG. 11, the release of diclofenac sodium salt was sustained for four hours (96% of the diclofenac sodium salt was released in that time). The loading efficiency was 100% based on cumulative drug release profile.

Example 27

DNA-Loaded Hydrogel

This example demonstrates DNA can be occluded within the crosslinked hydrogel. Synthetic Y-shape DNA bearing a Cy5 fluorophore was used as the model DNA molecule. The Y-DNA was synthesized according to the published protocol [Y. Li, Y. T. H. Cu, D. Luo, "Multiplexed detection of pathogen DNA with DNA-based fluorescence nanobarcodes," Nature Biotechnology, volume 23, pages 885-889, (2005), and Y. Li, Y. D. Tseng, S. Y. Kwon, L. d'Espaux, J. S. Bunch, P. L. McEuen, D. Luo, "Controlled assembly of dendrimer-like DNA," Nature Materials, volume 3, pages 38-42, (2004)], summarized as follows.

Three single stranded DNA (ssDNA), which are partially complementary to each other, were annealed and hybridized to form the Y-DNA. The three ssDNA have the following sequences:

```
Sequence 1 (SEQ ID NO: 1):
5'-TTGCTGGATCCGCATGATTCGCCGTAAG-3',

Sequence 2 (SEQ ID NO: 2):
5'-CTTACGCGAATGACCGAATCAGCCT-3', and

Sequence 3 (SEQ ID NO: 3):
5'-/Cy5/-AGGCTGATTCGGTTCATGCGGATCCA-3'.
```

One out of the three ssDNA was labeled with Cy5 on the 5' terminal to give single labeled Y-DNA molecular probe, referred to as Cy5 conjugated DNA.

A DNA-loaded hydrogel was prepared using the procedure of Example 26, substituting the diclofenac sodium salt (DCF) with the Cy5 conjugated DNA (100 nanomolar solution in PBS, 7.5 microliters). The distribution of Cy5 conjugated DNA in the crosslinked hydrogel was observed using confocal laser scanning microscopy (CLSM) (Olympus FV300, Japan). DNA-loaded hydrogel samples were washed with PBS and visualized by CLSM at excitation wavelength of 532 nm. PEG-APC(18-25)-2 hydrogel without Cy5 conjugated DNA was used as control. All the observations were conducted using the same conditions. The DNA-loaded hydrogel exhibited strong and uniform red fluorescence throughout the hydrogel, indicating that Cy5 conjugated DNA was successfully encapsulated via electrostatic interactions and distributed evenly within the hydrogel. The control sample without Cy5 conjugated DNA showed no fluorescence, appearing uniformly black.

Example 28

Effect of Electrophilic Non-Polymeric Crosslinking Agent

This example qualitatively demonstrates the effect of a low molecular weight non-polymeric crosslinking agent, pentaerythritol tetraacrylate, on hydrogel formation. The preparation of the hydrogel of Example 23 was followed, using 4.73 mol % pentaerythritol tetraacrylate relative to moles of 4Arm-PEG-acrylate. The mole ratio of pentaerythritol tetraacrylate to 4Arm-PEG-acrylate was 1:21.2.

Thus, 4Arm-PEG-acrylate (1.8 mg, 0.18 micromoles) was dissolved in 10 microliters of triethanolamine buffer (TEOA, 0.3M, pH 8.0) and then reacted with APC (1.57 mg, 0.1 micromoles) in 27 microliters of triethanolamine buffer (TEOA, 0.3M, pH 8.0). The reaction solution was incubated at 37° C. for 2 hours, followed by the addition of pentaerythritol tetraacrylate (PETA) (MW 352.34, 1 mg/L in TEOA, 3.0 microliters, 0.00851 micromoles). 4Arm-PEG-SH solution (1.64 mg in 10 microliters TEOA, 0.164 micromoles) was then added to the solution. The reaction mixture was kept at 37° C., and the hydrogel was formed in minutes. It was observed that gelation time decreased to 6 min (from 10 min for Example 23) in the presence of pentaerythritol tetraacrylate.

The structure of the resulting hydrogel is shown in Scheme 7.

Scheme 7.

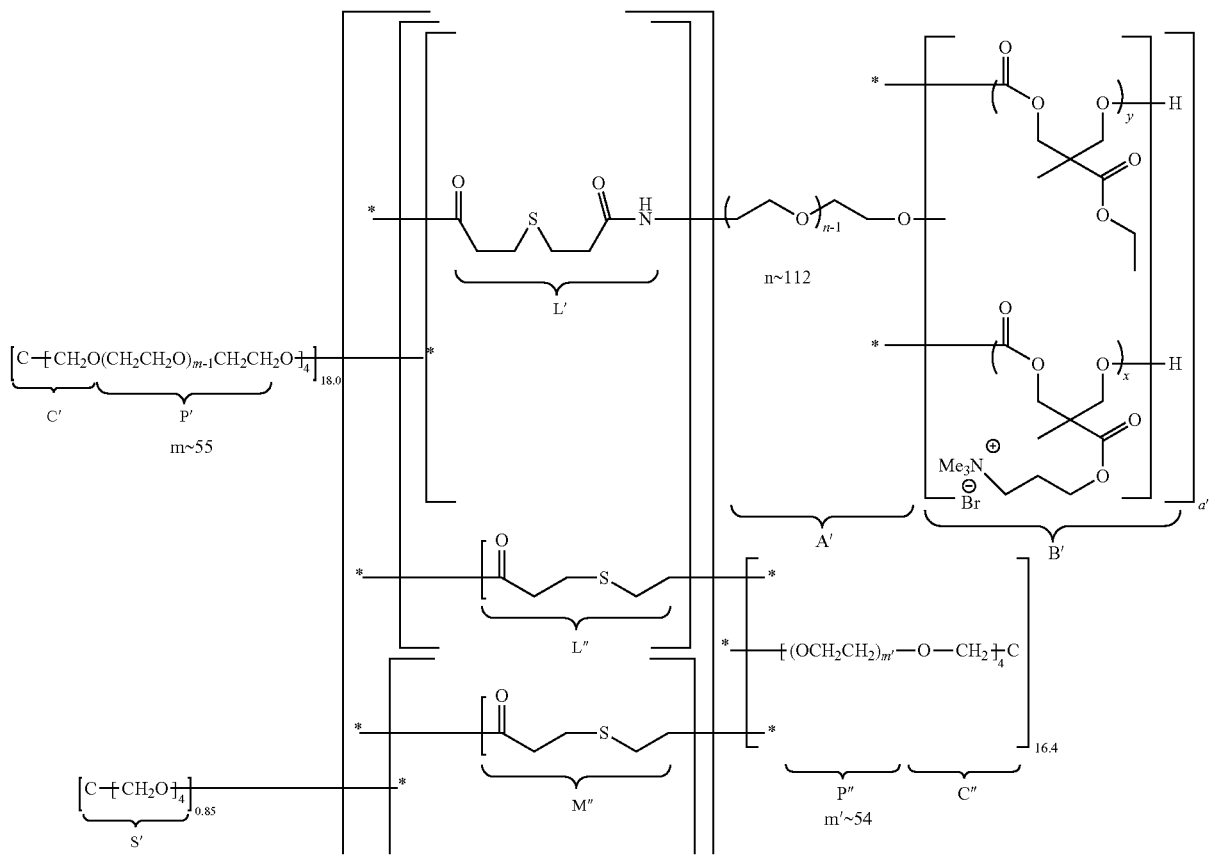

-continued

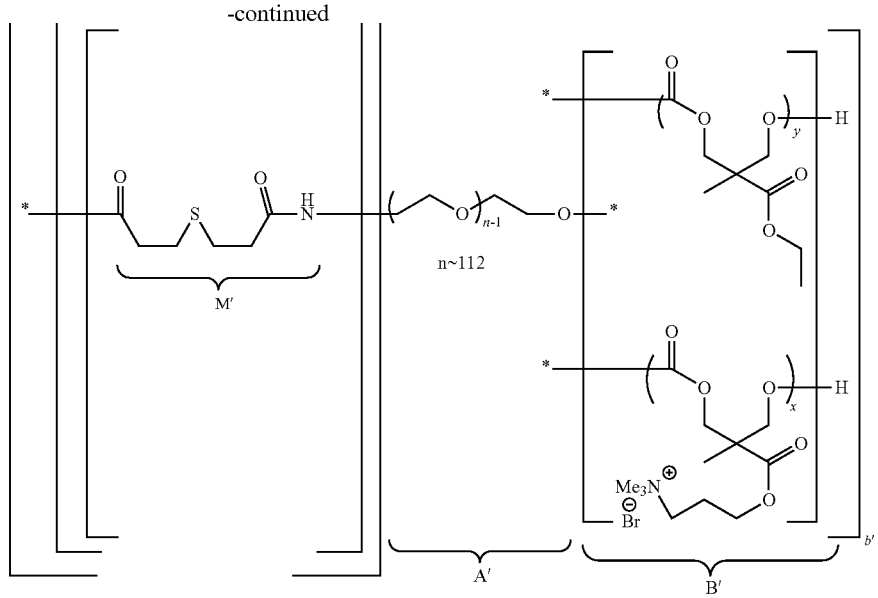

In Scheme 7, C', C", P', P", L', L", M', M", S', A', and B' are shown in accordance with formula (1a). Micromoles of each precursor are multiplied by 100 in Scheme 7, and a'+b'=10.0.

The pentaerythritol tetraacrylate is an example of an electrophilic non-polymeric crosslinking agent $S'[-F'']_{v'}$ that becomes a non-polymeric core group in the hydrogel, where v' is 4, F'' is *—C(C=O)—CH=CH$_2$, and S' is an pentaerythritolyl group C(CH$_2$O—*)$_4$. The non-polymeric core group S' can be covalently linked to two or more members independently selected from the group consisting of chains P''' (e.g., of the 4Arm-PEG-SH), cationic block copolymer A'-B' (e.g., of the PEG-APC(18-25)-2, non-charge block copolymer D'-E' (when present), core groups S''' of nucleophilic non-polymeric crosslinking agents $S'[-N^d]_{w'}$ (when present). In an embodiment, the hydrogel comprises a non-polymeric core group S' covalently linked to two or more members independently selected from the group consisting of chains P''' and block A' of the cationic block copolymer A'-B'. In another embodiment, the hydrogel comprises a non-polymeric core group S' which is covalently linked to two or more members independently selected from the groups consisting of chains P''', block A' the cationic block copolymer A'-B', and block D' of the block copolymer D'-E', wherein S' comprises at least one carbon.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A covalently crosslinked hydrogel comprising:
   three or more divalent poly(alkylene oxide) chains P' covalently linked at respective first end units to a branched first core group C';
   three or more divalent poly(alkylene oxide) chains P''' covalently linked at respective first end units to a branched second core group C''', the chains P''' comprising respective second end units which are covalently linked to between 0% and 100% of respective second end units of chains P' by divalent linking groups L''; and
   at least one pendant cationic block copolymer chain A'-B' which comprises i) a divalent block A' comprising a poly(alkylene oxide) backbone chain having an end unit covalently linked to a second end unit of one of the chains P' by a divalent linking group L', and ii) a monovalent block B' comprising a first repeat unit, the first repeat unit comprising a backbone carbonate group and a cationic side chain group.

2. The hydrogel of claim 1, wherein the first repeat unit comprises a side chain quaternary amine group.

3. The hydrogel of claim 1, wherein the block B' of the block copolymer A'-B' further comprises a non-charged second repeat unit having a backbone carbonate or a backbone ester group.

4. The hydrogel of claim 1, wherein the first branched core group C' and the second branched core group C''' is a pentaerythritolyl group $(C(CH_2O-*)_4)$.

5. The hydrogel of claim 1, wherein L' and L'' comprise a backbone beta-sulfido carbonyl group having the structure:

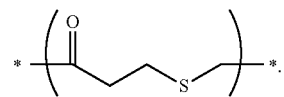

6. The hydrogel of claim 1, wherein the poly(alkylene oxide) backbone of block A' of the block copolymer A'-B' comprises a repeat unit selected from ethylene oxide $*-(CH_2CH_2O)-*$, propylene oxide $*-(CH_2CH(CH_3)O)-*$, and combinations thereof.

7. The hydrogel of claim 1, wherein poly(alkylene oxide) chains P' and chains P''' independently comprise a repeat unit selected from ethylene oxide $*-(CH_2CH_2O)-*$, propylene oxide $*-(CH_2CH(CH_3)O)-*$, and combinations thereof.

8. The hydrogel of claim 1, wherein block B' of the block copolymer A'-B' comprises an end unit capable of initiating a ring opening polymerization of a cyclic carbonyl compound.

9. The hydrogel of claim 1, wherein the hydrogel is an effective antimicrobial agent against at least a Gram positive microbe.

10. The hydrogel of claim 1, further comprising at least one pendant non-charged block copolymer chain D'-E' comprising i) a divalent block D' comprising a poly(alkylene oxide) backbone chain having an end unit covalently linked by a divalent linking group L''' to one of the second end units of chains P', wherein L''' comprises a backbone sulfide group, and ii) a monovalent hydrophobic block E', wherein block E' comprises a repeat unit comprising a backbone carbonate group and a side chain urea group.

11. A method of forming the hydrogel of claim 1, comprising:
   combining i) a first crosslinking agent $C'[-P'-F']_{t'}$, ii) a cationic nucleophilic block copolymer $N^{\alpha}$-A'-B', iii) a base; and iv) a second crosslinking agent $C''[-P''-N^b]_{u'}$, thereby forming a hydrogel precursor mixture; and
   allowing and/or inducing the hydrogel precursor mixture to crosslink, thereby forming the hydrogel;
   wherein
   i) $C'[-P'-F']_{t'}$ comprises $t' \geq 3$ independent divalent poly(alkylene oxide) chains P' comprising respective first end units covalently linked to a branched first core group C' and respective electrophilic second end units F',
   ii) $N^{\alpha}$-A'-B' is formed by organocatalyzed ring opening polymerization, and $N^{\alpha}$-A'-B' comprises a) a divalent block A' comprising a poly(alkylene oxide) backbone linked to a nucleophilic end unit $N^{\alpha}$ capable of reacting with F' to form a divalent linking group L', and b) a monovalent cationic block B' comprising a first repeat unit, the first repeat unit comprising a backbone carbonate group and a cationic side chain group, and
   iii) $C''[-P''-N^b]_{u'}$ comprises $u' \geq 3$ independent divalent poly(alkylene oxide) chains P'' comprising respective first end units covalently linked to a second branched core group C'' and respective nucleophilic second end units $N^b$, wherein each of the second end units is capable of reacting with F' to form a divalent linking group L''.

12. A method, comprising contacting a microbe with the covalently crosslinked hydrogel of claim 1, thereby killing the microbe.

13. An article comprising the covalently crosslinked hydrogel of claim 1 disposed on a surface of a medical device.

14. The article of claim 13, wherein the medical device is selected from the group consisting of swabs, catheters, sutures, stents, bedpans, gloves, facial masks, absorbent pads, absorbent garments, internal absorbent devices, insertable mechanical devices, and wound dressings.

15. A covalently crosslinked hydrogel of formula (1):

$$\left[C'-\!\!\left[-P'-\!\right]_{t'}\right]_{q'} \begin{matrix} *-\!\!\left[-L'-\!\right]-A'-B'\right]_{k'} \\ *-\!\!\left[-L''-\right]\!\!-\!\!\left[-P''-\!\right]_{u'}C''\right]_{j'} \\ *-\!\!\left[-L'''-\right]\!\!-D'-E'\right]_{i'} \end{matrix} \quad (1)$$

wherein
   starred bonds indicate attachment points,
   A'-B' is a pendant cationic block copolymer comprising i) a divalent block A' comprising a poly(alkylene oxide) backbone and ii) a monovalent block B' comprising a first repeat unit, the first repeat unit comprising a backbone carbonate group and a cationic side chain group,
   D'-E' is an optional pendant non-charged amphiphilic block copolymer comprising i) a block D' comprising a poly(alkylene oxide) backbone and a hydrophobic block E',
   each C' is an independent branched first core group comprising at least one carbon and having a valency of t',
   t' is an integer greater than or equal to 3,
   each C'' is an independent branched second core group comprising at least one carbon and having a valency of u',
   u' is an integer greater than or equal to 3,
   each P' is an independent divalent poly(alkylene oxide) chain,
   each P'' is an independent divalent poly(alkylene oxide) chain,
   each C' is linked to t' number of chains P',
   each C'' is linked to u' number of chains P'',
   each L' is an independent divalent linking group that covalently links a chain P' to a block A',
   each L'' is an independent divalent linking group that covalently links a chain P' to a chain P'',
   each L''' is an optional independent divalent linking group that covalently links a chain P' to a block D',
   q' is a number greater than 0 representing moles of C' in the hydrogel,
   j' is a number greater than 0 representing moles of C'' in the hydrogel,
   k' is a number greater than 0 representing moles of block copolymer A'-B' in the hydrogel,
   i' is a number greater than or equal to 0 representing moles of optional block copolymer D'-E' in the hydrogel, and
   between 0% and 100% of the chains P' are independently covalently linked to chains P''.

16. The hydrogel of claim 15, wherein the first repeat unit comprises a side chain quaternary amine group.

17. The hydrogel of claim 15, wherein block E' comprises a side chain urea group.

18. The hydrogel of claim 15, wherein the hydrogel is an effective antimicrobial agent at least a Gram positive microbe.

19. A composition comprising i) the hydrogel of claim 15 and ii) a drug and/or a gene.

20. A method, comprising:
   forming a mixture comprising
   i) a first crosslinking agent $C'[-P'-F']_{t'}$ comprising $t' \geq 3$ independent divalent poly(alkylene oxide) chains P' comprising respective first end units covalently linked to a branched first core group C' and respective electrophilic second end units F',
   ii) a cationic nucleophilic block copolymer $N^{\alpha}$-A'-B' formed by organocatalyzed ring opening polymerization, $N^{\alpha}$-A'-B' comprising a) a divalent block A' comprising a poly(alkylene oxide) backbone linked to a nucleophilic end unit $N^{\alpha}$ capable of reacting with F' to form a divalent linking group L', and b) a monovalent cationic block B' comprising a first repeat unit, the first repeat unit comprising a backbone carbonate group and a cationic side chain group,
   iii) a base, and optionally
   iv) a nucleophilic non-charged amphiphilic block copolymer $N^c$-D'-E' formed by organocatalyzed ring opening polymerization, $N^c$-D'-E' comprising a) a divalent block D' comprising a poly(alkylene oxide) backbone chain having a nucleophilic end unit $N^c$ capable of reacting with F' to form a divalent linking group L''', and b) a monovalent hydrophobic block E;

agitating the mixture, thereby forming an adduct, wherein the adduct comprises unreacted electrophilic groups F';

forming a hydrogel precursor mixture comprising i) the adduct and a second crosslinking agent $C''[-P'''-N^b]_{u'}$ comprising $u' \geq 3$ independent divalent poly(alkylene oxide) chains P''' comprising respective first end units covalently linked to a second branched core group C'' and respective nucleophilic second end units $N^b$ capable of reacting with F' to form a divalent linking group L'';

disposing the hydrogel precursor mixture on a surface of a substrate, thereby forming a hydrogel precursor layer disposed on the surface; and allowing and/or inducing the hydrogel precursor layer to crosslink, thereby forming an antimicrobial layer comprising a covalently crosslinked cationic hydrogel disposed on the surface of the substrate.

21. The method of claim 20, wherein the first repeat unit of block B' comprises a side chain quaternary amine group.

22. The method of claim 21, wherein the hydrogel precursor mixture further comprises a drug and/or a gene, and the antimicrobial layer comprises the hydrogel and the gene and/or the drug occluded therein.

23. A covalently crosslinked hydrogel of formula (1a):

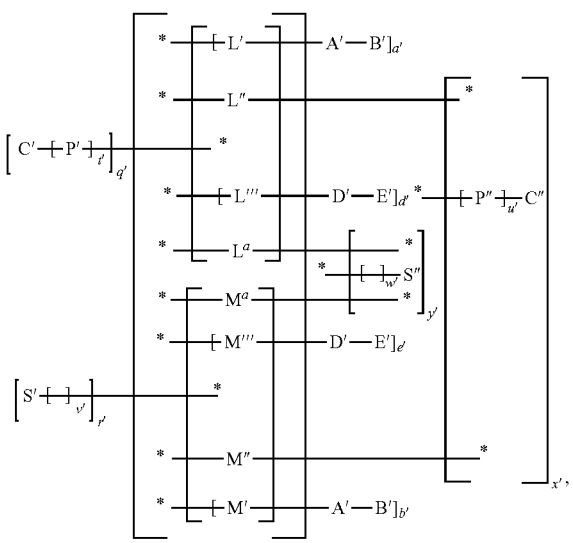

(1a)

wherein starred bonds indicate attachment points,

A'-B' is a pendant cationic block copolymer comprising i) a divalent block A' comprising a poly(alkylene oxide) backbone and ii) a monovalent cationic block B' comprising a first repeat unit, the first repeat unit comprising a backbone carbonate group and a cationic side chain group, D'-E' is a pendant non-charged amphiphilic block copolymer comprising i) a block D' comprising a poly(alkylene oxide) backbone and a hydrophobic block E', each C' is an independent branched first core group comprising at least one carbon and having a valency of t', t' is an integer greater than or equal to 3, each C'' is an independent branched second core group comprising at least one carbon and having a valency of u', u' is an integer greater than or equal to 3, each P' is an independent divalent poly(alkylene oxide) chain, each P''' is an independent divalent poly(alkylene oxide) chain, each L' is an independent divalent linking group that covalently links a chain P' to a block A', each L'' is an independent divalent linking group that covalently links a chain P' to a chain P''', each L''' is an independent divalent linking group that covalently links a chain P' to a block D', each S' is an independent non-polymeric core group comprising at least one carbon and having a valency of v', wherein v' is a positive integer greater than or equal to 2, each S'' is an independent non-polymeric core group comprising at least one carbon and having a valency of w', wherein w' is a positive integer greater than or equal to 2, each $L^a$ is an independent divalent linking group that covalently links a S'' group to a chain P', each $M^a$ is an independent divalent linking group that covalently links a S'' group to a S' group, each M' is an independent divalent linking group that covalently links a S' group to a block A' of block copolymer A'-B', M'' is an independent divalent linking group that covalently links a S' group to a chain P''', M''' is an independent divalent linking group that covalently links a S' group to a block D' of block copolymer D'-E', a' is a number greater than 0 representing moles of A'-B' linked to chains P' in the hydrogel, b' is a number greater than or equal to 0 representing moles of A'-B' linked to S' in the hydrogel, d' is a number greater than or equal to 0 representing moles of D'-E' linked to chains P' in the hydrogel, e' is a number greater than or equal to 0 representing moles of D'-E' linked to S' in the hydrogel, q' is a number greater than 0 representing moles of C' in the hydrogel, x' is a number greater than 0 representing moles of C'' in the hydrogel, y' is a number greater than or equal to 0 representing moles of S'' in the hydrogel, r' is a number greater than or equal to 0 representing moles of S' in the hydrogel, each C' is linked to t' number of chains P', each C'' is linked to u' number of chains P''', each S' group is linked to v' number of linking groups independently selected from the group consisting of M', M'', M''', and $M^a$, each S'' group is linked to w' number of linking groups independently selected from the group consisting of $L^a$ and $M^a$, and between 0% and 100% of the chains P' are independently covalently linked to chains P''' in the hydrogel.

24. The hydrogel of claim 23, wherein the first repeat unit comprises a side chain quaternary amine group.

25. The hydrogel of claim 23, wherein block E' comprises a random copolycarbonate and/or copolyestercarbonate backbone, and a repeat unit having a side chain urea group.

26. A composition comprising i) the hydrogel of claim 23 and ii) a gene and/or a drug.

27. An article, comprising the composition of claim 26 disposed on a surface of a medical device.

28. The article of claim 27, wherein the medical device is selected from the group consisting of swabs, catheters, sutures, stents, bedpans, gloves, facial masks, absorbent pads, absorbent garments, internal absorbent devices, insertable mechanical devices, and wound dressings.

29. A method, comprising:
combining i) a first crosslinking agent $C'[-P'-F']_{t'}$, optionally ii) an electrophilic non-polymeric crosslinking agent, $S'[-F'']_{v'}$, iii) a cationic nucleophilic block copolymer $N^a$-$A'$-$B'$, iv) a base; optionally v) a nucleophilic non-charged amphiphilic block copolymer $N^c$-$D'$-$E'$, vi) a second crosslinking agent $C''[-P'''-N^b]_{u'}$, and optionally vii) a nucleophilic non-polymeric crosslinking agent $S''[-N^d]_{w'}$, thereby forming a hydrogel precursor mixture; and
allowing and/or inducing the hydrogel precursor mixture to crosslink, thereby forming a covalently crosslinked hydrogel;
wherein
i) $C'[-P'-F']_{t'}$ comprises $t' \geq 3$ independent divalent poly(alkylene oxide) chains P' comprising respective first end units covalently linked to a branched first core group C' and respective electrophilic second end units F',
ii) $S'[-F'']_{v'}$ comprises $v' \geq 2$ independent electrophilic groups F'' and a non-polymeric core group S' comprising at least one carbon,
iii) $N^a$-$A'$-$B'$ is formed by organocatalyzed ring opening polymerization, and $N^a$-$A'$-$B'$ comprises a) a divalent block A' comprising a poly(alkylene oxide) backbone linked to a nucleophilic end unit $N^a$ capable of reacting with F' to form a divalent linking group L' and/or reacting with F'' to form a divalent linking group M', and b) a monovalent cationic block B' comprising a first repeat unit, the first repeat unit comprising a backbone carbonate group and a cationic side chain group,
iv) $N^c$-$D'$-$E'$ is formed by organocatalyzed ring opening polymerization, and $N^c$-$D'$-$E'$ comprises a) a divalent block D' comprising a poly(alkylene oxide) backbone chain having an end unit $N^c$ capable of reacting with F' to form a divalent linking group L''' and/or reacting with F''' to form divalent linking group M''', and b) a monovalent block E;
v) $C''[-P'''-N^b]_{u'}$ comprises $u' \geq 3$ independent divalent poly(alkylene oxide) chains P''' comprising respective first end units covalently linked to a second branched core group C'' and respective nucleophilic second end units $N^b$, wherein each of the second end units is capable of reacting with F' to form a divalent linking group L'' and/or reacting with F'' to form a divalent linking group M'', and
vi) $S''[-N^d]_{w'}$ comprises $w' \geq 2$ nucleophilic groups $N^d$ and a non-polymeric core group S'' comprising at least one carbon, wherein $N^d$ is capable of reacting with F' to form a divalent linking group $L^a$ and/or reacting with F''' to form a divalent linking group $M^a$.

30. The method of claim 29, wherein the first repeat unit of block B' comprises a side chain quaternary amine group.

31. The method of claim 29, wherein F' and/or F''' react by a Michael addition reaction, thereby forming the hydrogel.

32. The method of claim 29, wherein block E' of $N^c$-$D'$-$E'$ comprises a side chain urea group.

33. The method of claim 29, wherein the hydrogel precursor mixture further comprises a gene and/or a drug, and the hydrogel is a loaded hydrogel comprising the gene and/or the drug occluded therein.

34. The method of claim 29, further comprising disposing the hydrogel precursor mixture on a surface of a substrate before substantial crosslinking occurs, thereby forming a hydrogel precursor layer; and allowing and/or inducing the hydrogel precursor layer to crosslink, thereby forming an antimicrobial layer comprising the hydrogel disposed on the surface of the substrate.

35. The method of claim 34, wherein the substrate is a medical device selected from the group consisting of swabs, catheters, sutures, stents, bedpans, gloves, facial masks, absorbent pads, absorbent garments, internal absorbent devices, insertable mechanical devices, and wound dressings.

* * * * *